United States Patent

Fischer et al.

[11] Patent Number: 6,100,220
[45] Date of Patent: Aug. 8, 2000

[54] THIOPHENE DERIVATIVES

[75] Inventors: Reiner Fischer, Monheim, Germany; Jacques Dumas, Orange, Conn.; Thomas Bretschneider, Lohmar, Germany; Bernd Gallenkamp, Wuppertal, Germany; Folker Lieb, Leverkusen, Germany; Konrad Wernthaler, Kienberg, Germany; Christoph Erdelen, Liechlingen, Germany; Ulrike Wachendorff-Neumann, Neuwied, Germany; Norbert Mencke, Leverkusen, Germany; Andreas Turberg, Erkrath, Germany

[73] Assignee: Bayer Aktiengesellschaft, Leverkusen

[21] Appl. No.: 09/339,782

[22] Filed: Jun. 24, 1999

Related U.S. Application Data

[62] Division of application No. 09/089,945, Jun. 3, 1998, which is a division of application No. 08/836,336, May 9, 1997, Pat. No. 5,807,805.

[30] Foreign Application Priority Data

Nov. 17, 1994 [DE] Germany ............... 44 40 899
Jul. 26, 1995 [DE] Germany ............... 195 27 190

[51] Int. Cl.$^7$ ............ A01N 43/10; A01N 43/06; A01N 43/12; C07D 333/56; C07D 409/00
[52] U.S. Cl. ............ 504/289; 514/444; 514/443; 549/58; 549/60
[58] Field of Search ............ 504/289; 514/444; 514/443; 549/58, 60

[56] References Cited

U.S. PATENT DOCUMENTS 5,207,817 5/1993 Kramer et al. .

(List continued on next page.)

FOREIGN PATENT DOCUMENTS 0 355 599 2/1990 European Pat. Off. .

(List continued on next page.)

*Primary Examiner*—Deborah C. Lambkin
*Attorney, Agent, or Firm*—Norris, McLaughlin & Marcus

[57] ABSTRACT

The invention relates to novel thiophene derivatives of the formula (I)

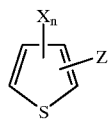

(I)

in which
X represents halogen, alkyl, alkoxy, alkylthio, halogenoalkyl, halogenoalkoxy, nitro or cyano, or two substituents X, together with the carbon atoms to which they are attached, form a saturated or unsaturated, optionally substituted ring, n represents a number from 1 to 3, and Z represents one of the groups

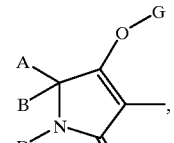
(1)

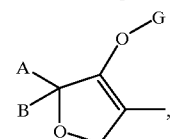

(2)

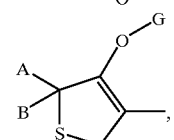

(3)

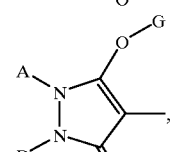

(4)

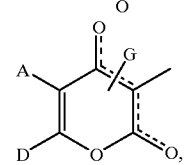

(5)

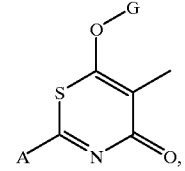

(6)

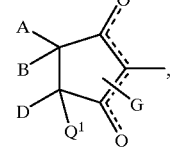

(7)

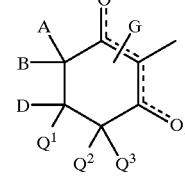

(8)

in which A, B, D, G, $Q^1$, $Q^2$ and $Q^3$ have the meaning given in the description, to processes for their preparation and to their use as pesticides and herbicides.

20 Claims, No Drawings

U.S. PATENT DOCUMENTS

| | | | |
|---|---|---|---|
| 5,258,360 | 11/1993 | Anthony et al. | 504/289 |
| 5,262,383 | 11/1993 | Fischer et al. | |
| 5,726,125 | 3/1998 | Phillion et al. | 504/193 |
| 5,728,696 | 3/1998 | Kuhn et al. | 514/235.5 |
| 5,869,427 | 2/1999 | Yoshikawa et al. | 504/209 |

FOREIGN PATENT DOCUMENTS

| | | |
|---|---|---|
| 0 423 482 | 4/1991 | European Pat. Off. . |
| 0 595 130 | 5/1994 | European Pat. Off. . |
| 42 16 814 | 1/1993 | Germany . |
| 44 13 669 | 1/1995 | Germany . |
| 44 10 420 | 9/1995 | Germany . |

THIOPHENE DERIVATIVES

This application is a division of application Ser. No. 09/089,945, filed Jun. 3, 1998 (now allowed); which is a division of application Ser. No. 08/836,336 filed May 9, 1997 (now U.S. Pat. No. 5,807,805).

The invention relates to novel thiophene derivatives, to a number of processes for their preparation and to their use as pesticides and herbicides.

4-(Aryl- and aralkyl-thienyl)-3-hydroxy-3-pyrroline-2,5-dione derivatives are known to have pharmaceutical properties (ZA 8006-788).

Novel thiophene derivatives have now been found of the formula (I)

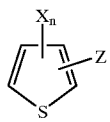

(I)

in which

X represents halogen, alkyl, alkoxy, alkylthio, halogenoalkyl, halogenoalkoxy, nitro or cyano, or two substituents X together with the carbon atoms to which they are attached, form a saturated or unsaturated, optionally substituted ring, n represents 1, 2 or 3, and Z represents one of the groups

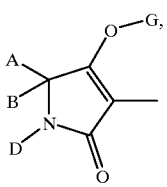

(1)

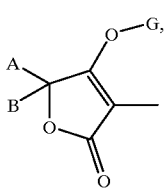

(2)

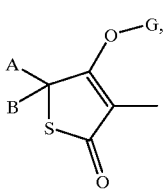

(3)

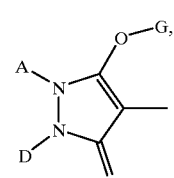

(4)

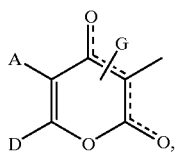

(5)

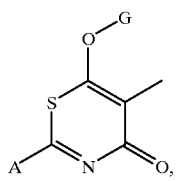

(6)

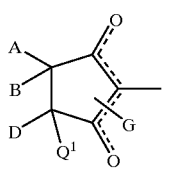

(7)

(8)

in which

A represents hydrogen, optionally halogen-substituted alkyl, alkenyl, alkoxyalkyl, alkylthioalkyl, saturated or unsaturated, optionally substituted cycloalkyl which is optionally interrupted by at least one heteroatom, or represents aryl, arylalkyl, or hetaryl each of which is optionally substituted by halogen, alkyl, halogenoalkyl, alkoxy or nitro, B represents hydrogen, alkyl or alkoxyalkyl, or A and B, together with the carbon atom to which they are attached, represent a saturated or unsaturated, unsubstituted or substituted ring which is optionally interrupted by at least one heteroatom, D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom, $Q^1$, $Q^2$ and $Q^3$, independently of one another, represent hydrogen or optionally substituted alkyl, or B and $Q^1$ together represent an optionally substituted alkanediyl group, G represents hydrogen (a) or one of the groups

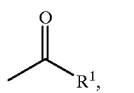 (b)

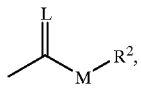 (c)

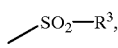 (d)

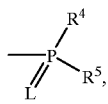 (e)

E or (f)

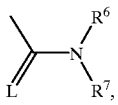 (g)

in which
E represents a metal ion equivalent or an ammonium ion,
L represents oxygen or sulfur,
M represents oxygen or sulfur,
$R^1$ represents in each case optionally halogen-substituted alkyl, alkenyl, alkoxyalkyl, alkylthioalkyl, polyalkoxyalkyl or cycloalkyl which is optionally substituted by halogen, alkyl or alkoxy and may be interrupted by at least one heteroatom, or represents in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or in each case optionally substituted cycloalkyl, phenyl or benzyl,
$R^3$, $R^4$ and $R^5$, independently of one another, represent in each case optionally halogen-substituted alkyl, alkoxy, alkylamino, dialkylamino, alkylthio, alkenylthio, cycloalkylthio and in each case optionally substituted phenyl, phenylalkyl, phenoxy or phenylthio,
$R^6$ and $R^7$, independently of one another, represent hydrogen, in each case optionally halogen-substituted alkyl, cycloalkyl, alkenyl, alkoxy, alkoxyalkyl, optionally substituted phenyl, optionally substituted benzyl, or represent, together with the nitrogen atom to which they are attached, a ring which is optionally interrupted by oxygen or sulfur.

The compounds of the formula (I) may themselves and in dependence on the nature of the substituents be present as geometrical and/or optical isomers or isomer mixtures, in varying composition, which can if desired be separated in a conventional manner. Both the pure isomers and the isomer mixtures, their preparation and use and compositions containing them are part of the claimed invention. However, for the sake of simplicity, the text below will always refer to compounds of the formula (I) although what are meant are both the pure compounds and, if appropriate, mixtures with different proportions of isomeric compounds.

Including the definitions (1) to (8) for the group Z results in the following principal structures (I-1) to (I-8):

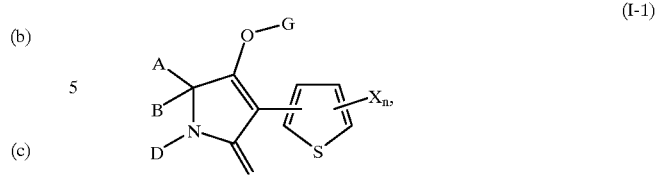 (I-1)

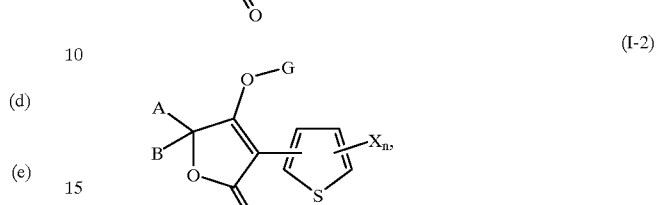 (I-2)

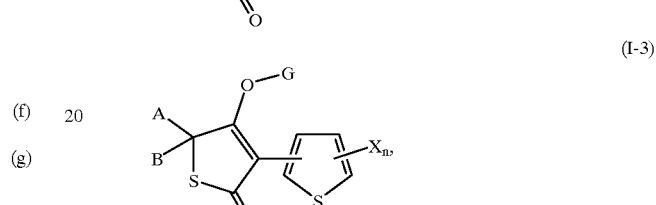 (I-3)

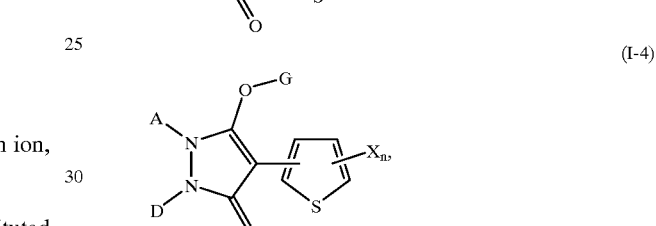 (I-4)

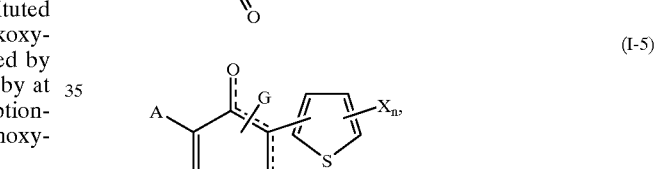 (I-5)

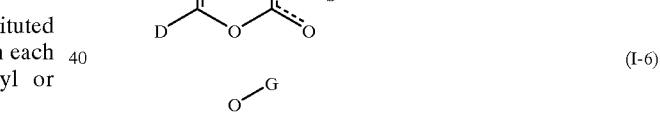 (I-6)

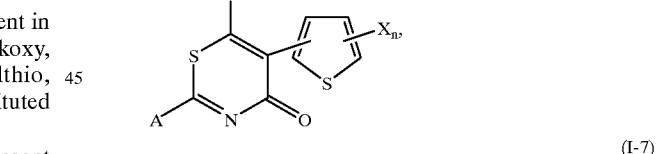 (I-7)

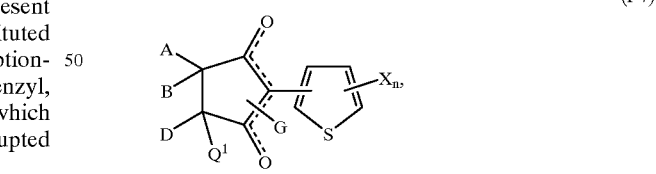 (I-8)

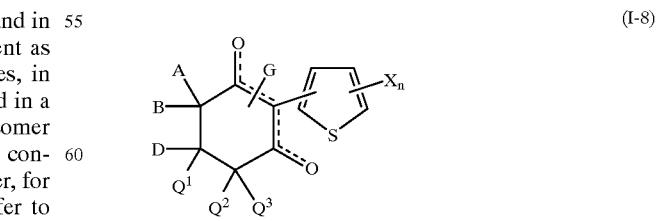

in which
A, B, D, G, $Q^1$, $Q^2$, $Q^3$, X and n have the meaning given above, and, taking into account the position of the substituent Z in the thiophene ring, in the following structures (I-1A) to (I-8A) and (I-1B) to (I-8B):
(I-1 A)
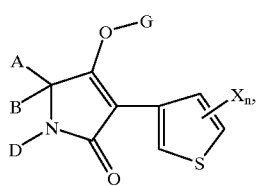
(I-2 A)
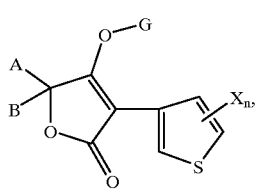
(I-3 A)
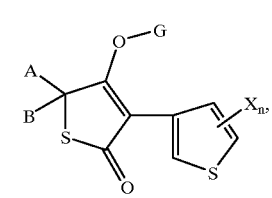
(I-4 A)
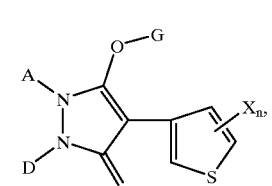
(I-5 A)
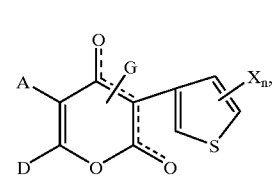
(I-6 A)
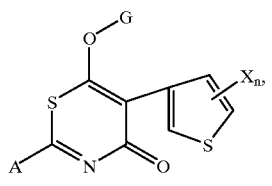
(I-7 A)
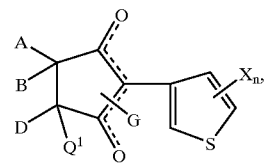
(I-8 A)
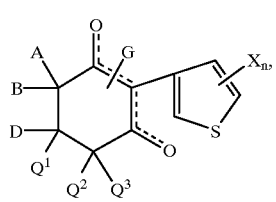
-continued
(I-1 B)
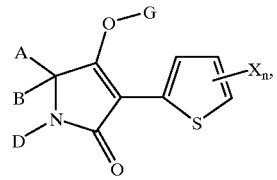
(I-2 B)
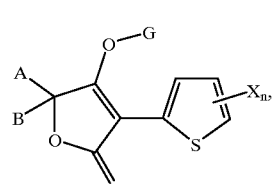
(I-3 B)
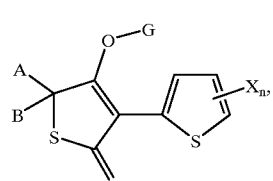
(I-4 B)
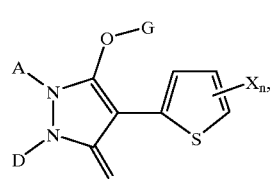
(I-5 B)
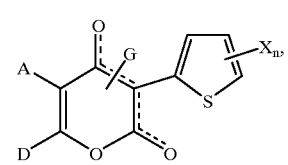
(I-6 B)
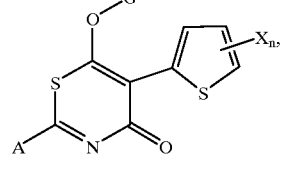
(I-7 B)
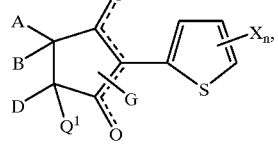
(I-8 B)
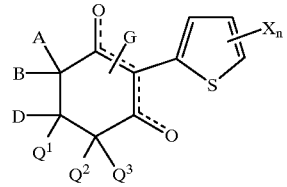

in which
A, B, D, G, $Q^1$, $Q^2$, $Q^3$, X and n have the meaning given above.
Including the various definitions (a), (b), (c), (d), (e), (f) and (g) for the group G results in the following principal structures (I-1 A-a) to (I-1 A-g) and (I-1 B-a) to (I-1 B-g) if Z represents the group (1)
(I-1-a):
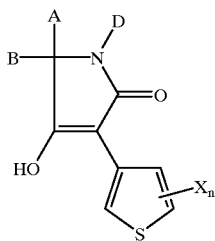
(I-1 A-a)
(I-1-b):
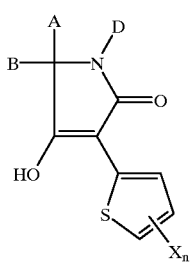
(I-1 B-a)
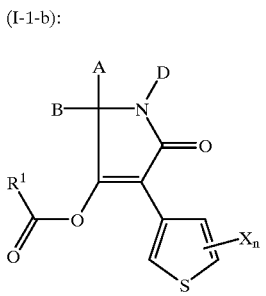
(I-1 A-b)
(I-1-c):
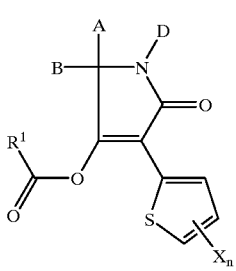
(I-1 B-b)
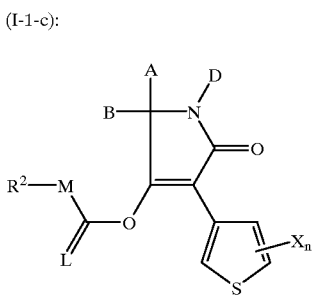
(I-1 A-c)
(I-1 B-c)
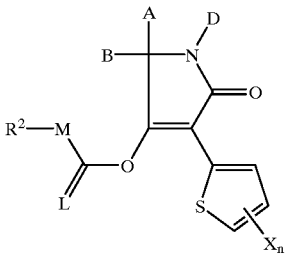
(I-1-d):
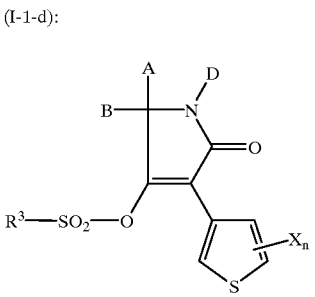
(I-1 A-d)
(I-1 B-d)
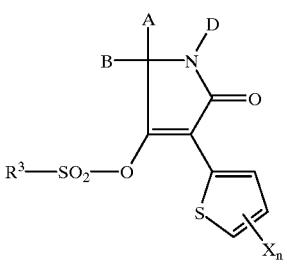
(I-1-e):
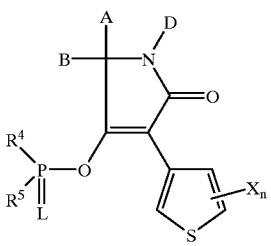
(I-1 A-e)
(I-1 B-e)
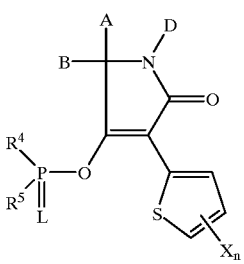

(I-1-f):
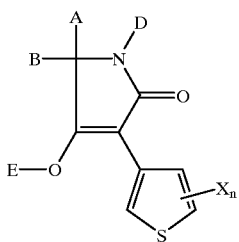
(I-1 A-f)
(I-1 B-f):
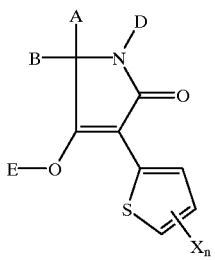
(I-1 B-f)
(I-1-g):
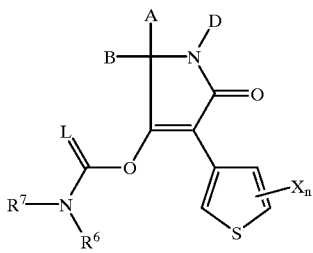
(I-1 A-g)
(I-1 B-g):
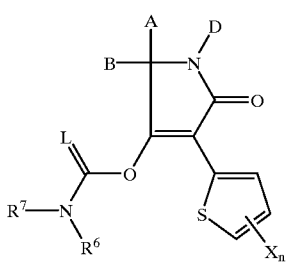
(I-1 B-g)
in which
A, B, D, E, L, M, X, $R^1$, $R^2$, $R^3$, $R^4$, $R^5$, $R^6$, $R^7$ and n have the meanings given above.
Including the various definitions (a), (b), (c), (d), (e), (f) and (g) for the group G results in the following principal structures (I-2 A-a) to (I-2 A-g) and (I-2 B-a) to (I-2 B-g) if Z represents the group (2)
(I-2-a):
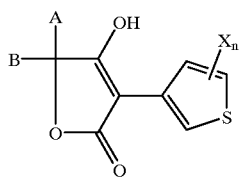
(I-2 A-a)
(I-2 B-a)
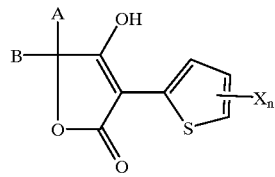
(I-2-b):
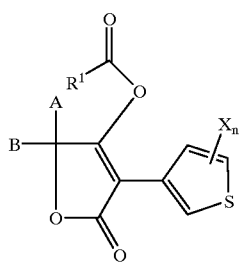
(I-2 A-b)
(I-2 B-b)
(I-2-c):
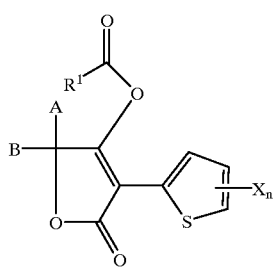
(I-2 A-c)
(I-2 B-c)
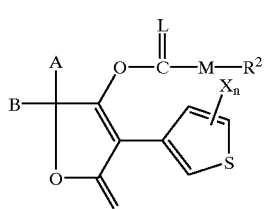
(I-2-d):
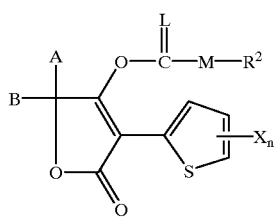
(I-2 A-d)
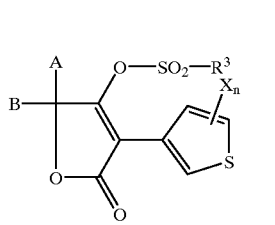

(I-2 B-d)
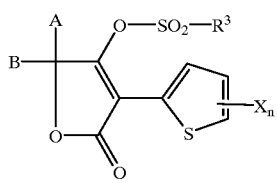
(I-2-e):
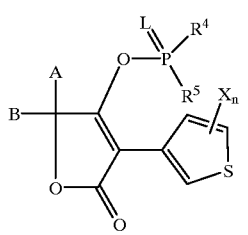
(I-2 B-e)
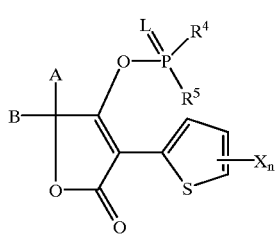
(I-2-f):
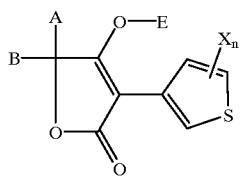
(I-2 B-f)
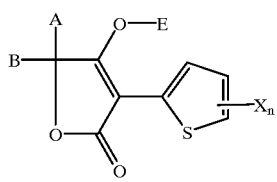
(I-2-g):
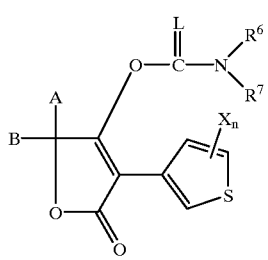
(I-2 A-e)
(I-2 A-f)
(I-2 A-g)
(I-2 B-g)
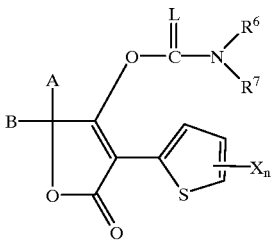
in which
A, B, E, L, M, X, $R^1$, $R^2$, $R^3$, $R^4$, $R^5$, $R^6$, $R^7$ and n have the meanings given above.
Including the various definitions (a), (b), (c), (d), (e), (f) and (g) for the group G results in the following principal structures (I-3 A-a) to (I-3 A-g) and (I-3 B-a) to (I-3 B-g) if Z represents the group (3)
(I-3-a):
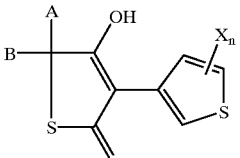
(I-3 A-a)
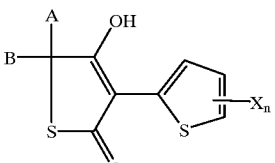
(I-3 B-a)
(I-3-b):
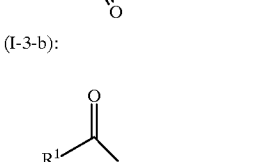
(I-3 A-b)
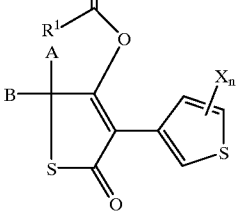
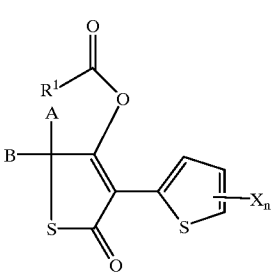
(I-3 B-b)

-continued
(I-3-c):
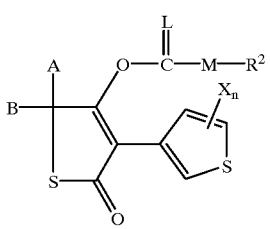
(I-3-d):
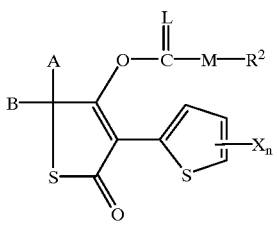
(I-3-e):
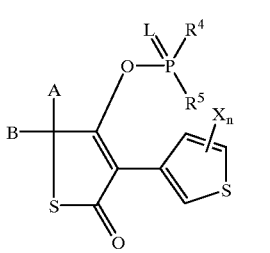
(I-3 A-c)
(I-3 B-c)
(I-3 A-d)
(I-3 B-d)
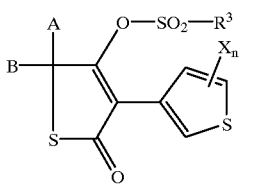
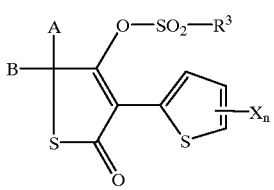
(I-3 A-e)
(I-3 B-e)
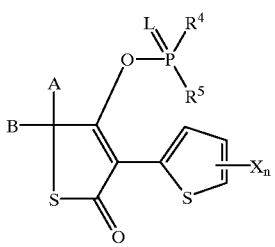
-continued
(I-3-f):
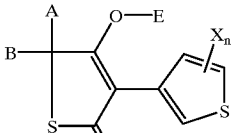
(I-3-g):
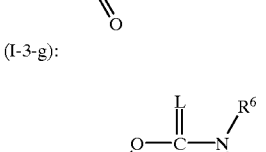
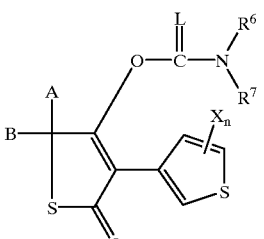
(I-3 A-f)
(I-3 B-f)
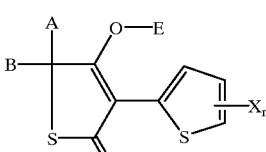
(I-3 A-g)
(I-3 B-g)
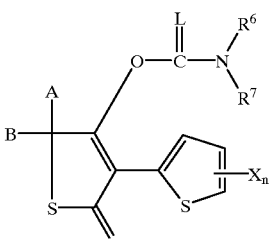
in which
A, B, E, L, M, X, $R^1$, $R^2$, $R^3$, $R^4$, $R^5$, $R^6$, $R^7$ and n have the meanings given above.
Including the various definitions (a), (b), (c), (d), (e), (f) and (g) for the group G results in the following principal structures (I-4 A-a) to (I-4 A-g) and (I-4 B-a) to (I-4 B-g) if Z represents the group (4)
(I-4-a):
(I-4 A-a)
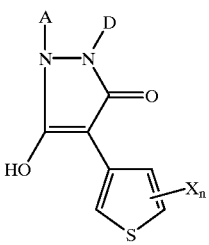

-continued
(I-4 B-a)
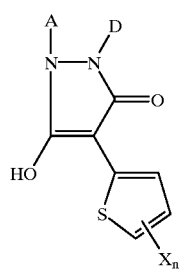
(I-4-b):
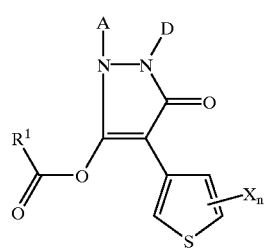
(I-4-c):
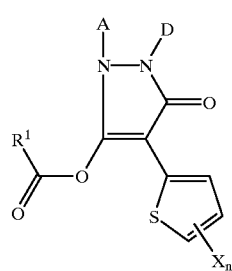
-continued
(I-4-d):
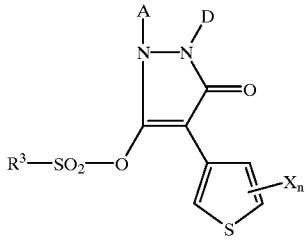
(I-4 A-d)
(I-4 A-b)
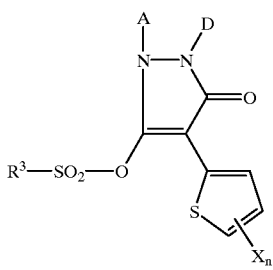
(I-4 B-d)
(I-4-e):
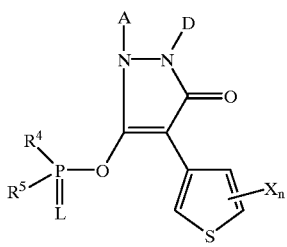
(I-4 A-e)
(I-4 A-c)
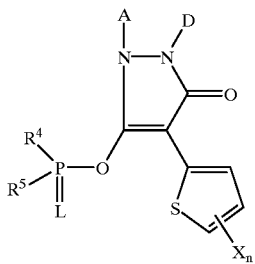
(I-4 B-e)
(I-4 B-c)
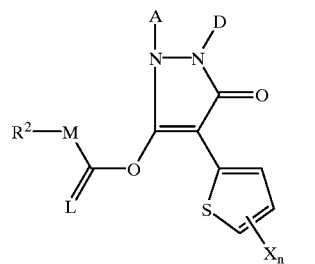
(I-4-f):
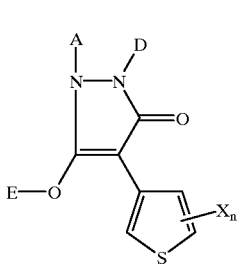
(I-4 A-f)

-continued (I-4 B-f)

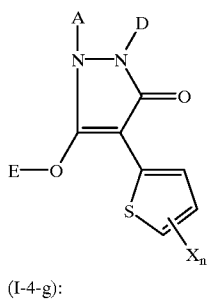

(I-4-g):

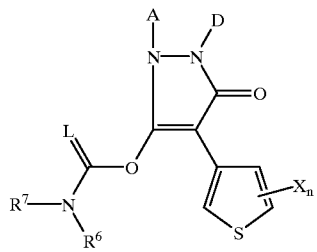

(I-4 B-g)

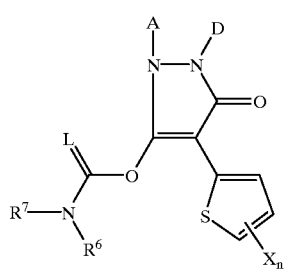

in which
A, D, E, L, M, X, $R^1$, $R^2$, $R^3$, $R^4$, $R^5$, $R^6$, $R^7$ and n have the meanings given above.

The compounds of the formula (I-5) may, depending on the position of the substituent G, be present in the two isomeric forms of the formulae $(I-5)_a$ and $(I-5)_b$ $(I-5)_a$

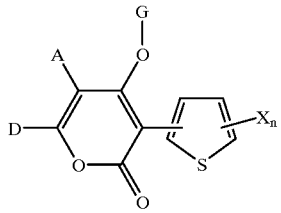

$(I-5)_b$

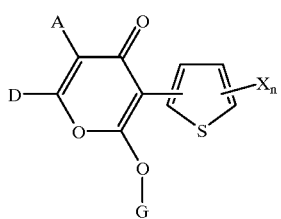

which is what the dashed line in the formula (I-5) is intended to express.

The compounds of the formulae $(I-5)_a$ and $(I-5)_b$ may be present both as mixtures and in the form of their pure isomers. Mixtures of compounds of the formulae $(I-5)_a$ and $(I-5)_b$ can if desired be separated by physical methods in a manner known per se, for example by chromatographic methods.

For reasons of improved clarity, in each case only one of the possible isomers is listed in the text below. This does not rule out the possibility that the compounds may, if desired, be present in the form of the isomer mixtures or in the other isomeric form.

Including the various definitions (a), (b), (c), (d), (e), (f) and (g) for the group G results in the following principal structures (I-5 A-a) to (I-5 A-g) and (I-5 B-a) to (I-5 B-g) if Z represents the group (5)

(I-5-a):

(I-5 A-a)

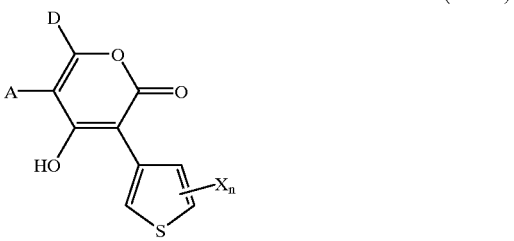

(I-5 B-a)

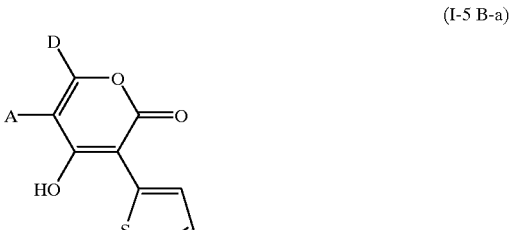

(I-5-b):

(I-5 A-b)

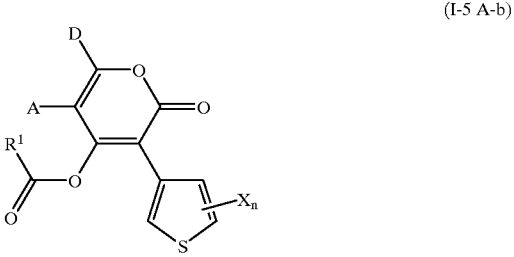

(I-5 B-b)

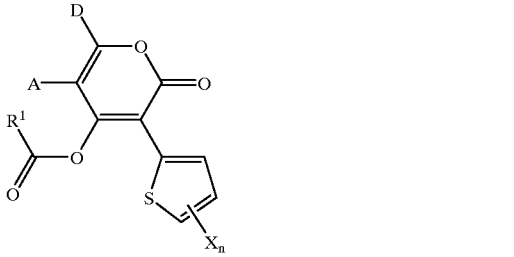

-continued
(I-5-c):
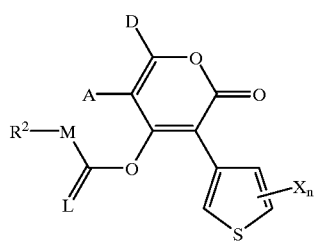
(I-5-d):
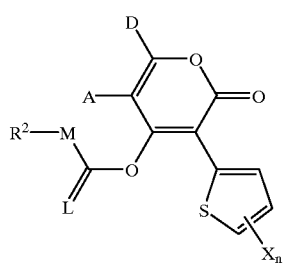
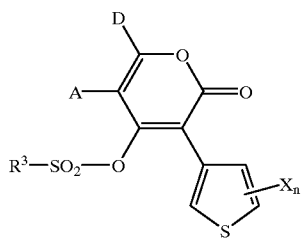
(I-5-e):
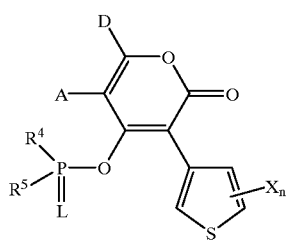
(I-5 A-c)
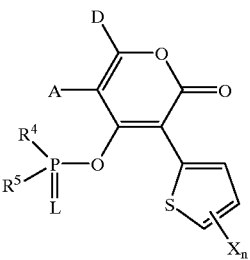
(I-5 B-e)
(I-5 B-c)
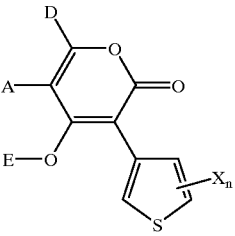
(I-5-f):
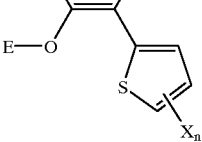
(I-5 A-f)
(I-5 A-d)
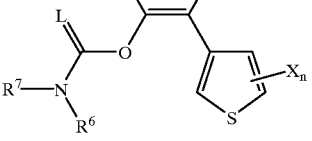
(I-5 B-f)
(I-5-g):
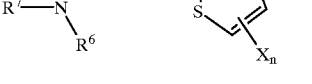
(I-5 A-g)
(I-5 B-d)
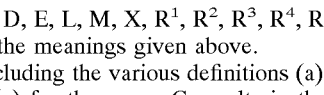
(I-5 B-g)
(I-5 A-e)
in which
A, D, E, L, M, X, $R^1$, $R^2$, $R^3$, $R^4$, $R^5$, $R^6$, $R^7$ and n have the meanings given above.
Including the various definitions (a), (b), (c), (d), (e), (f) and (g) for the group G results in the following principal structures (I-6 A-a) to (I-6 A-g) and (I-6 B-a) to (I-6 B-g) if Z represents the group (6)

(I-6-a):
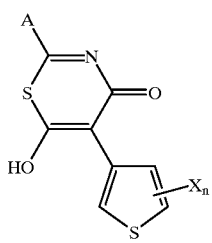
(I-6 A-a)
(I-6 B-c)
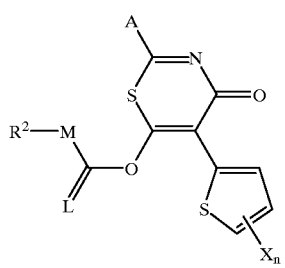
(I-6 B-a)
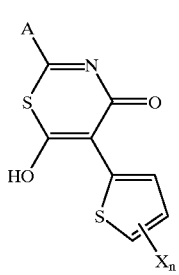
(I-6-d):
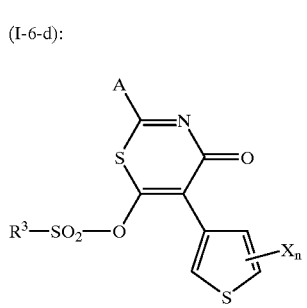
(I-6 A-d)
(I-6-b):
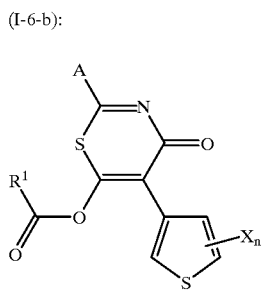
(I-6 A-b)
(I-6 B-d)
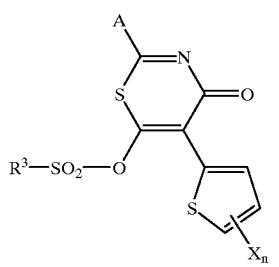
(I-6 B-b)
(I-6-e):
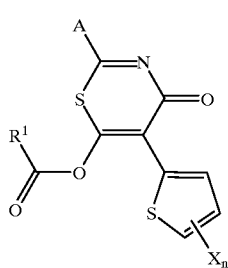
(I-6 A-e)
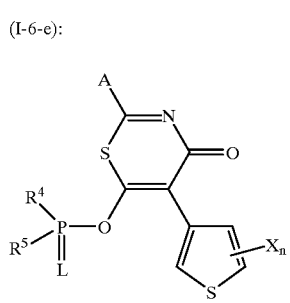
(I-6-c):
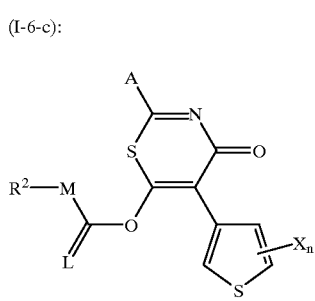
(I-6 A-c)
(I-6 B-e)
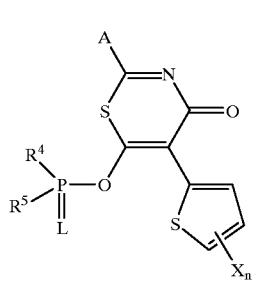

(I-6-f): 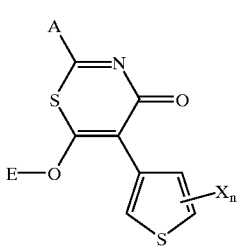

(I-6-g): 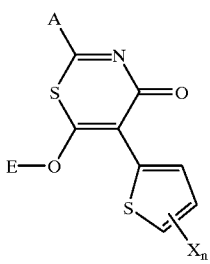

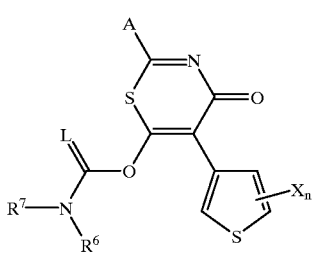

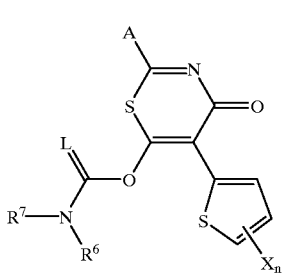

in which

A, E, L, M, X, $R^1$, $R^2$, $R^3$, $R^4$, $R^5$, $R^6$, $R^7$ and n have the meanings given above.

The compounds of the formula (I-7) may, depending on the position of the substituent G, be present in the two isomeric forms of the formulae $(I-7)_a$ and $(I-7)_b$ $(I-7)_a$

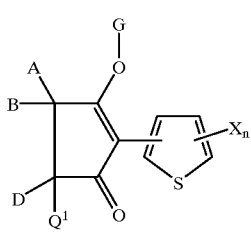

(I-6 A-f)

(I-6 B-f)

(I-6 A-g)

(I-6 B-g)

$(I-7)_b$

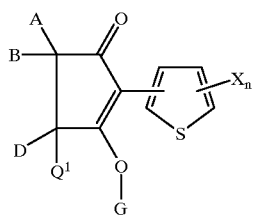

which is what the dashed line in the formula (I-7) is intended to express.

The compounds of the formulae $(I-7)_a$ and $(I-7)_b$ may be present both as mixtures and in the form of their pure isomers. Mixtures of compounds of the formulae $(I-7)_a$ and $(I-7)_b$ can if desired be separated by physical methods in a manner known per se, for example by chromatographic methods.

For reasons of improved clarity, in each case only one of the possible isomers is listed in the text below. This does not rule out the possibility that the compounds may, if desired, be present in the form of the isomer mixtures or in the other isomeric form.

Including the various definitions (a), (b), (c), (d), (e), (f) and (g) for the group G results in the following principal structures (I-7 A-a) to (I-7 A-g) and (I-7 B-a) to (I-7 B-g) if Z represents the group (7)

(I-7-a):

(I-7 A-a)

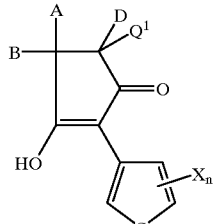

(I-7 B-a)

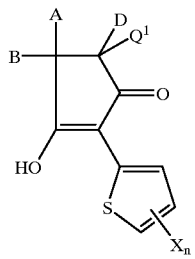

(I-7-b):

(I-7 A-b)

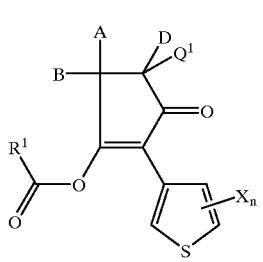

(I-7 B-b)
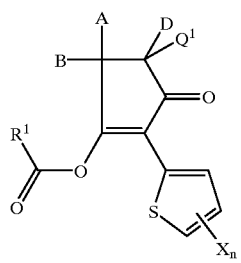
(I-7-c):
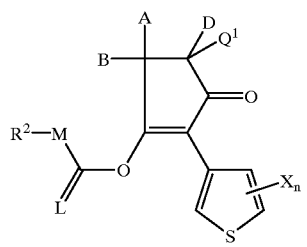
(I-7 B-c)
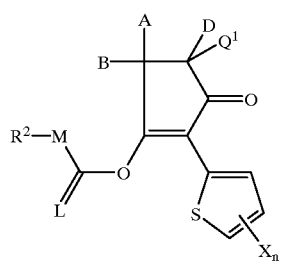
(I-7-d):
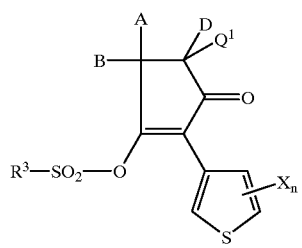
(I-7 B-d)
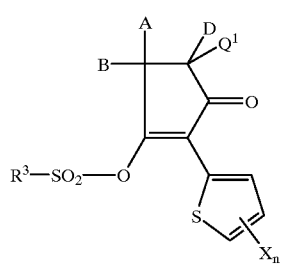
(I-7-e):
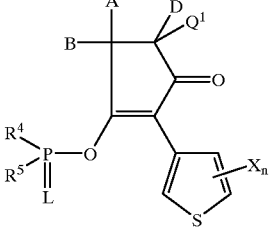
(I-7 B-e)
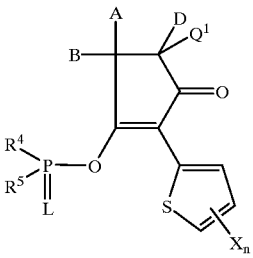
(I-7-f):
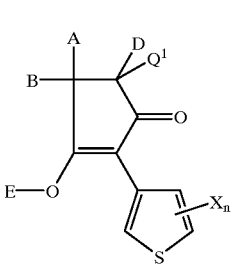
(I-7 B-f)
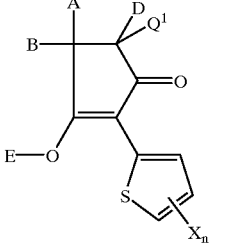
(I-7-g):
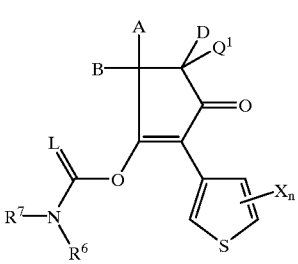

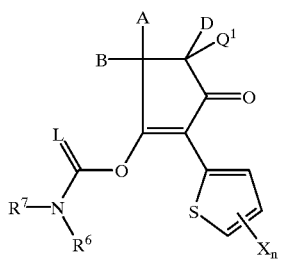
(I-7 B-g)

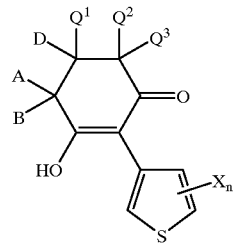
(I-8-a):

(I-8 A-a)

in which

A, B, D, E, L, M, $Q^1$, X, $R^1$, $R^2$, $R^3$, $R^4$, $R^5$, $R^6$, $R^7$ and n have the meanings given above.

The compounds of the formula (I-8) may, depending on the position of the substituent G, be present in the two isomeric forms of the formulae (I-8)$_a$ and (I-8)$_b$

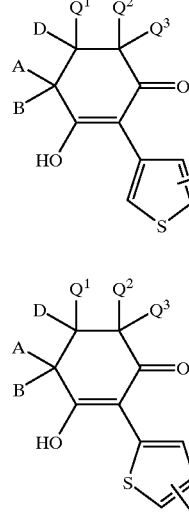

(I-8)$_a$ (I-8 B-a)

(I-8)$_b$

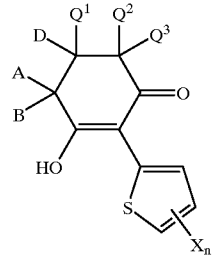
(I-8-b):

(I-8 A-b)

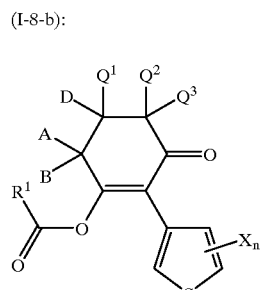

which is what the dashed line in the formula (I-8) is intended to express.

The compounds of the formulae (I-8)$_a$ and (I-8)$_b$ may be present both as mixtures and in the form of their pure isomers. Mixtures of compounds of the formula (I-8)$_a$ and (I-8)$_b$) can if desired be separated by physical methods in a manner known per se, for example by chromatographic methods.

For reasons of improved clarity, in each case only one of the possible isomers is listed in the text below. This does not rule out the possibility that the compounds may, if desired, be present in the form of the isomer mixtures or in the other isomeric form.

Including the various definitions (a), (b), (c), (d), (e), (f) and (g) for the group G results in the following principal structures (I-8 A-a) to (I-8 A-g) and (I-8 B-a) to (I-8 B-g) if Z represents the group (8)

(I-8 B-b)

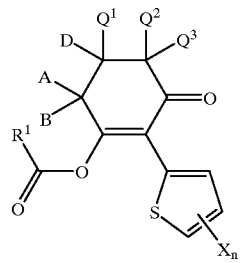

(I-8-c):

(I-8 A-c)

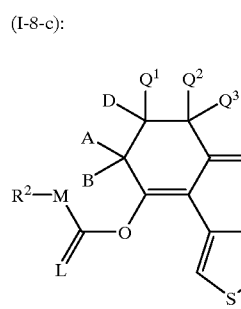

(I-8 B-c)
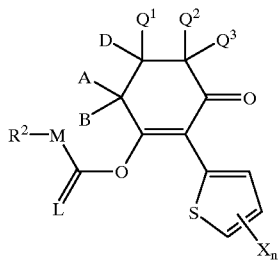
(I-8-d):
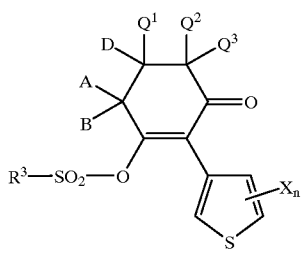
(I-8-e):
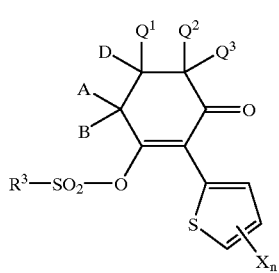
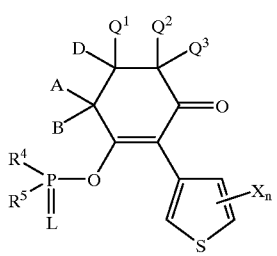
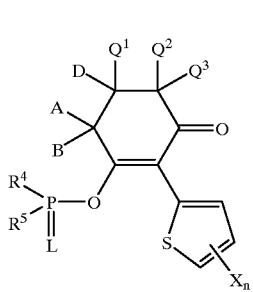
(I-8-f):
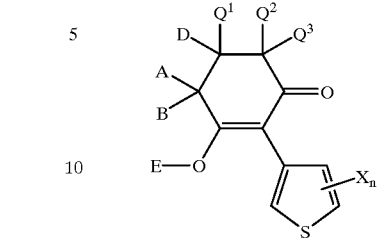
(I-8 A-d)
(I-8 B-d)
(I-8 A-e)
(I-8 B-e)
(I-8 A-f)
(I-8 B-f)
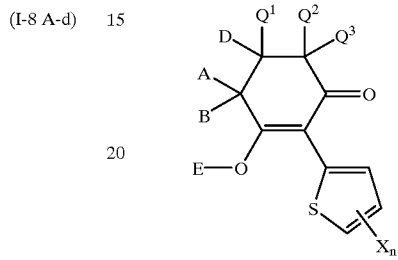
(I-8-g):
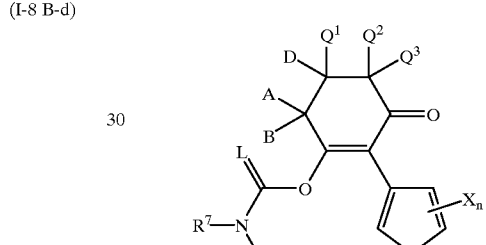
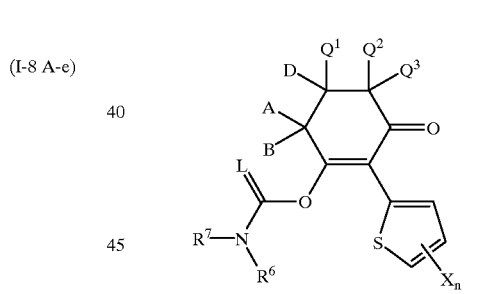
(I-8 A-g)
(I-8 B-g)
in which
A, B, D, E, L, M, $Q^1$, $Q^2$, $Q^3$, X, $R^1$, $R^2$, $R^3$, $R^4$, $R^5$, $R^6$, $R^7$ and n have the meanings given above.
It has additionally been found that the compounds of the formula (I) are obtained by one of the processes described below:
(A) 3-Thienylpyrrolidine-2,4-diones or their enols of the formula (I-1-a)

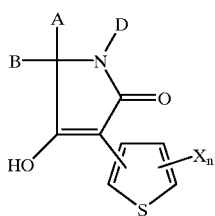
(I-1-a)

in which

A, B, D, X and n have the meanings given above are obtained by subjecting N-acylamino acid esters of the formula (II)

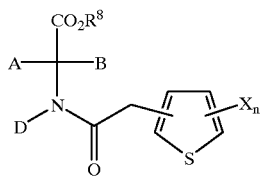
(II)

in which

A, B, D, X and n have the meanings given above, and $R^8$ represents alkyl, preferably $C_1$–$C_6$-alkyl, to intramolecular condensation in the presence of a diluent and in the presence of a base.

(B) It has furthermore been found that 3-thienyl-4-hydroxy-$\Delta^3$-dihydrofuranone derivatives of the formula (I-2-a)

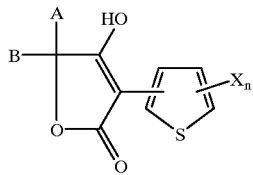
(I-2-a)

in which

A, B, X and n have the meanings given above are obtained by subjecting carboxylic esters of the formula (III)

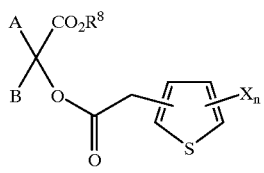
(III)

in which

A, B, X, $R^8$ and n have the meanings given above to intramolecular condensation in the presence of a diluent and in the presence of a base.

(C) It has additionally been found that 3-thienyl-4-hydroxy-$\Delta^3$-dihydrothiophenone derivatives of the formula (I-3-a)

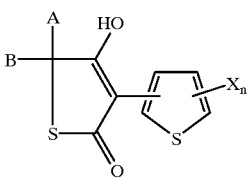
(I-3-a)

in which

A, B, X and n have the meanings given above are obtained by subjecting β-ketocarboxylic esters of the formula (IV)

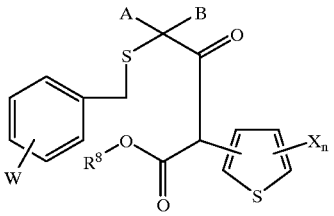
(IV)

in which

A, B, X, $R^8$ and n have the meanings given above, and

W represents hydrogen, halogen, alkyl, preferably $C_1$–$C_6$-alkyl, or alkoxy, preferably $C_1$–$C_8$-alkoxy, to intramolecular cyclization, optionally in the presence of a diluent and in the presence of an acid.

(D) 3-Hydroxy-4-thienyl-5-oxo-pyrazolines of the formula (I-4-a)

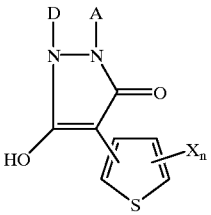
(I-4-a)

in which

A, D, X and n have the meanings given above, are obtained by reacting (α) halogenocarbonyl ketenes of the formula (V)

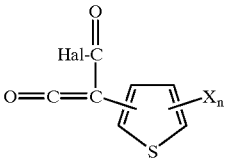
(V)

in which

X and n have the meanings given above, and

Hal represents halogen, especially chlorine or bromine or (β) malonic acid derivatives of the formula (VI)

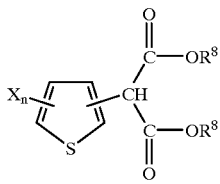
(VI)

in which

R⁸, X and n have the meanings given above,
with hydrazines of the formula (VII)

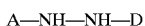 (VII)

in which

A and D have the meanings given above,
if desired in the presence of a diluent and if desired in the presence of a base.

(E) It has additionally been found that the novel 3-thienylpyrone derivatives of the formula (I-5-a)

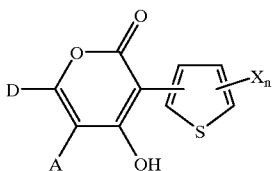
(I-5-a)

in which

A, D, X and n have the meanings given above are obtained by
reacting carbonyl compounds of the formula (VIII)

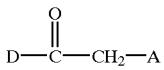 (VIII)

in which

A and D have the meanings given above
with ketene acid halides of the formula (V)

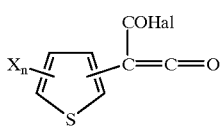
(V)

in which

X and n have the meanings given above, and
Hal represents halogen, preferably chlorine or bromine,
if desired in the presence of a diluent and if desired in the presence of an acid acceptor.

(F) It has additionally been found that the novel thienyl-1,3-thiazine derivatives of the formula (I-6-a)

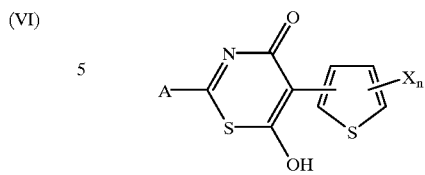
(I-6-a)

in which

A, X and n have the meanings given above
are obtained by reacting thioamides of the formula (IX)

 (IX)

in which

A has the meaning given above
with ketene acid halides of the formula (V)

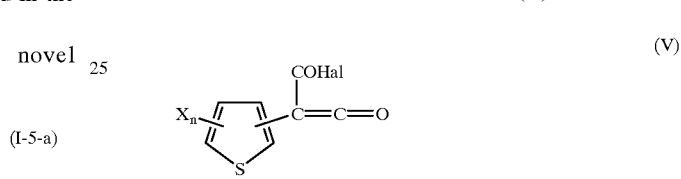
(V)

in which

Hal, X and n have the meanings given above,
if desired in the presence of a diluent and if desired in the presence of an acid acceptor.

(G) It has additionally been found that 2-thienyl-3-hydroxy-Δ²-cyclopenten-1-one derivatives of the formula (I-7-a)

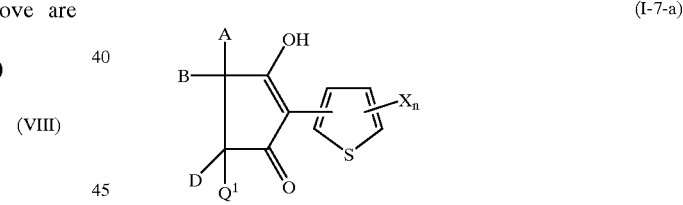
(I-7-a)

in which

A, B, D, Q¹, X and n have the meanings given above are obtained by
subjecting ketocarboxylic esters of the formula (X)

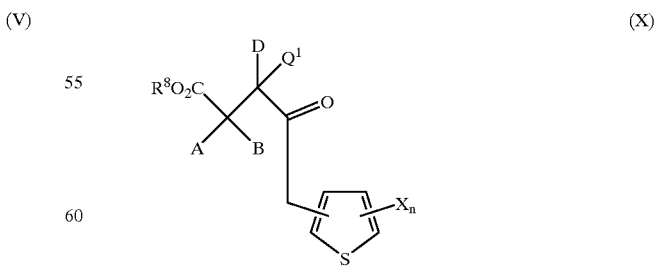
(X)

in which

A, B, D, R⁸, Q¹, X and n have the meanings given above to intramolecular cyclization, if desired in the presence of a diluent and in the presence of a base.

(H) It has additionally been found that 2-thienyl-3-hydroxy-$\Delta^2$-cyclohexen-1-one derivatives of the formula (I-8-a)

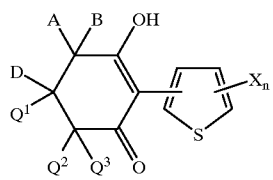
(I-8-a)

in which

A, B, D, $Q^1$, $Q^2$, $Q^3$, X and n have the meanings given above are obtained by
subjecting ketocarboxylic esters of the formula (XI)

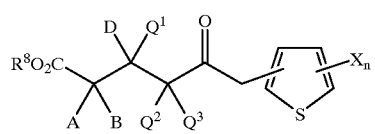
(XI)

in which

A, B, D, $Q^1$, $Q^2$, $Q^3$, $R^8$, X and n have the meanings given above to intramolecular cyclization, if desired in the presence of a diluent and in the presence of a base.

It has additionally been found
(I) that the compounds of the formulae (I-1-b) to (I-8-b) as shown above, in which A, B, D, $Q^1$, $Q^2$, $Q^3$, $R^1$, X and n have the meanings given above, are obtained by reacting compounds of the formulae (I-1-a) to (I-8-a) as shown above, in which A, B, D, $Q^1$, $Q^2$, $Q^3$, X and n have the meanings given above, in each case α) with acyl halides of the formula (XII)

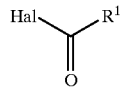
(XII)

in which $R^1$ has the meaning given above, and

Hal represents halogen, especially chlorine or bromine, or

β) with carboxylic anhydrides of the formula (XIII)

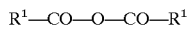
$R^1$—CO—O—CO—$R^1$ (XIII)

in which $R^1$ has the meaning given above,
if desired in the presence of a diluent and if desired in the presence of an acid-binding agent;
(J) that the compounds of the formulae (I-1-c) to (I-8-c) as shown above, in which A, B, D, $Q^1$, $Q^2$, $Q^3$, $R^2$, M, X and n have the meanings given above and L represents oxygen, are obtained by reacting compounds of the formulae (I-1-a) to (I-8-a) as shown above, in which A, B, D, $Q^1$, $Q^2$, $Q^3$, X and n have the meanings given above, in each case
with chloroformic esters or chloroformic thioesters of the formula (XIV)

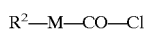
$R^2$—M—CO—Cl (XIV)

in which $R^2$ and M have the meanings given above,
if desired in the presence of a diluent and if desired in the presence of an acid-binding agent;
(K) that compounds of the formulae (I-1-c) to (I-8-c) as shown above, in which A, B, D, $Q^1$, $Q^2$, $Q^3$, $R^2$, M, X and n have the meanings given above and L represents sulfur, are obtained by reacting compounds of the formulae (I-1-a) to (I-8-a) as shown above, in which A, B, D, $Q^1$, $Q^2$, $Q^3$, X and n have the meanings given above, in each case α) with chloromonothioformic esters or chlorodithioformic esters of the formula (XV)

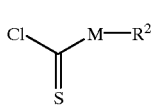
(XV)

in which

M and $R^2$ have the meanings given above,
if desired in the presence of a diluent and if desired in the presence of an acid-binding agent, or β) with carbon disulfide and then with alkyl halides of the formula (XVI)

$R^2$—Hal (XVI)

in which $R^2$ has the meaning given above, and

Hal represents chlorine, bromine or iodine,
if desired in the presence of a diluent and if desired in the presence of a base,
(L) that compounds of the formulae (I-1-d) to (I-8-d) as shown above, in which A, B, D, $Q^1$, $Q^2$, $Q^3$, $R^3$, X and n have the meanings given above, are obtained by reacting compounds of the formulae (I-1-a) to (I-8-a) as shown above, in which A, B, D, $Q^1$, $Q^2$, $Q^3$, X and n have the meanings given above, in each case
with sulfonyl chlorides of the formula (XVII)

$R^3$—SO$_2$—Cl (XVII)

in which $R^3$ has the meaning given above,
if desired in the presence of a diluent and if desired in the presence of an acid-binding agent,
(M) that compounds of the formulae (I-1-e) to (I-8-e) as shown above, in which A, B, D, $Q^1$, $Q^2$, $Q^3$, L, $R^4$, $R^5$, X and n have the meanings given above, are obtained by reacting compounds of the formulae (I-1-a) to (I-8-a) as shown above, in which A, B, D, $Q^1$, $Q^2$, $Q^3$, X and n have the meanings given above, in each case
with phosphorus compounds of the formula (XVIII)

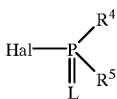
(XVIII)

in which

L, $R^4$ and $R^5$ have the meanings given above, and

Hal represents halogen, especially chlorine or bromine,
if desired in the presence of a diluent and if desired in the presence of an acid-binding agent,
(N) that compounds of the formulae (I-1-f) to (I-8-f) as shown above, in which A, B, D, $Q^1$, $Q^2$, $Q^3$, E, X and n have the meanings given above, are obtained by reacting compounds of the formulae (I-1-a) to (I-8-a), in which A, B, D, $Q^1$, $Q^2$, $Q^3$, X and n have the meanings given above, in each case
with metal compounds or amines of the formulae (XIX) or (XX)

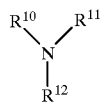

(XIX)

(XX)

in which
  Me represents a mono- or divalent metal, preferably an alkali metal or alkaline earth metal such as lithium, sodium, potassium, magnesium or calcium,
  t represents the number 1 or 2, and
  $R^{10}$, $R^{11}$ and $R^{12}$, independently of one another, represent hydrogen or alkyl, preferably $C_1$–$C_8$-alkyl,
if desired in the presence of a diluent,
(O) that compounds of the formulae (I-1-g) to (I-8-g) as shown above, in which A, B, D, $Q^1$, $Q^2$, $Q^3$, L, $R^6$, $R^7$, X and n have the meanings given above, are obtained by reacting compounds of the formulae (I-1-a) to (I-8-a) as shown above, in which A, B, D, $Q^1$, $Q^2$, $Q^3$, X and n have the meanings given above, in each case
α) with isocyanates or isothiocyanates of the formula (XXI)

  (XXI)

in which
  $R^6$ and L have the meanings given above
if desired in the presence of a diluent and if desired in the presence of a catalyst, or
β) with carbamoyl chlorides or thiocarbamoyl chlorides of the formula (XXII)

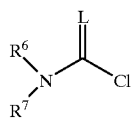

(XXII)

in which
  L, $R^6$ and $R^7$ have the meanings given above,
if desired in the presence of a diluent and if desired in the presence of an acid-binding agent.

It has additionally been found that the novel substituted thiophene derivatives of the formula (I) have a very good activity as pesticides, preferably as insecticides, acaricides, nematicides and herbicides, and as ectoparasiticides.

A general definition of the substituted thiophene derivatives according to the invention is given by the formula (I). Preferred substituents and/or ranges of the radicals listed in the formulae mentioned above and below are as follows:

X preferably represents halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, nitro or cyano or two substituents X, together with the carbon atoms to which they are attached, form a saturated or unsaturated 5- to 8-membered carbocyclic ring which is optionally substituted by halogen, $C_1$–$C_6$-alkyl, $C_1$–$C_6$-alkoxy, $C_1$–$C_6$-halogenoalkyl, $C_1$–$C_6$-halogenoalkoxy, nitro or cyano.

n preferably represents 1, 2 or 3.

Z preferably represents one of the groups

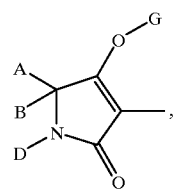  (1)

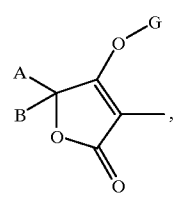  (2)

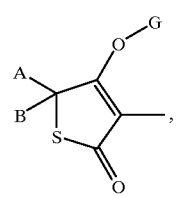  (3)

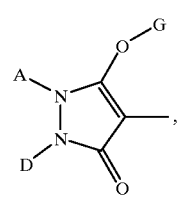  (4)

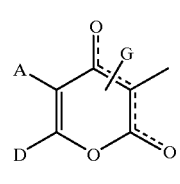  (5)

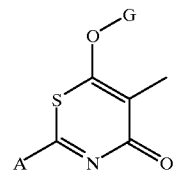  (6)

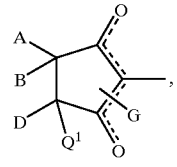  (7)

-continued (8)

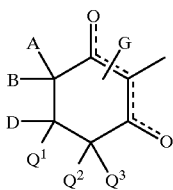

A preferably represents hydrogen or in each case optionally halogen-substituted $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl, $C_1$–$C_{10}$-alkylthio-$C_1$–$C_6$-alkyl, cycloalkyl having 3 to 8 ring atoms which is optionally substituted by $C_1$–$C_6$-alkyl, halogen or $C_1$–$C_6$-alkoxy and in which, optionally, one or two methylene groups which are not directly adjacent are replaced by oxygen and/or sulfur, or represents $C_6$- or $C_{10}$-aryl, hetaryl having 5 or 6 ring atoms and one to three heteroatoms from the series consisting of nitrogen, oxygen and sulfur, or $C_6$- or $C_{10}$-aryl-$C_1$–$C_6$-alkyl, each of which is optionally substituted by halogen, $C_1$–$C_6$-alkyl, $C_1$–$C_6$-halogenoalkyl, $C_1$–$C_6$-alkoxy or nitro.

B preferably represents hydrogen, $C_1$–$C_{12}$-alkyl or $C_1$–$C_8$-alkoxy-$C_1$–$C_6$-alkyl, or A, B and the carbon atom to which they are attached preferably represent a saturated or unsaturated $C_3$–$C_{10}$ spirocyclic system in which, optionally, one or two methylene groups which are not directly adjacent are replaced by oxygen and/or sulfur and which is optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom to which they are attached preferably represent a $C_3$–$C_6$ spirocyclic ring system which is substituted by an alkylenediyl group, optionally interrupted by one or two oxygen and/or sulfur atoms, or is substituted by an alkylenedioxy or by an alkylenedithio group, which, with the carbon atom to which it is attached, forms a further five- to eight-membered spirocyclic ring system, or A, B and the carbon atom to which they are attached preferably represent a $C_3$–$C_8$ spirocyclic ring system in which two substituents together represent a saturated or mono- or polyunsaturated 5- to 8-membered ring which is optionally substituted by $C_1$–$C_6$-alkyl, $C_1$–$C_6$-alkoxy or halogen and which optionally contains an oxygen or sulfur atom.

D preferably represents hydrogen, in each case optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl, $C_1$–$C_{10}$-alkylthio-$C_2$–$C_8$-alkyl, cycloalkyl having 3 to 8 ring atoms which is optionally substituted by halogen, $C_1$–$C_4$-alkyl, $C_1$–$C_4$-alkoxy or $C_1$–$C_4$-halogenoalkyl and in which, optionally, one or two methylene groups which are not directly adjacent are replaced by oxygen and/or sulfur, or represents phenyl, hetaryl having 5 or 6 ring atoms and one to three heteroatoms from the series consisting of nitrogen, oxygen and sulfur, or phenyl-$C_1$–$C_6$-alkyl, each of which is optionally substituted by halogen, $C_1$–$C_6$-alkyl, $C_1$–$C_6$-halogenoalkyl, $C_1$–$C_6$-alkoxy or nitro, or A and D preferably represent, together with the atoms to which they are attached, an alkanediyl or alkenediyl grouping of 3 to 6 carbon atoms which is optionally substituted from one to four times by identical or different substituents, in which a) optionally, one or two methylene groups which are not directly adjacent are replaced by oxygen and/or sulfur, and suitable substituents being:

halogen, hydroxyl, mercapto or in each case optionally halogen-substituted $C_1$–$C_{10}$-alkyl, $C_1$–$C_6$-alkoxy, $C_1$$C_6$-alkylthio, $C_3$–$C_7$-cycloalkyl, phenyl or benzyloxy;

or a further alkanediyl grouping of 3 to 6 carbon atoms which is optionally substituted by $C_1$–$C_6$-alkyl or in which, optionally, two adjacent substituents form, with the carbon atoms to which they are attached, a further saturated or unsaturated $C_5$–$C_6$-membered ring;

or which b) is optionally interrupted by one of the following groupings

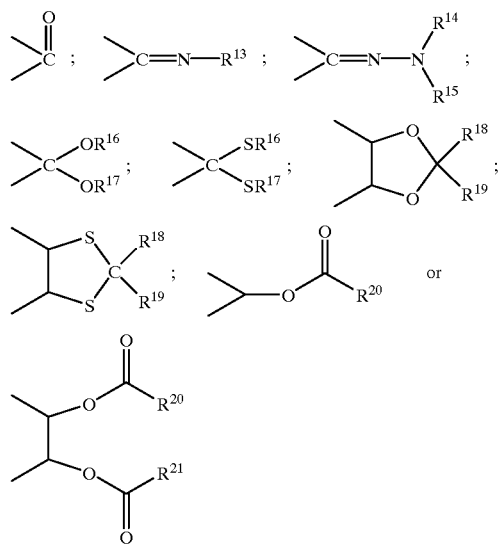

$Q^1$, $Q^2$ and $Q^3$, independently of one another, preferably represent hydrogen or optionally halogen-substituted $C_1$–$C_6$-alkyl, or B and $Q^1$ together preferably represent a $C_1$–$C_6$-alkanediyl grouping which is optionally substituted by halogen or $C_1$–$C_6$-alkyl.

G preferably represents hydrogen (a) or represents one of the groups

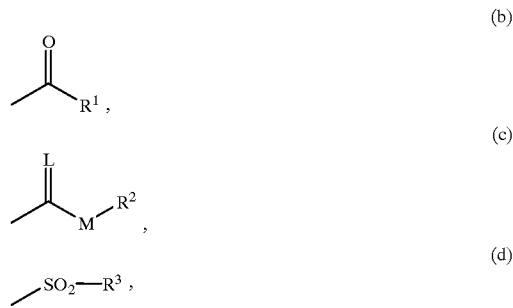

-continued

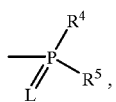
(e)

E or
(f)

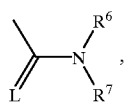
(g)

in which
- E represents a metal ion equivalent or an ammonium ion,
- L represents oxygen or sulfur, and
- M represents oxygen or sulfur.
- $R^1$ preferably represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl, or represents cycloalkyl having 3 to 8 ring atoms which is optionally substituted by halogen or $C_1$–$C_6$-alkyl and in which, optionally, one or two methylene groups which are not directly adjacent are replaced by oxygen and/or sulfur,
  - or represents phenyl which is optionally substituted by halogen, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulfonyl,
  - or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy,
  - or represents 5- or 6-membered hetaryl having one to three heteroatoms from the series consisting of nitrogen, oxygen and sulfur, which is optionally substituted by halogen or $C_1$–$C_6$-alkyl,
  - or represents phenoxy-$C_1$–$C_6$-alkyl which is optionally substituted by halogen or $C_1$–$C_6$-alkyl, or
  - represents 5- or 6-membered hetaryloxy-$C_1$–$C_6$-alkyl having one to three heteroatoms from the series consisting of nitrogen, oxygen and sulfur, which is optionally substituted by halogen, amino or $C_1$–$C_6$-alkyl.
- $R^2$ preferably represents in each case optionally halogen-substituted $C_1$–$C_{20}$-alkyl, $C_3$–$C_{20}$-alkenyl, $C_1$–$C_8$-alkoxy-$C_1$–$C_8$-alkyl or poly-$C_1$–$C_8$-alkoxy-$C_1$–$C_8$-alkyl,
  - or represents $C_3$–$C_8$-cycloalkyl which is optionally substituted by halogen, $C_1$–$C_4$-alkyl or $C_1$–$C_4$-alkoxy, or
  - represents phenyl or benzyl each of which is optionally substituted by halogen, nitro, $C_1$–$C_6$-alkyl, $C_1$–$C_6$-alkoxy or $C_1$–$C_6$-halogenoalkyl.
- $R^3$ preferably represents optionally halogen-substituted $C_1$–$C_8$-alkyl or represents benzyl or phenyl each of which is optionally substituted by halogen, $C_1$–$C_6$-alkyl, $C_1$–$C_6$-alkoxy, $C_1$–$C_3$-halogenoalkyl, $C_1$–$C_3$-halogenoalkoxy, nitro or cyano.
- $R^4$ and $R^5$ preferably represent, independently of one another, optionally halogen-substituted $C_1$–$C_8$-alkyl, $C_1$–$C_8$-alkoxy, $C_1$–$C_8$-alkylamino, di-($C_1$–$C_8$-alkyl)-amino, $C_1$–$C_8$-alkylthio, $C_2$–$C_8$-alkenylthio, $C_3$–$C_7$-cycloalkylthio, or represent phenyl, phenoxy or phenylthio each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

- $R^6$ and $R^7$, independently of one another, preferably represent hydrogen, in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, phenyl which is optionally substituted by halogen, $C_1$–$C_8$-halogenoalkyl, $C_1$–$C_8$-alkyl or $C_1$–$C_8$-alkoxy, benzyl which is optionally substituted by halogen, $C_1$–$C_8$-alkyl, $C_1$–$C_8$-halogenoalkyl or $C_1$–$C_8$-alkoxy, or together represent $C_3$–$C_6$-alkanediyl in which, optionally, one methylene group is replaced by oxygen or sulfur.

- $R^{13}$ preferably represents hydrogen, in each case optionally halogen-substituted $C_1$–$C_8$-alkyl, $C_1$–$C_8$-alkoxy or $C_3$–$C_8$-cycloalkyl, or represents phenyl or benzyl each of which is optionally substituted by halogen, $C_1$–$C_6$-alkyl, $C_1$–$C_6$-alkoxy, $C_1$–$C_3$-halogenoalkyl, $C_1$–$C_3$-halogenoalkoxy, nitro or cyano.

- $R^{14}$ and $R^{15}$ preferably represent, independently of one another, hydrogen, $C_1$–$C_8$-alkyl, $C_1$–$C_8$-halogenoalkyl, $C_3$–$C_6$-cycloalkyl, or represent phenyl or benzyl each of which is optionally substituted by halogen, $C_1$–$C_6$-alkyl, $C_1$–$C_6$-alkoxy, $C_1$–$C_3$-halogenoalkyl, $C_1$–$C_3$-halogenoalkoxy, cyano or nitro, or together represent an optionally $C_1$–$C_4$-alkyl-substituted $C_4$–$C_6$-alkanediyl group.

- $R^{16}$ and $R^{17}$ are identical or different and preferably represent $C_1$–$C_6$-alkyl, or

- $R^{16}$ and $R^{17}$ together preferably represent a $C_2$–$C_4$-alkanediyl radical which is optionally substituted by $C_1$–$C_6$-alkyl or by phenyl which is optionally substituted by halogen, $C_1$–$C_4$-alkyl, $C_1$–$C_4$-halogenoalkyl, $C_1$–$C_4$-alkoxy, $C_1$–$C_4$-halogenoalkoxy, nitro or cyano.

- $R^{18}$ and $R^{19}$, independently of one another, preferably represent hydrogen, optionally halogen-substituted $C_1$–$C_8$-alkyl, or phenyl which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

- $R^{20}$ and $R^{21}$, independently of one another, preferably represent $C_1$–$C_{10}$-alkyl, $C_3$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)-amino or di-($C_3$–$C_{10}$-alkenyl)-amino.

- X particularly preferably represents fluorine, chlorine, bromine, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, nitro or cyano
  - or two substituents X, form, together with the carbon atoms to which they are attached, an unsaturated 5- to 7-membered carbocyclic ring which is optionally substituted by fluorine, chlorine, bromine, $C_1$–$C_4$-alkyl, $C_1$–$C_4$-alkoxy, $C_1$–$C_4$-halogenoalkyl, $C_1$–$C_4$-halogenoalkoxy, nitro or cyano.

- n particularly preferably represents 1, 2 or 3.

Z particularly preferably represents one of the groups (1) 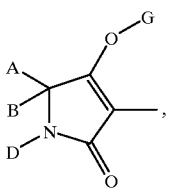

(2) 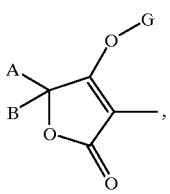

(3) 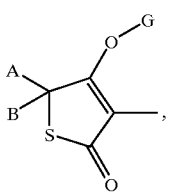

(4) 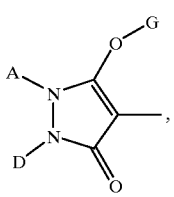

(5) 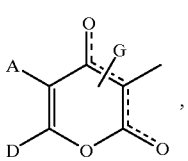

(6) 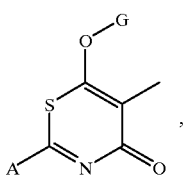

(7) 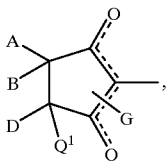

(8) 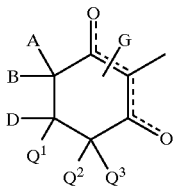

A particularly preferably represents hydrogen, in each case optionally fluorine- or chlorine-substituted $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl, $C_1$–$C_8$-alkylthio-$C_1$–$C_6$-alkyl, cycloalkyl having 3 to 7 ring atoms which is optionally substituted by $C_1$–$C_4$-alkyl, $C_1$–$C_4$-alkoxy, fluorine or chlorine and in which, optionally, one or two methylene groups which are not directly adjacent are replaced by oxygen and/or sulfur, or represents phenyl, furanyl, pyridyl, imidazolyl, triazolyl, pyrazolyl, indolyl, thiazolyl, thienyl or phenyl-$C_1$–$C_4$-alkyl each of which is optionally substituted by fluorine, chlorine, bromine, $C_1$–$C_4$-alkyl, $C_1$–$C_4$-halogenoalkyl, $C_1$–$C_4$-alkoxy or nitro.

B particularly preferably represents hydrogen, $C_1$–$C_{10}$-alkyl or $C_1$–$C_6$-alkoxy-$C_1$–$C_4$-alkyl, or A, B and the carbon atom to which they are attached particularly preferably represent a saturated or unsaturated $C_3$–$C_9$ spirocyclic ring system in which, optionally, one or two methylene groups which are not directly adjacent are replaced by oxygen and/or sulfur and which is optionally substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom to which they are attached particularly preferably represent a $C_3$–$C_6$ spirocyclic ring system which is substituted by an alkylenediyl group, which is optionally interrupted by one or two oxygen or sulfur atoms or by an alkylenedioxy group or by an alkylenedithio group, which, with the carbon atom to which it is attached, forms a further five- to seven-membered spirocyclic ring system, or A, B and the carbon atom to which they are attached particularly preferably represent a $C_3$–$C_6$ spirocyclic ring system in which two substituents together represent a saturated or mono- or polyunsaturated 5- or 6-membered ring which is optionally substituted by $C_1$–$C_5$-alkyl, $C_1$–$C_5$-alkoxy, fluorine, chlorine or bromine and which optionally contains an oxygen or sulfur atom.

D particularly preferably represents hydrogen, in each case optionally fluorine- or chlorine-substituted $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl, $C_1$–$C_8$-alkylthio-$C_2$–$C_6$-alkyl, cycloalkyl having 3 to 7 ring atoms which is optionally substituted by $C_1$–$C_4$-alkyl, $C_1$–$C_4$-alkoxy or $C_1$–$C_2$-halogenoalkyl and in which, optionally, one or two methylene groups which are not directly adjacent are replaced by oxygen and/or sulfur, or represents phenyl, pyridyl, thienyl, furanyl, thiazolyl, pyrimidyl, pyrazolyl or phenyl-$C_1$–$C_4$-alkyl, each of which is optionally substituted by halogen, $C_1$–$C_4$-alkyl, $C_1$–$C_4$-halogenoalkyl, $C_1$–$C_4$-alkoxy or nitro, or A and D particularly preferably represent, together with the atoms to which they are attached, a $C_3$–$C_5$-alkanediyl or $C_3$–$C_5$-alkenediyl grouping in which a) optionally, one methylene group is replaced by oxygen or sulfur and which is optionally substituted by fluorine, chlorine, hydroxyl or mercapto or by in each case optionally fluorine- or chlorine-substituted $C_1$–$C_6$-alkyl, $C_1$–$C_4$-alkoxy, $C_1$–$C_4$-alkylthio, $C_3$–$C_6$-cycloalkyl, phenyl or benzyl;

or which b) is optionally interrupted by one of the following groupings

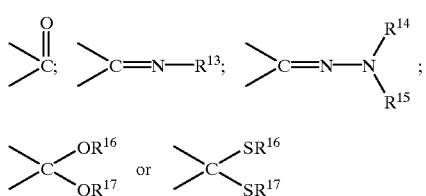
or in which A and D, in the case of compounds of the formula (I-1), together with the atoms to which they are attached, represent one of the groups AD-1 to AD-20.
AD-1
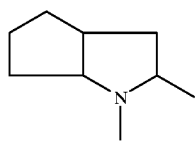
AD-2
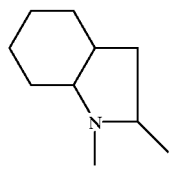
AD-3
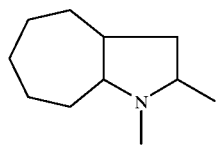
AD-4
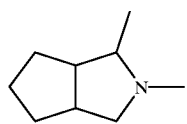
AD-5
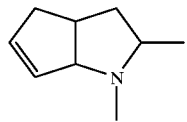
AD-6
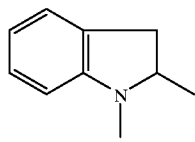
AD-7
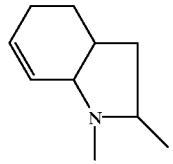
AD-8
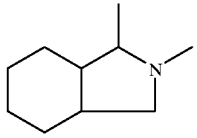
AD-9
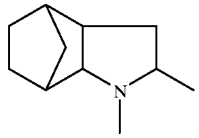
AD-10
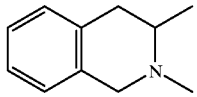
AD-11
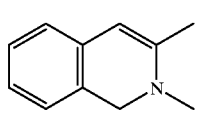
AD-12
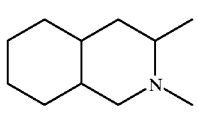
AD-13
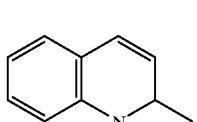
AD-14
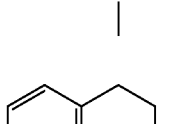
AD-15
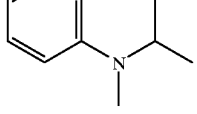
AD-16
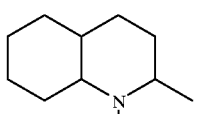
AD-17
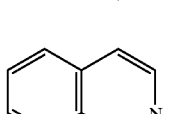

-continued

AD-18

AD-19

AD-20

$Q^1$, $Q^2$ and $Q^3$, independently of one another, particularly preferably represent hydrogen or optionally fluorine- or chlorine-substituted $C_1$–$C_4$-alkyl, or B and $Q^1$ particularly preferably represent a $C_1$–$C_4$-alkanediyl grouping which is optionally substituted by fluorine, chlorine or $C_1$–$C_4$-alkyl.

G particularly preferably represents hydrogen (a) or represents one of the groups (b)

$\overset{O}{\underset{}{\overset{\|}{\text{—C—}}}}R^1$, (c)

$\overset{L}{\underset{M}{\overset{\|}{\text{—C—}}}}R^2$, (d)

—SO$_2$—R$^3$, (e)

$\overset{R^4}{\underset{L}{\overset{\|}{\text{—P—}}}}R^5$, (f)

E or (g)

$\overset{R^6}{\underset{L}{\overset{\|}{\text{—C—N}}}}R^7$,

E represents a metal ion equivalent or an ammonium ion,
L represents oxygen or sulfur, and
M represents oxygen or sulfur.

$R^1$ particularly preferably represents in each case optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, poly-$C_1$–$C_6$-alkoxy-$C_1$–$C_6$-alkyl, or cycloalkyl having 3 to 7 ring atoms which is optionally substituted by fluorine, chlorine or $C_1$–$C_5$-alkyl and in which, optionally, one or two methylene groups which are not directly adjacent are replaced by oxygen and/or sulfur, or represents phenyl which is optionally substituted by fluorine, chlorine, bromine, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulfonyl, or represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents pyrazolyl, thiazolyl, pyridyl, pyrimidyl, furanyl or thienyl, each of which is optionally substituted by fluorine, chlorine, bromine or $C_1$–$C_4$-alkyl, or represents phenoxy-$C_1$–$C_5$-alkyl which is optionally substituted by fluorine, chlorine, bromine or $C_1$–$C_4$-alkyl, or represents pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino or $C_1$–$C_4$-alkyl.

$R^2$ particularly preferably represents in each case optionally fluorine- or chlorine-substituted $C_1$–$C_{16}$-alkyl, $C_3$–$C_{16}$-alkenyl, $C_1$–$C_6$-alkoxy-$C_1$–$C_6$-alkyl or poly-$C_1$–$C_6$-alkoxy-$C_1$–$C_6$-alkyl, or represents $C_3$–$C_7$-cycloalkyl which is optionally substituted by fluorine, chlorine, $C_1$–$C_3$-alkyl or $C_1$–$C_3$-alkoxy, or represents phenyl or benzyl, each of which is optionally substituted by fluorine, chlorine, bromine, nitro, $C_1$–$C_4$-alkyl, $C_1$–$C_3$-alkoxy or $C_1$–$C_3$-halogenoalkyl.

$R^3$ particularly preferably represents optionally fluorine- or chlorine-substituted $C_1$–$C_6$-alkyl or represents benzyl or phenyl each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

$R^4$ and $R^5$ particularly preferably represent, independently of one another, in each case optionally halogen-substituted $C_1$–$C_6$-alkyl, $C_1$–$C_6$-alkoxy, $C_1$–$C_6$-alkylamino, di-($C_1$–$C_6$-alkyl)-amino, $C_1$–$C_6$-alkylthio, $C_3$–$C_4$-alkenylthio, $C_3$–$C_6$-cycloalkylthio, or represent phenyl, phenoxy or phenylthio each of which is optionally substituted by fluorine, chlorine, bromine, nitro, cyano, $C_1$–$C_3$-alkoxy, $C_1$–$C_3$-halogeno-alkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$, independently of one another, particularly preferably represent hydrogen, in each case optionally fluorine-, chlorine- or bromine-substituted $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, phenyl which is optionally substituted by fluorine, chlorine, bromine, $C_1$–$C_5$-halogenoalkyl, $C_1$–$C_5$-alkyl or $C_1$–$C_5$-alkoxy, benzyl which is optionally substituted by fluorine, chlorine, bromine, $C_1$–$C_5$-alkyl, $C_1$–$C_5$-halogenoalkyl or $C_1$–$C_5$-alkoxy, or together represent $C_3$–$C_6$-alkanediyl in which, optionally, one methylene group is replaced by oxygen or sulfur.

$R^{13}$ particularly preferably represents hydrogen, in each case optionally fluorine- or chlorine-substituted $C_1$–$C_6$-alkyl, $C_1$–$C_6$-alkoxy or $C_3$–$C_7$-cycloalkyl, or represents phenyl or benzyl each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

$R^{14}$ and $R^{15}$ particularly preferably represent, independently of one another, hydrogen, $C_1$–$C_6$-alkyl, $C_1$–$C_6$-halogenoalkyl, $C_3$–$C_6$-cycloalkyl, or represent phenyl or benzyl each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, or together represent an optionally $C_1$–$C_3$-alkyl-substituted $C_4$–$C_5$-alkanediyl group.

$R^{16}$ and $R^{17}$ are identical or different and particularly preferably represent $C_1$–$C_4$-alkyl, or $R^{16}$ and $R^{17}$ together particularly preferably, represent a $C_2$–$C_3$-alkanediyl radical which is optionally substituted by $C_1$–$C_4$-alkyl or by phenyl which is optionally substituted by $C_1$–$C_2$-alkyl, $C_1$–$C_2$-halogenoalkyl, $C_1$–$C_2$-alkoxy, $C_1$–$C_2$-halogenoalkoxy, nitro or cyano.

X very particularly preferably represents flourine, chlorine, bromine, methyl, ethyl, propyl, isopropyl, butyl, isobutyl, tert-butyl, trifluoromethyl, trifluoromethoxy, nitro or cyano or two substituents X form, together with the carbon atoms to which they are attached, an unsaturated 6-membered carbocyclic ring which is optionally substituted by fluorine, chlorine, bromine, methyl, methoxy, trifluoromethyl, trifluoromethoxy, nitro or cyano.

n very particularly preferably represents 1, 2 or 3.

Z very particularly preferably represents one of the groups

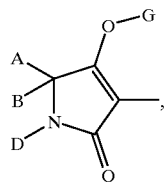

(1)

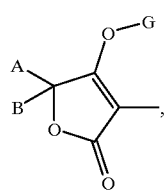

(2)

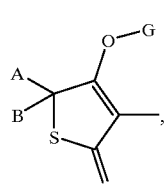

(3)

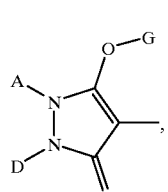

(4)

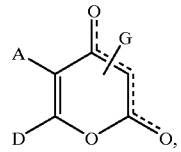

(5)

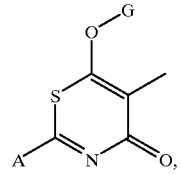

(6)

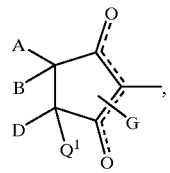

(7)

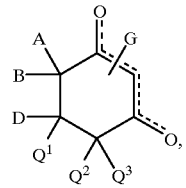

(8)

A very particularly preferably represents hydrogen, in each case optionally fluorine- or chlorine-substituted $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl, $C_1$–$C_6$-alkylthio-$C_1$–$C_4$-alkyl, cycloalkyl having 3 to 6 ring atoms in which, optionally, one methylene group is replaced by oxygen or sulfur, or represents phenyl, furanyl, pyridyl, imidazolyl, pyrazolyl, triazolyl, indolyl, thiazolyl, thienyl or benzyl each of which is optionally substituted by fluorine, chlorine, bromine, methyl, ethyl, propyl, isopropyl, methoxy, ethoxy, trifluoromethyl or nitro.

B very particularly preferably represents hydrogen, $C_1$–$C_8$-alkyl or $C_1$–$C_4$-alkoxy-$C_1$–$C_2$-alkyl, or A, B and the carbon atom to which they are attached very particularly preferably represent a saturated or unsaturated $C_3$–$C_8$ spirocyclic ring system in which, optionally, one methylene group is replaced by oxygen or sulfur, and which is optionally mono- or polysubstituted by methyl, ethyl, propyl, isopropyl, butyl, isobutyl, sec-butyl, tert-butyl, cyclohexyl, trifluoromethyl, methoxy, ethoxy, propoxy, isopropoxy, butoxy, isobutoxy, sec-butoxy, tert-butoxy, methylthio, ethylthio, fluorine, chlorine or phenyl, or A, B and the carbon atom to which they are attached very particularly preferably represent a $C_3$–$C_6$ spirocyclic ring system which is substituted by an alkylenediyl group, which is optionally interrupted by an oxygen or sulfur atom or by an alkylenedioxy group which, with the carbon atom to which it is attached, forms a further five- to seven-membered spirocyclic ring system, or A, B and the carbon atom to which they are attached very particularly preferably represent a $C_3$–$C_6$ spirocyclic ring system in which two substituents together represent a saturated or mono- to triunsaturated five- or six-membered ring which optionally contains an oxygen or sulfur atom.

D very particularly preferably represents hydrogen, in each case optionally fluorine- or chlorine-substituted $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl, $C_3$–$C_6$-cycloalkyl, in which, optionally, one methylene group is replaced by oxygen or sulfur, or represents phenyl, benzyl, pyridyl, thienyl, furanyl or thiazolyl each of which is optionally substituted by fluorine, chlorine, bromine, methyl, ethyl, propyl, isopropyl, methoxy, ethoxy, trifluoromethyl or nitro, or A and D very particularly preferably represent, together with the atoms to which they are attached, a $C_3$–$C_5$-alkanediyl or $C_3$–$C_5$-alkenediyl grouping in which, optionally, one methylene group is replaced by oxygen or sulfur and which is optionally substituted by fluorine, chlorine, hydroxyl or mercapto or by in each case optionally fluorine- or chlorine-substituted $C_1$–$C_6$-alkyl, $C_1$–$C_4$-alkoxy, $C_1$–$C_4$-alkylthio, $C_3$–$C_6$-cycloalkyl, phenyl or benzyloxy, or, in the case of compounds of the formula (I-1), represent one of the following groupings

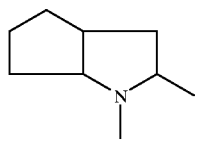

AD-1

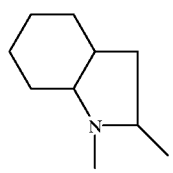

AD-2

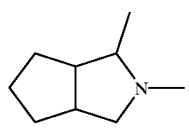

AD-4

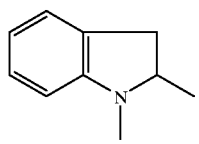

AD-6

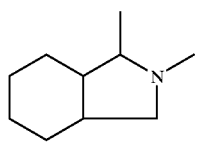

AD-8

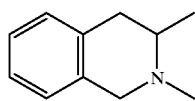

AD-10

-continued

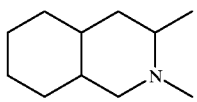

AD-12

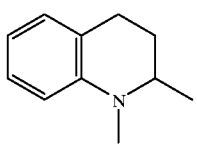

AD-14

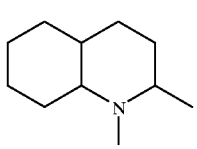

AD-15

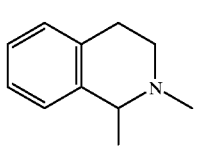

AD-17

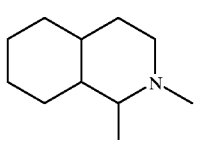

AD-18

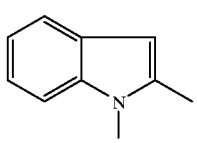

AD-20

$Q^1$, $Q^2$ and $Q^3$, independently of one another, very particularly preferably represent hydrogen, methyl or ethyl, or B and $Q^1$ together very particularly preferably represent a $C_1$–$C_4$-alkanediyl grouping which is optionally substituted by fluorine, chlorine methyl or ethyl.

G very particularly preferably represents hydrogen (a) or represents one of the groups

(b)

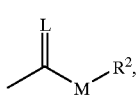

(c)

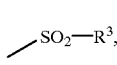

(d)

(e)

-continued (f)

E or (g)

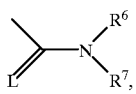

E represents a metal ion equivalent or an ammonium ion,
L represents oxygen or sulfur, and
M represents oxygen or sulfur.

$R^1$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or $C_3$–$C_6$-cycloalkyl which is optionally substituted by fluorine, chlorine, methyl, ethyl, propyl, isopropyl, butyl, isobutyl or tert-butyl and in which, optionally, one or two methylene groups which are not directly adjacent are replaced by oxygen and/or sulfur,
or represents phenyl which is optionally substituted by fluorine, chlorine, bromine, methyl, ethyl, propyl, isopropyl, methoxy, ethoxy, trifluoromethyl, trifluoromethoxy, methylthio, ethylthio, methylsulfonyl, ethylsulfonyl or nitro,
or represents benzyl which is optionally substituted by fluorine, chlorine, bromine, methyl, ethyl, propyl, isopropyl, methoxy, ethoxy, trifluoroethyl or trifluoromethoxy,
or represents furanyl, thienyl, pyridyl, pyrimidyl, thiazolyl or pyrazolyl each of which is optionally substituted by fluorine, chlorine, bromine, methyl or ethyl,
or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl.

$R^2$ very particularly preferably represents in each case optionally fluorine- or chlorine-substituted $C_1$–$C_{14}$-alkyl, $C_3$–$C_{14}$-alkenyl, $C_1$–$C_4$-alkoxy-$C_1$–$C_6$-alkyl or poly-$C_1$–$C_4$-alkoxy-$C_1$–$C_6$-alkyl,
or represents $C_3$–$C_6$-cycloalkyl which is optionally substituted by fluorine, chlorine, methyl, ethyl, propyl, isopropyl or methoxy,
or represents phenyl or benzyl, each of which is optionally substituted by fluorine, chlorine, nitro, methyl, ethyl, propyl, isopropyl, methoxy, ethoxy or trifluoromethyl.

$R^3$ very particularly preferably represents optionally fluorine- or chlorine-substituted $C_1$–$C_4$-alkyl or represents phenyl or benzyl each of which is optionally substituted by fluorine, chlorine, bromine, methyl, methoxy, trifluoromethyl, trifluoromethoxy, nitro or cyano.

$R^4$ and $R^5$ very particularly preferably represent, independently of one another, in each case optionally fluorine- or chlorine-substituted $C_1$–$C_4$-alkyl, $C_1$–$C_4$-alkoxy, $C_1$–$C_4$-alkylamino, di-($C_1$–$C_4$-alkyl)-amino, $C_1$–$C_4$-alkylthio or represent phenyl, phenoxy or phenylthio each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl.

$R^6$ and $R^7$, independently of one another, very particularly preferably represent hydrogen, in each case optionally fluorine-, chlorine- or bromine-substituted $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, phenyl which is optionally substituted by fluorine, chlorine, bromine, $C_1$–$C_4$-halogenoalkyl, $C_1$–$C_4$-alkyl or $C_1$–$C_4$-alkoxy, or represents benzyl which is optionally substituted by fluorine, chlorine, bromine $C_1$–$C_4$-alkyl, $C_1$–$C_4$-halogenoalkyl or $C_1$–$C_4$-alkoxy, or together represent $C_4$–$C_6$-alkanediyl in which, optionally, one methylene group is replaced by oxygen or sulfur.

For n>1, the radicals X may be identical or different.

The definitions or explanations of radicals given above, whether general or in ranges of preference, may be combined at will with one another, which thus includes combinations between the respective ranges and ranges of preference. They apply correspondingly to the end products and to the precursors and intermediates.

Compounds of the formula (I) which are preferred according to the invention are those in which there is a combination of the definitions given above as being preferred (preferably).

Compounds of the formula (I) which are particularly preferred in accordance with the invention are those in which there is a combination of the definitions given above as being particularly preferable (particularly preferably).

Compounds of the formula (I) which are very particularly preferred in accordance with the invention are those in which there is a combination of the definitions given above as being very particularly preferred (very particularly preferably).

Saturated or unsaturated hydrocarbon radicals may where possible alone or in conjunction with heteroatoms such as, for example, in alkoxy, each be straight-chain or branched.

If, in accordance with process (A), ethyl N-[3-(2-chloro)-thienylacetyl]-1-amino-4-ethyl-cyclohexane-carboxylate is used as starting material, then the course of the process according to the invention can be represented by the following equation:

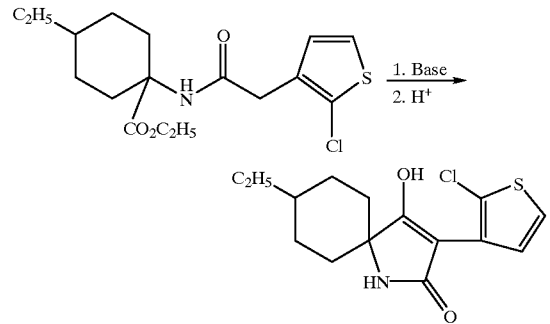

If, in accordance with process (B), ethyl O-[2-(3-methyl)-thienylacetyl]-hydroxyacetate is used, then the course of the process according to the invention can be represented by the following equation:

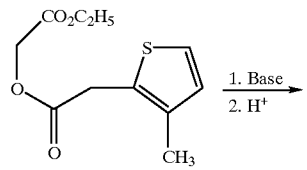

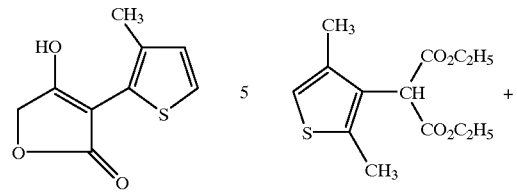

If, in accordance with process (C), ethyl 2-[2-(3,5-dichloro)-thienyl]-4-(4-methoxy)-benzylmercapto-4-methyl-3-oxo-valerate is used, then the course of the process according to the invention can be represented by the following equation:

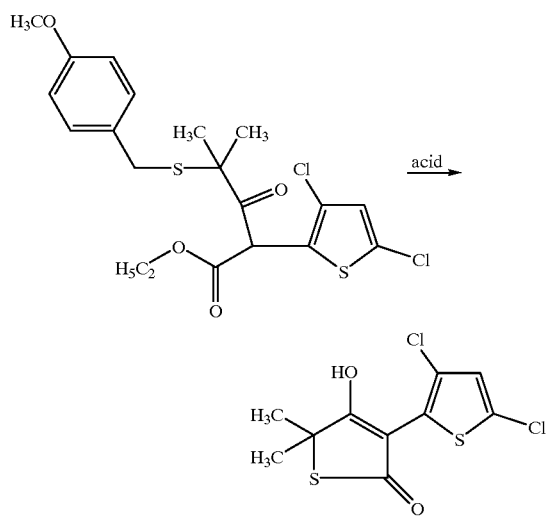

If, for example, in accordance with process (D-α), (chlorocarbonyl)-3-(2-methyl)-thienylketene and 1,2-diazacyclopentane are used as starting compounds, then the course of the process according to the invention can be represented by the following equation:

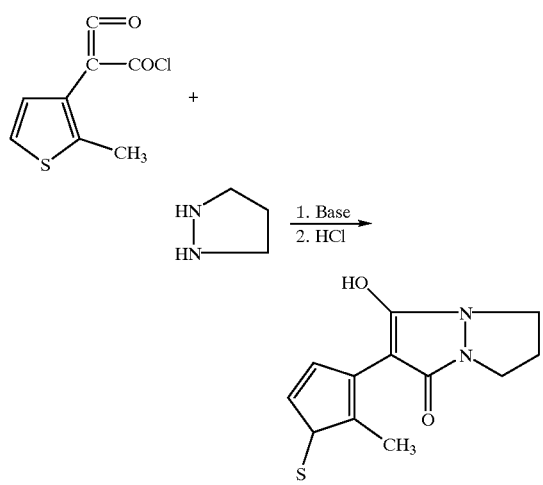

If, for example, in accordance with process (D-β), diethyl 3-(2,4-dimethyl)-thienylmalonate and 1,2-diazacyclopentane are used as starting compounds, then the course of the process according to the invention can be represented by the following equation:

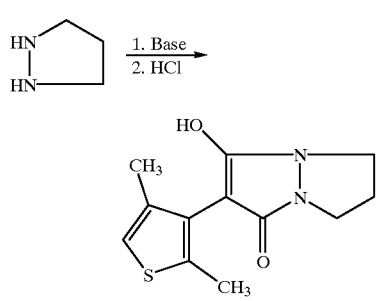

If, for example, in accordance with process (E), (chlorocarbonyl)-2-(3-methyl)-thienylketene and acetone are used as starting compounds, then the course of the process according to the invention can be represented by the following equation:

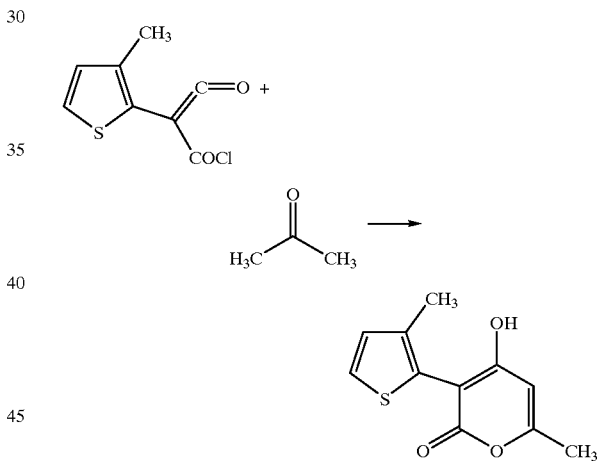

If, for example, in accordance with process (F), (chlorocarbonyl)-2-(3-chloro)-thienylketene and thiobenzamide are used as starting compounds, then the course of the process according to the invention can be represented by the following equation:

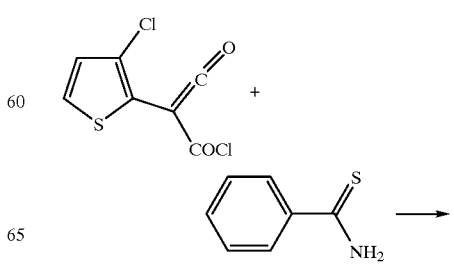

-continued

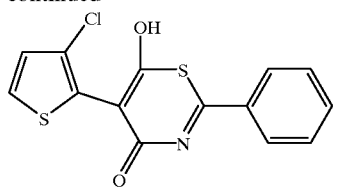

If, in accordance with process (G), ethyl 5-[2-(3-methyl-5-chloro)-thienyl]-2,2-dimethyl-4-oxo-valerate is used, then the course of the process according to the invention can be represented by the following equation:

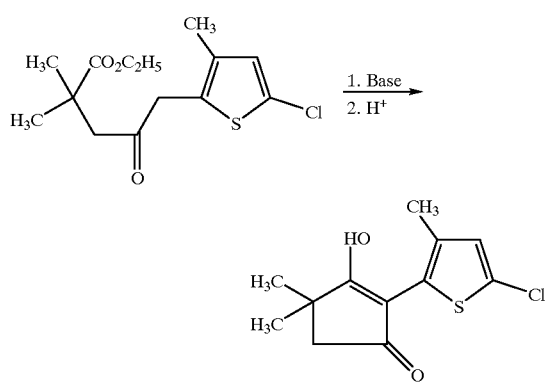

If, in accordance with process (H), ethyl 6-[3-(2,5-dichloro)-thienyl]-5-oxo-caproate is used, then the course of the process according to the invention can be represented by the following equation:

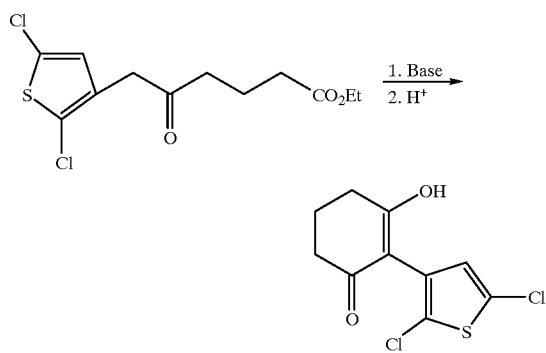

If, in accordance with process ($I_\alpha$), 3-[2-(3-methyl)thienyl]-5,5-dimethylpyrrolidine-2,4-dione and pivaloyl chloride are used as starting materials, then the course of the process according to the invention can be represented by the following equation:

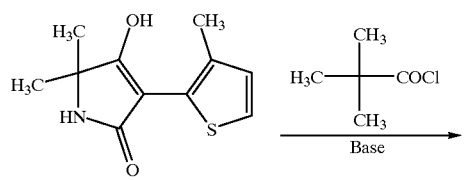

-continued

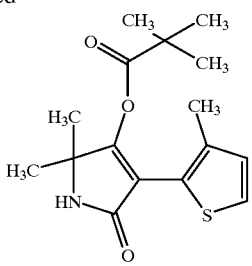

If, in accordance with process (I) (variant β), 3-[3-(2,5-dichloro)-thienyl]-4-hydroxy-5-phenyl-$\Delta^3$-dihydrofuran-2-one and acetic anhydride are used as starting compounds, then the course of the process according to the invention can be represented by the following equation:

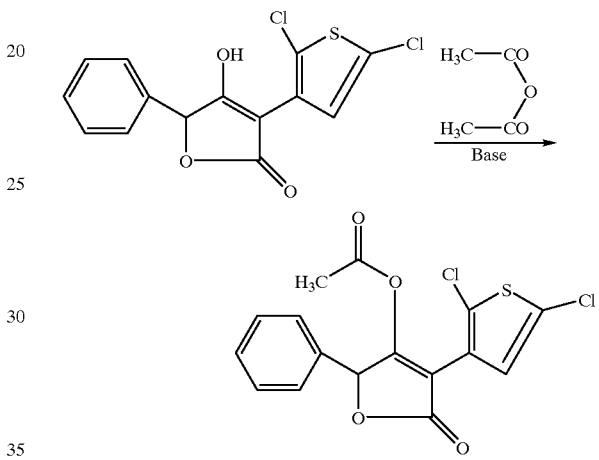

If, in accordance with process (J), 8-[2-(3-chloro)-thienyl]-1,6-diaza-bicyclo-[4.3.0$^{1,6}$]-nonane-7,9-dione and ethoxy-ethyl chloroformate are used as starting compounds, then the course of the process according to the invention can be represented by the following equation:

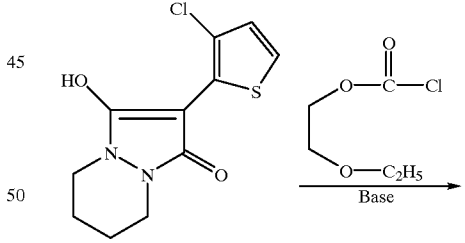

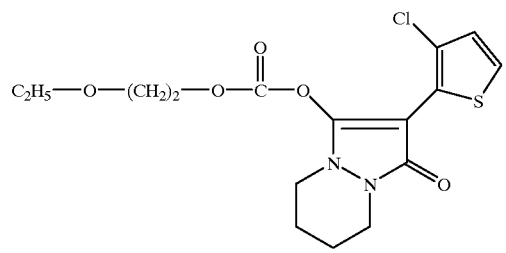

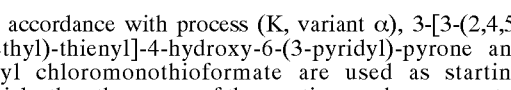

If, in accordance with process (K, variant α), 3-[3-(2,4,5-trimethyl)-thienyl]-4-hydroxy-6-(3-pyridyl)-pyrone and methyl chloromonothioformate are used as starting materials, then the course of the reaction can be represented as follows:

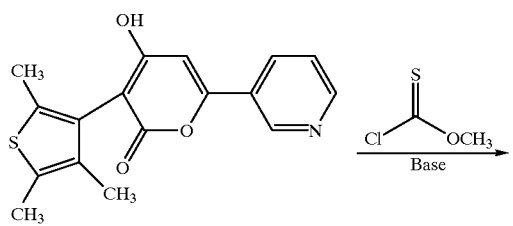

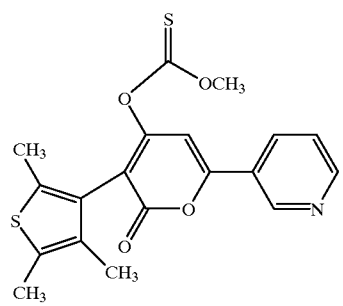

If, in accordance with process (K, variant β), 5-[2-(3,4-dimethyl)-thienyl]-6-hydroxy-2-(4-chlorophenyl)-thiazin-4-one, carbon disulfide and methyl iodide are used as starting components, then the course of the reaction can be represented as follows:

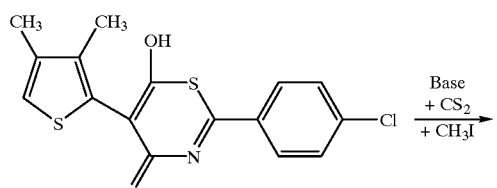

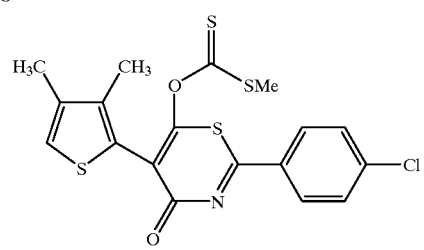

If, in accordance with process (L), 2-[3-(2-methyl)-thienyl]-3-hydroxy-4,4-(3-methoxy)-pentamethylene-Δ²-cyclopentenone and methanesulfonyl chloride are used as starting products, then the course of the reaction can be represented by the following equation:

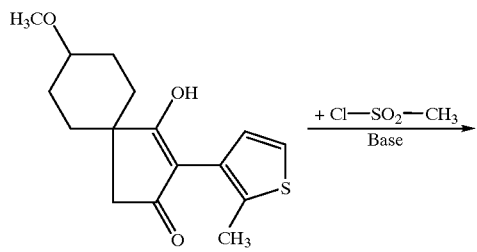

-continued

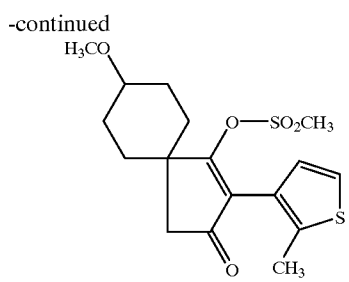

If, in accordance with process (M), 2-[3-(2-chloro)-thienyl]-3-hydroxy-4,4-dimethyl-Δ²-cylcohexanone and methanethio-phosphonyl chloride 2,2,2-trifluoroethyl ester are used as starting materials, then the course of the reaction can be represented by the following equation:

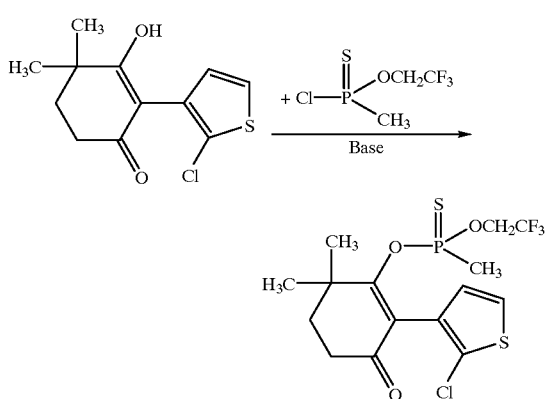

If, in accordance with process (N), 3-[2-(3,4-dimethyl)-thienyl]-5-cyclopropyl-5-methyl-pyrrolidine-2,4-dione and NaOH are used as components, then the course of the process according to the invention can be represented by the following equation:

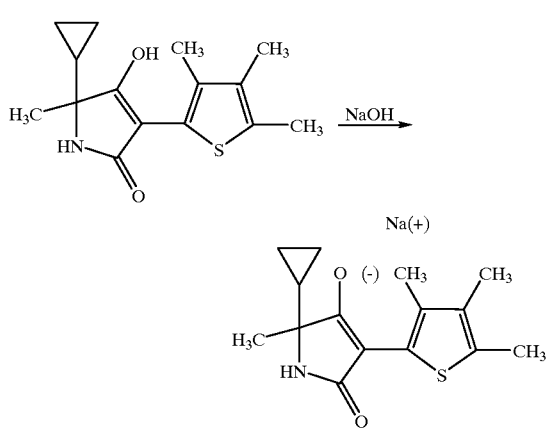

If, in accordance with process (O; variant α), 3-[2-(3,4,5-trichloro)-thienyl]-4-hydroxy-5-tetramethylene-Δ³-dihydrofuran-2-one and ethyl isocyanate are used as starting materials, then the course of the reaction can be represented by the following equation:

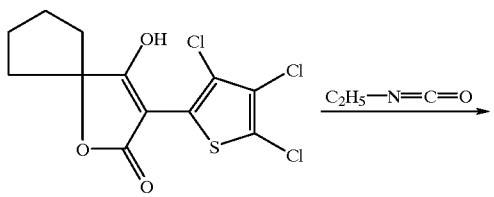 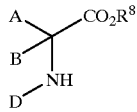

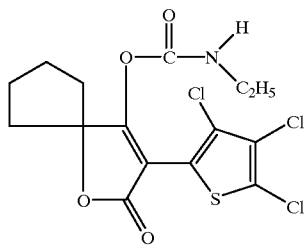 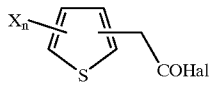

in which

A, B, $R^8$ and D have the meanings given above with thienylacetyl halides of formula (XXIV)

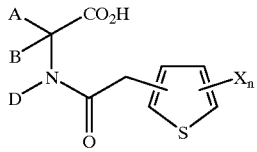

in which

X and n have the meanings given above, and

Hal represents chlorine or bromine
(Chem. Reviews 52, 237–416 (1953); Bhattacharya, Indian J. Chem. 6, 341–5, 1968)

or by esterifying acylamino acids of the formula (XXV)

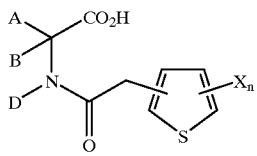

If, in accordance with process (O; variant β), 3-[3-(2-methyl)-thienyl]-5-methyl-pyrrolidine-2,4-dione and dimethylcarbamoyl chloride are used as starting materials, then the course of the reaction can be represented by the following equation:

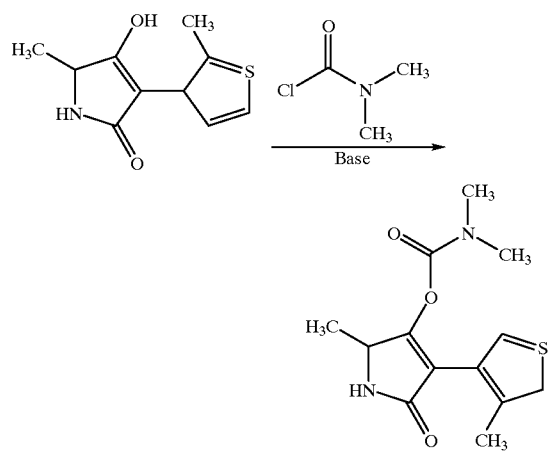

in which

A, B, D, X and n have the meanings given above
(Chem. Ind. (London) 1568 (1968)).

The compounds of the formula (XXV)

(XXV)

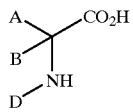

The compounds required as starting materials in process (A) according to the invention, of the formula (II)

(II)

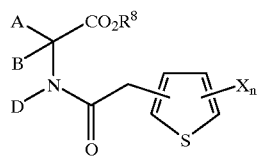

in which

A, B, D, X and n have the meanings given above are novel.

The compounds of the formula (XXV) are obtained by acylating amino acids of the formula (XXVI)

(XXVI)

in which

A, B, D, X, n and $R^8$ have the meanings given above, are novel.

The compounds of the formula (II) are obtained, for example, by acylating amino acid derivatives of the formula (XXIII)

in which

A, B and D have the meanings given above with thienylacetyl halides of the formula (XXIV)

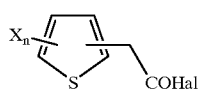
(XXIV)

in which
X and n have the meanings given above and
Hal represents chlorine or bromine,
by the Schotten-Baumann method (Organikum, VEB Deutscher Verlag der Wissenschaften, Berlin 1977, p. 505).

The compounds of the formula (XXIV) are in some cases known or can be prepared by known methods.

The compounds of the formulae (XXIII) and (XXVI) are in some cases known and/or can be prepared by known methods.

The substituted cyclic aminocarboxylic acids of the formula (XXVIa) in which A and B form a ring are in general obtainable by the Bucherer-Bergs synthesis or by the Strecker synthesis, in each of which syntheses they are produced in different isomeric forms. Thus the isomers obtained under the conditions of the Bucherer-Bergs synthesis are predominantly those (referred to for simplicity below as β) in which the radicals R and the carboxyl group are in equatorial positions, whereas the isomers obtained under the conditions of the Strecker synthesis are predominantly those (referred to for simplicity below as α) in which the amino group and the radicals R are in equatorial positions.

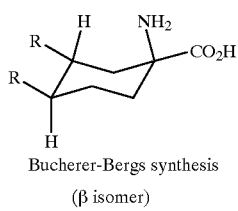

Bucherer-Bergs synthesis (β isomer)

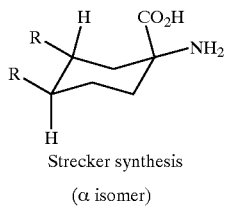

Strecker synthesis (α isomer)

(L. Munday, J. Chem. Soc. 4372 (1961); J. T. Eward, C. Jitrangeri, Can. J. Chem. 53, 3339 (1975)).

In addition, the starting materials used in the above process (A), of the formula (II)

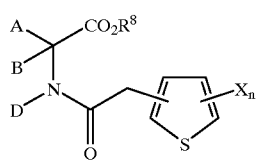
(II)

in which
A, B, D, X, n and $R^8$ have the meanings given above
can be prepared by reacting amino nitrites of the formula (XXVII)

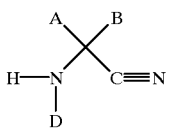
(XXVII)

in which
A, B and D have the meanings given above
with thienylacetyl halides of the formula (XXIV)

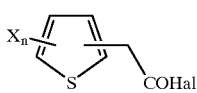
(XXIV)

in which
X and n have the meanings given above, and
Hal represents chlorine or bromine,
to give compounds of the formula (XXVIII)

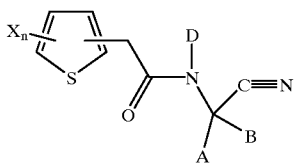
(XXVIII)

in which
A, B, D, X and n have the meanings given above and then subjecting these products to an acidic alcoholysis.

The compounds of the formula (XXVIII) are likewise novel.

The compounds required as starting materials in process (B) according to the invention, of the formula (III)

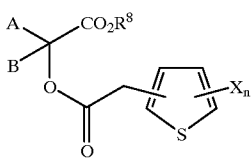
(III)

in which
A, B, X, n and $R^8$ have the meanings given above, are novel.

They can be prepared in a simple manner by methods which are known in principle.

For example, the compounds of the formula (III) are obtained by acylating 2-hydroxycarboxylic esters of the formula (XXIX)

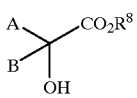
(XXIX)

in which
A, B and $R^8$ have the meanings given above
with thienylacetyl halides of the formula (XXIV)

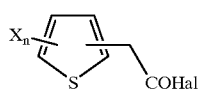 (XXIV)

in which
X and n have the meanings given above and
Hal represents chlorine or bromine
(Chem. Reviews 52, 237–416 (1953)).

Furthermore, compounds of the formula (III) are obtained by alkylating thienylacetic acids of the formula (XXX)

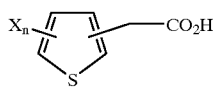 (XXX)

in which
X and n have the meanings given above
with α-halogenocarboxylic esters of the formula (XXXI)

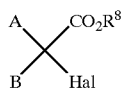 (XXXI)

in which
A, B and $R^8$ have the meanings given above, and
Hal represents chlorine or bromine.

The compounds of the formulae (XXX) and (XXXI) are generally known compounds and/or can be prepared in a simple manner by known methods.

The compounds required as starting materials in the above process (C), of the formula (IV)

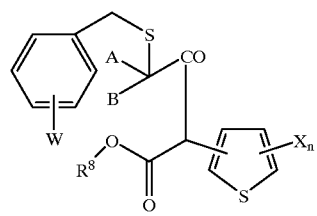 (IV)

in which
A, B, W, X, n and $R^8$ have the meanings given above, are novel.

They can be prepared by methods which are known in principle.

The compounds of the formula (IV) are obtained by acylating thienylacetic esters of the formula (XXXII)

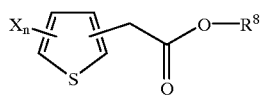 (XXXII)

in which
X, $R^8$ and n have the meanings given above
with 2-benzylthio-carbonyl halides of the formula (XXXIII)

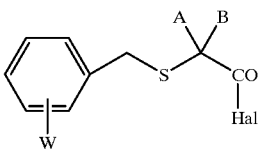 (XXXIIIV)

in which
A, B and W have the meanings given above, and
Hal represents halogen, especially chlorine or bromine,
in the presence of strong bases (see for example M. S. Chambers, E. J. Thomas, D. J. Williams, J. Chem. Soc. Chem. Commun., (1987), 1228).

The compounds of the formula (XXXII) are known from the literature, readily available, and in some cases are commercial compounds.

The benzylthio-carbonyl halides of the formula (XXXIII) are in some cases known and/or can be prepared by known methods (J. Antibiotics (1983), 26, 1589).

The halogenocarbonyl ketenes required as starting materials in the above process (Dα), of the formula (V), are novel. They can be prepared in a simple manner by methods which are known in principle (cf. for example Org. Prep. Proced. Int., 7, (4), 155–158, 1975 and DE 1 945 703). Thus compounds of the formula (V)

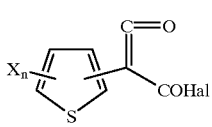 (V)

in which
X and n have the meanings given above, and
Hal represents chlorine or bromine, are obtained by reacting
thienylmalonic acids of the formula (XXXIV)

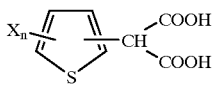 (XXXIV)

in which
X and n have the meanings given above
with acid halides such as, for example, thionyl chloride, phosphorus(V) chloride, phosphorus(III) chloride, oxalyl chloride, phosgene or thionyl bromide, if desired in the presence of catalysts such as, for example, diethylformamide, methylstearylformamide or triphenylphosphine and if desired in the presence of bases such as, for example, pyridine or triethylamine.

The thienylmalonic acids of the formula (XXXIV) are in some cases known compounds of organic chemistry and can be prepared in a simple manner by known methods (cf. e.g. Organikum, VEB Deutscher Verlag der Wissenschaften, Berlin 1977, p. 517 ff.).

The malonic esters required as starting materials in the above process (D β), of the formula (VI)

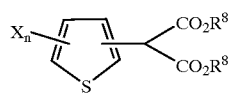 (VI)

in which

R⁸, X and n have the meanings given above,
are in some cases known and can be prepared by generally known methods of organic chemistry (cf. e.g. Tetrahedron Lett. 27, 2763 (1986) and Organikum, VEB Deutscher Verlag der Wissenschaften, Berlin 1977, p. 587 ff.).

The hydrazines which are also required as starting materials for carrying out processes (D-α) and (D-β) according to the invention, of the formula (VII)

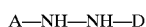 (VII), in which

A and D have the meanings given above,
are in some cases known and/or can be prepared by methods known from the literature (cf. for example Liebigs Ann. Chem. 585, 6 (1954); Reaktionen der organischen Synthese, C. Ferri, page 212, 513; Georg Thieme Verlag Stuttgart, 1978; Liebigs Ann. Chem. 443, 242 (1925); Chem. Ber. 98, 2551 (1965), EP 508 126).

The ketene acid halides of the formula (V) required as starting materials for carrying out process (E) have already been described for process (D) according to the invention. The carbonyl compounds required as starting materials for process (E) according to the invention, of the formula (VIII)

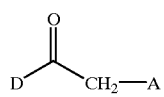 (VIII)

in which

A and D have the meanings given above, are commercial compounds, generally known compounds, or compounds which are accessible by known methods.

The preparation of the ketene acid chlorides of the formula (V) which are required as starting materials for carrying out process (F) according to the invention has already been described for process (D) according to the invention. The thioamides required to carry out process (F) according to the invention, of the formula (IX)

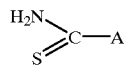 (IX)

in which

A has the meaning given above, are compounds which are generally known in organic chemistry.

The compounds required as starting materials in the above process (G), of the formula (X)

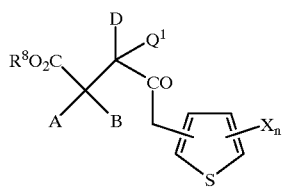 (X)

in which

A, B, D, Q¹, X, n and R⁸ have the meanings given above, are novel. They can be prepared by methods which are known in principle. The compounds of the formula (X) are obtained by esterifying 5-thienyl-4-ketocarboxylic acids of the formula (XXXV)

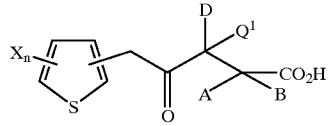 (XXXV)

in which

X, A, B, D, Q¹ and n have the meanings given above (cf e.g. Organikum, 15th edition, Berlin, 1977, page 499).

The 5-thienyl-4-ketocarboxylic acids of the formula (XXXV)

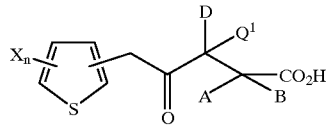 (XXXV)

in which

A, B, D, Q¹, X and n have the meanings given above are novel, but can be prepared by methods which are known in principle.

For example, the compounds of the formula (XXXV) are obtained by reacting carboxylic anhydrides of the formula (XXXVI)

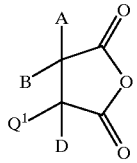 (XXXVI)

in which

A, B, D and Q¹ have the meanings given above
with organometallic compounds of the formula (XXXVII)

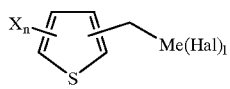 (XXXVII)

in which

X and n have the meanings given above,

Me represents mono- or divalent metal ions such as, for example, lithium or magnesium, Hal represents chlorine or bromine and l represents 0 or 1 in the presence of a diluent (cf. e.g. Organikum, 15th edition, Berlin, 1977, page 623).

The compounds (XXXVI) and (XXVII) are in some cases known and/or can be prepared in a simple manner by known methods (cf. e.g. Organikum, 15th edition, Berlin, 1977, pages 525, 526 and 623).

In addition, 5-thienyl-4-ketocarboxylic acids of the formula (XXXV)

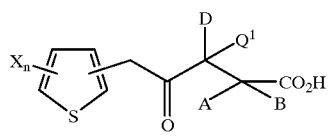

(XXXV)

in which

A, B, D, $Q^1$, X and n have the meanings given above are obtained by subjecting 2-thienyl-3-oxo-adipic esters of the formula (XXXVIII)

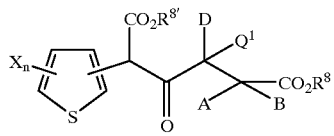

(XXXVIII)

in which

A, B, D, $Q^1$, X and n have the meanings given above, and $R^8$ and $R^{8'}$ are identical or different and represent alkyl, preferably $C_1$–$C_6$-alkyl, to hydrolysis and decarboxylation, if desired in the presence of a diluent and if desired in the presence of a base or acid (cf. e.g. Organikum, 15th edition, Berlin, 1977, page 519 to 521).

The compounds of the formula (XXXVIII)

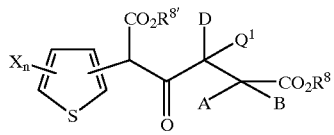

(XXXVIII)

in which

A, B, D, $Q^1$, $R^8$, $R^{8'}$ and n have the meanings given above are obtainable by acylating dicarboxylic monoester chlorides of the formula (XXXIX)

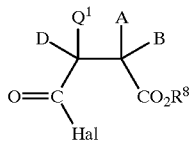

(XXXIX)

in which

A, B, D, $Q^1$ and $R^8$ have the meanings given above and Hal represents chlorine or bromine with thienylacetic esters of the formula (XXXII)

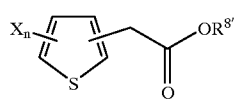

(XXXII)

in which $R^{8'}$, X and n have the meanings given above in the presence of a diluent and in the presence of a base (cf. e.g. M. S. Chambers, E. J. Thomas, D. J. Williams, J. Chem. Soc. Chem. Commun., (1987), 1228).

The compounds of the formulae (XXXII) and (XXXIX) are generally known compounds of organic chemistry and/or can be prepared in a simple manner by methods which are known in principle.

The compounds required as starting materials in the above process (H), of the formula (XI)

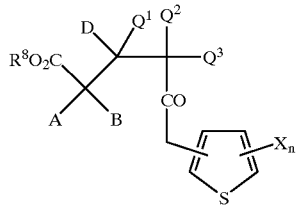

(XI)

in which

A, B, D, $Q^1$, $Q^2$, $Q^3$, X, n and $R^8$ have the meaning given above, are novel. They can be prepared by methods which are known in principle. The compounds of the formula (XI) are obtained by esterifying 6-thienyl-5-ketocarboxylic acids of the formula (XL)

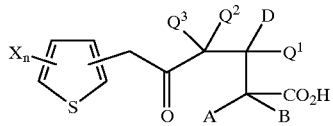

(XL)

in which

X, A, B, D, $Q^1$, $Q^2$, $Q^3$ and n have the meanings given above (cf e.g. Organikum, 15th edition, Berlin, 1977, page 499).

The 6-thienyl-5-ketocarboxylic acids of the formula (XL)

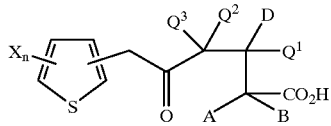
(XL)

in which
A, B, D, $Q^1$, $Q^2$, $Q^3$, X and n have the meanings given above are novel, but can be prepared by methods which are known in principle.

The compounds of the formula (XL) are obtained by reacting carboxylic anhydrides of the formula (XLI)

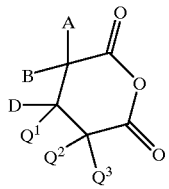
(XLI)

in which
A, B, D, $Q^1$, $Q^2$ and $Q^3$ have the meanings given above with organometallic compounds of the formula (XXXVII)

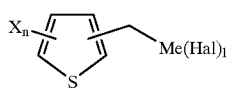
(XXXVII)

in which
X and n have the meanings given above,

| | |
|---|---|
| Me | represents mono- or divalent metal ions such as, for example, lithium and magnesium, |
| Hal and | represents chlorine or bromine |
| 1 | represents a number 0 or 1 | in the presence of a diluent (cf. e.g. Organikum, 15th edition, Berlin, 1977, page 623).

The compounds (XXVII) and (XLI) are in some cases known and/or can be prepared in a simple manner by known methods (cf. e.g. Organikum, 15th edition, Berlin, 1977, pages 525, 526 and 623).

Furthermore, 6-thienyl-5-ketocarboxylic acids of the formula (XL)

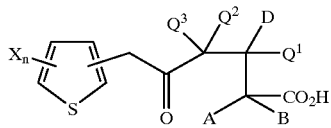
(XL)

in which
A, B, D, $Q^1$, $Q^2$, $Q^3$, X and n have the meanings given above
are obtained by subjecting 2-thienyl-3-oxo-heptanedioic esters of the formula (XLII)

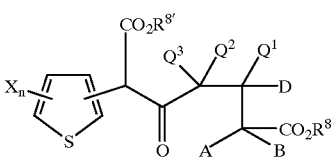
(XLII)

in which
A, B, D, $Q^1$, $Q^2$, $Q^3$, X, $R^8$, $R^{8'}$ and n have the meanings given above
to hydrolysis and decarboxylation, if desired in the presence of a diluent and if desired in the presence of a base or acid (cf. e.g. Organikum, 15th edition, Berlin, 1977, page 519 to 521).

The compounds of the formula (XLII)

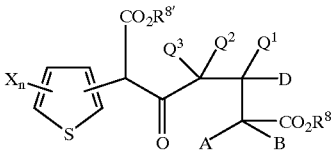
(XLII)

in which
A, B, D, $Q^1$, $Q^2$, $Q^3$, Z, $R^8$, $R^{8'}$ and n have the meanings given above are novel and are obtainable
by acylating dicarboxylic monoester chlorides of the formula (XLIII)

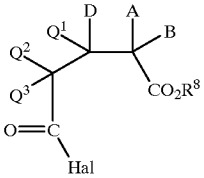
(XLIII)

in which
A, B, D, $Q^1$, $Q^2$, $Q^3$ and $R^8$ have the meanings given above, and
Hal represents chlorine or bromine,
with thienylacetic esters of the formula (XXXII)

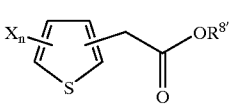
(XXXII)

in which
X, $R^{8'}$ and n have the meanings given above
in the presence of a diluent and in the presence of a base (cf. e.g. M. S. Chambers, E. J. Thomas, D. J. Williams, J. Chem. Soc. Chem. Commun., (1987), 1228).

The compounds of the formulae (XXXII) and (XLIII) are generally known compounds of organic chemistry and/or can be prepared in a simple manner by methods which are known in principle (cf. e.g. EP-A-0 307 103).

The compounds which are likewise required as starting materials for carrying out processes (I), (J), (K), (L), (M), (N) and (O) according to the invention, namely acyl halides of the formula (XII), carboxylic anhydrides of the formula (XIII), chloroformic esters or chloroformic thioesters of the formula (XIV), chloromonothioformic esters or chlorodithioformic esters of the formula (XV), alkyl halides of the formula (XVI), sulfonyl chlorides of the formula (XVII), phosphorus compounds of the formula (XVIII) and metal hydroxides, metal alkoxides or amines of the formula (XIX) and (XX), and isocyanates of the formula (XXI) and carbamoyl chlorides of the formula (XXII), are generally known compounds of organic or inorganic chemistry.

Process (A) comprises subjecting compounds of the formula (II) in which A, B, D, X, n and $R^8$ have the meanings given above to an intramolecular condensation in the presence of bases.

As diluents in process (A) according to the invention it is possible to employ all inert organic solvents. Preferred possibilities for use are hydrocarbons such as toluene and xylene, ethers such as dibutyl ether, tetrahydrofuran, dioxane, glycol dimethyl ether and diglycol dimethyl ether, polar solvents such as dimethyl sulfoxide, sulfolane, dimethylformamide and N-methyl-pyrrolidone, and alcohols such as methanol, ethanol, propanol, isopropanol, butanol, isobutanol and tert-butanol.

As bases (deprotonating agents) for carrying out process (A) according to the invention it is possible to employ all conventional proton acceptors. Preferred possibilities for use are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). It is also possible to use alkali metals such as sodium or potassium. Compounds which can also be employed are alkali metal and alkaline earth metal amides and hydrides, such as sodium amide, sodium hydride and calcium hydride, and also alkali metal alcoholates, such as sodium methylate, sodium ethylate and potassium tert-butylate.

The reaction temperatures when carrying out process (A) according to the invention can be varied within a relatively large range. It is in general carried out at temperatures of between 0° C. and 250° C., preferably between 50° C. and 150° C.

Process (A) according to the invention is generally carried out under atmospheric pressure.

When carrying out process (A) according to the invention, the reaction components of the formula (II) and the deprotonating bases are generally employed in approximately twice the equimolar quantity. However, it is also possible to use one or other component in a relatively large excess (up to 3 mol).

Process (B) comprises subjecting compounds of the formula (III) in which A, B, X, n and $R^8$ have the meanings given above to an intramolecular condensation in the presence of a base and of a diluent.

As diluents in process (B) according to the invention it is possible to employ all inert organic solvents. Preferred possibilities for use are hydrocarbons such as toluene and xylene, ethers such as dibutyl ether, tetrahydrofuran, dioxane, glycol dimethyl ether and diglycol dimethyl ether, and polar solvents such as dimethyl sulfoxide, sulfolane, dimethylformamide and N-methyl-pyrrolidone. It is also possible to employ alcohols such as methanol, ethanol, propanol, isopropanol, butanol, isobutanol and tert-butanol.

As bases (deprotonating agents) for carrying out process (B) according to the invention it is possible to employ all conventional proton acceptors. Preferred possibilities for use are alkali metal and alkaline earth metal oxides, hydroxides and carbonates, such as sodium carbonate, potassium hydroxide, magnesium oxide, calcium oxide, sodium carbonate, potassium carbonate and calcium carbonate, which can also be employed in the presence of phase transfer catalysts such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). It is also possible to use alkali metals such as sodium or potassium. Compounds which can also be employed are alkali metal and alkaline earth metal amides and hydrides, such as sodium amide, sodium hydride and calcium hydride, and also alkali metal alcoholates, such as sodium methylate, sodium ethylate and potassium tert-butylate.

The reaction temperatures when carrying out process (B) according to the invention can be varied within a relatively large range. It is in general carried out at temperatures of between 0° C. and 250° C., preferably between 50° C. and 150° C.

Process (B) according to the invention is generally carried out under atmospheric pressure.

When carrying out process (B) according to the invention, the reaction components of the formula (III) and the deprotonating bases are generally employed in approximately twice the equimolar quantity. However, it is also possible to use one or other component in a relatively large excess (up to 3 mol).

Process (C) comprises subjecting compounds of the formula (IV) in which A, B, W, X, n and $R^8$ have the meanings given above to an intramolecular cyclization in the presence of acids and if desired in the presence of a diluent.

As diluents in process (C) according to the invention it is possible to employ all inert organic solvents. Preferred possibilities for use are hydrocarbons such as toluene and xylene, halogenated hydrocarbons such as dichloromethane, chloroform, ethylene chloride, chlorobenzene and dichlorobenzene, and polar solvents such as dimethyl sulfoxide, sulfolane, dimethylformamide and N-methyl-pyrrolidone. It is also possible to employ alcohols such as methanol, ethanol, propanol, isopropanol, butanol, isobutanol and tert-butanol.

If desired, the acid employed can also be used as diluent.

As acids in process (C) according to the invention it is possible to employ all customary inorganic and organic acids, for example hydrohalic acids, sulfuric acid, alkyl-, aryl- and haloalkylsulfonic acids, and, in particular, halogenated alkylcarboxylic acids such as trifluoroacetic acid.

The reaction temperatures when carrying out process (C) according to the invention can be varied within a relatively large range. It is in general carried out at temperatures between 0° C. and 250° C., preferably between 50° C. and 150° C.

Process (C) according to the invention is generally carried out under atmospheric pressure.

When carrying out process (C) according to the invention, the reaction components of the formula (IV) and the acid are employed, for example, in equimolar amounts. It is also possible, if desired, to use the acid as solvent or as catalyst.

The processes (D-α) and (D-β) comprise subjecting compounds of the formulae (V) or (VI) in which X, $R^8$, n and Hal have the meanings given above, and compounds of the formula (VII) in which A and D have the meanings given above, to a condensation reaction, if desired in the presence of a base and if desired in the presence of a diluent.

As diluents in processes (D-α) and (D-β) according to the invention it is possible to employ all inert organic solvents. Preferred possibilities for use are hydrocarbons such as toluene and xylene, ethers such as dibutyl ether, tetrahydrofuran, dioxane, glycol dimethyl ether and diglycol dimethyl ether, and polar solvents such as dimethyl sulfoxide, sulfolane, dimethylformamide and N-methyl-pyrrolidone.

As bases (deprotonating agents) for carrying out process (D-α) and (D-β) according to the invention it is possible to employ all conventional proton acceptors. Preferred possibilities for use are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). It is also possible to use alkali metals such as sodium or potassium. Other compounds which can be employed are alkali metal and alkaline earth metal amides and hydrides, such as sodium amide, sodium hydride and calcium hydride, and also alkali metal alcoholates, such as sodium methylate, sodium ethylate and potassium tert-butylate.

The reaction temperatures when carrying out process (D-α) and (D-β) according to the invention can be varied within a relatively large range. It is in general carried out at temperatures of between −20° C. and 250° C., preferably between 0° C. and 150° C.

Processes (D-α) and (D-β) according to the invention are generally carried out under atmospheric pressure.

When carrying out processes (D-α) and (D-β) according to the invention, the reaction components of the formulae (V) and (VII) or (VI) and (VII) and the deprotonating bases which are employed if desired are in general employed in approximately equimolar amounts. However, it is also possible to use one or other component in a relatively large excess (up to 3 mol).

Process (E) according to the invention comprises reacting carbonyl compounds of the formula (VIII) with ketene acid halides of the formula (II) in the presence of a diluent and if desired in the presence of an acid acceptor.

Diluents which can be employed in this context are all inert organic solvents. Preferred possibilities for use are hydrocarbons such as toluene and xylene, ethers such as dibutyl ether, glycol dimethyl ether and diglycol dimethyl ether, and polar solvents such as dimethyl sulfoxide, sulfolane, dimethylformamide and N-methyl-pyrrolidone.

As acid acceptors when carrying out process (E) according to the invention, it is possible to use all customary acid acceptors.

Preferred possibilities for use are tertiary amines such as triethylamine, pyridine, diazabicyclooctane (DABCO), diazabicycloundecene (DBU), diazabicyclononene (DBN), Hünig base and N,N-dimethylaniline.

The reaction temperatures when carrying out process (E) according to the invention can be varied within a relatively large range. It is expediently carried out at temperatures of between 0° C. and 250° C., preferably between 50° C. and 220° C.

Process (E) is expediently carried out under atmospheric pressure.

When carrying out process (E) according to the invention, the reaction components of the formulae (VIII) and (V) in which A, D, X and n have the meanings given above and Hal represents halogen, and, if desired, the acid acceptors, are expediently employed in approximately equimolar amounts. However, it is also possible to use one or other component in a relatively large excess (up to 5 mol).

Process (F) according to the invention comprises reacting thioamides of the formula (IX) with ketene acid halides of the formula (V), if desired in the presence of a diluent and if desired in the presence of an acid acceptor.

As diluents in process (F) it is possible to employ all inert organic solvents. Preferred possibilities for use are hydrocarbons such as toluene and xylene, ethers such as dibutyl ether, glycol dimethyl ether and diglycol dimethyl ether, and polar solvents such as dimethyl sulfoxide, sulfolane, dimethylformamide and N-methyl-pyrrolidone.

As acid acceptors it is possible to use all customary acid acceptors.

Preferred possibilities for use are tertiary amines such as triethylamine, pyrridine, diazabicyclooctane (DABCO), diazabicycloundecene (DBU), diazabicyclononene (DBN), Hünig base and N,N-dimethyl-aniline.

The reaction temperatures can be varied within a relatively large range. The process is expediently carried out at temperatures of between 0° C. and 250° C., preferably between 20° C. and 220° C.

Process (F) is expediently carried out under atmospheric pressure.

When carrying out the process (F) according to the invention, the reaction components of the formulae (IX) and (V) in which A, X and n have the meanings given above and Hal represents halogen, and, if desired, the acid acceptors, are expediently employed in approximately equimolar amounts. However, it is also possible to use one or other component in a relatively large excess (up to 5 mol).

Process (G) comprises subjecting compounds of the formula (X) in which A, B, D, $Q^1$, X, n and $R^8$ have the meanings given above to an intramolecular condensation in the presence of a base and if desired in the presence of a diluent.

As diluents in process (G) according to the invention it is possible to employ all inert organic solvents. Preferred possibilities for use are hydrocarbons such as toluene and xylene, ethers such as dibutyl ether, tetrahydrofuran, dioxane, glycol dimethyl ether and diglycol dimethyl ether, and polar solvents such as dimethyl sulfoxide, sulfolane, dimethylformamide and N-methyl-pyrrolidone. It is also possible to employ alcohols such as methanol, ethanol, propanol, isopropanol, butanol, isobutanol and tert-butanol.

As bases (deprotonating agents) for carrying out process (G) according to the invention it is possible to employ all conventional proton acceptors. Preferred possibilities for use are alkali metal and alkaline earth metal oxides, hydroxides and carbonates, such as sodium hydroxide,. potassium hydroxide, magnesium oxide, calcium oxide, sodium carbonate, potassium carbonate and calcium carbonate, which can also be employed in the presence of phase transfer catalysts such as, for example, triethylbenzylammonium chloride, tetrabutylammonium bromide, Adogen 464 (methyltrialkyl($C_8$–$C_{10}$)ammonium chloride) or TDA 1 (tris-(methoxyethoxyethyl)-amine). It is also possible to use alkali metals such as sodium or potassium. Compounds which can also be employed are alkali metal and alkaline earth metal amides and hydrides, such as sodium amide, sodium hydride and calcium hydride, and also alkali metal alcoholates, such as sodium methylate, sodium ethylate and potassium tert-butylate.

The reaction temperatures when carrying out process (G) according to the invention can be varied within a relatively large range. It is in general carried out at temperatures of between 0° C. and 250° C., preferably between 50° C. and 150° C.

Process (G) according to the invention is generally carried out under atmospheric pressure.

When carrying out process (G) according to the invention, the reaction components of the formula (X) and the deprotonating bases are generally employed in approximately equimolar amounts. However, it is also possible to use one or other component in a relatively large excess (up to 3 mol).

Process (H) comprises subjecting compounds of the formula (XI) in which A, B, D, $Q^1$, $Q^2$, $Q^3$, X, n and $R^8$ have the meanings given above to an intramolecular condensation in the presence of a base and if desired in the presence of a diluent.

As diluents in process (H) according to the invention it is possible to employ all inert organic solvents. Preferred possibilities for use are hydrocarbons such as toluene and xylene, ethers such as dibutyl ether, tetrahydrofuran, dioxane, glycol dimethyl ether and diglycol dimethyl ether, and polar solvents such as dimethyl sulfoxide, sulfolane, dimethylformamide and N-methyl-pyrrolidone. It is also possible to employ alcohols such as methanol, ethanol, propanol, isopropanol, butanol, isobutanol and tert-butanol.

As bases (deprotonating agents) for carrying out process (H) according to the invention it is possible to employ all conventional proton acceptors. Preferred possibilities for use are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts such as, for example, triethylbenzylammonium chloride, tetrabutylammonium bromide, Adogen 464 (methyltrialkyl($C_8$–$C_{10}$)ammonium chloride) or TDA 1 (tris-(methoxyethoxyethyl)-amine). It is also possible to use alkali metals such as sodium or potassium. Compounds which can also be employed are alkali metal and alkaline earth metal amides and hydrides, such as sodium amide, sodium hydride and calcium hydride, and also alkali metal alcoholates, such as sodium methylate, sodium ethylate and potassium tert-butylate.

The reaction temperatures when carrying out process (H) according to the invention can be varied within a relatively large range. It is in general carried out at temperatures of between 0° C. and 250° C., preferably between 50° C. and 150° C.

Process (H) according to the invention is generally carried out under atmospheric pressure.

When carrying out process (H) according to the invention, the reaction components of the formula (XI) and the deprotonating bases are generally employed in approximately equimolar amounts. However, it is also possible to use one or other component in a relatively large excess (up to 3 mol).

Process (Iα) comprises reacting compounds of the formulae (I-1-a) to (I-8-a), if desired in the presence of a diluent and if desired in the presence of an acid-binding agent, with carbonyl halides of the formula (XII).

As diluents in process (Iα) according to the invention it is possible to employ all solvents which are inert with respect to the acyl halides. Preferred possibilities for use are hydrocarbons such as benzine, benzene, toluene, xylene and tetralin, halogenated hydrocarbons such as methylene chloride, chloroform, carbon tetrachloride, chlorobenzene and o-dichlorobenzene, ketones such as acetone and methyl isopropyl ketone, ethers such as diethyl ether, tetrahydrofuran and dioxane, carboxylic esters such as ethyl acetate, and strongly polar solvents such as dimethyl sulfoxide and sulfolane. If the stability of the acyl halide to hydrolysis permits, the reaction can also be carried out in the presence of water.

Suitable acid-binding agents in the reaction according to the process (Iα) according to the invention are all customary acid acceptors. Preferred possibilities for use are tertiary amines such as triethylamine, pyridine, diazabicyclooctane (DABCO), diazabicycloundecene (DBU), diazabicyclononene (DBN), Hünig base and N,N-dimethyl-aniline, alkaline earth metal oxides such as magnesium oxide and calcium oxide, alkali metal and alkaline earth metal carbonates, such as sodium carbonate, potassium carbonate and calcium carbonate, and alkali metal hydroxides such as sodium hydroxide and potassium hydroxide.

The reaction temperatures when carrying out process (Iα) according to the invention can also be varied within a relatively large range. It is in general carried out at temperatures between –20° C. and +150° C., preferably between 0° C. and 100° C.

When carrying out process (Iα) according to the invention, the starting materials of the formulae (I-1-a) to (I-8-a) and the carbonyl halide of the formula (XII) are generally employed in approximately equivalent amounts. However, it is also possible to employ the carbonyl chloride in a relatively large excess (up to 5 mol). Working up is by conventional methods.

Process (Iβ) comprises reacting compounds of the formulae (I-1-a) to (I-8-a), if desired in the presence of a diluent and if desired in the presence of an acid-binding agent, with carboxylic anhydrides of the formula (XIII).

As diluents in process (Iβ) according to the invention it is possible preferably to use those diluents which are also preferably suitable when acyl halides are used. In addition, it is also possible for a carboxylic anhydride employed in excess to function simultaneously as diluent.

The reaction temperatures when carrying out process (Iβ) according to the invention when using carboxylic anhydrides can also be varied within a relatively large range. It is in general carried out at temperatures between –20° C. and +150° C., preferably between 0° C. and 100° C.

When carrying out the process according to the invention, the starting materials of the formulae (I-1-a) to (I-8-a) and the carboxylic anhydride of the formula (XIII) are generally used in approximately equivalent amounts. However, it is also possible to employ the carboxylic anhydride in a relatively large excess (up to 5 mol). Working up is by conventional methods.

The general procedure is to remove diluent, excess carboxylic anhydride and the carboxylic acid which is formed, by distillation or by washing with an organic solvent or with water.

Process (J) comprises reacting compounds of the formulae (I-1-a) to (I-8-a), if desired in the presence of a diluent and if desired in the presence of an acid-binding agent, with chloroformic esters or chloroformic thioesters of the formula (XIV).

Suitable acid-binding agents in the reaction according to process (J) according to the invention are all customary acid acceptors. Preferred possibilities for use are tertiary amines such as triethylamine, pyridine, DABCO, DBU, DBA, Hünig base and N,N-dimethyl-aniline, alkaline earth metal oxides such as magnesium oxide and calcium oxide, alkali metal and alkaline earth metal carbonates, such as sodium carbonate, potassium carbonate and calcium carbonate, and alkali metal hydroxides such as sodium hydroxide and potassium hydroxide.

As diluents in process (J) according to the invention it is possible to use all solvents which are inert with respect to the chloroformic esters or chloroformic thioesters. Preferred possibilities for use are hydrocarbons such as benzine, benzene, toluene, xylene and tetralin, halogenated hydrocarbons such as methylene chloride, chloroform, carbon tetrachloride, chlorobenzene and o-dichlorobenzene, ketones such as acetone and methyl isopropyl ketone, ethers such as diethyl ether, tetrahydrofuran and dioxane, carboxylic esters such as ethyl acetate, and strongly polar solvents such as dimethyl sulfoxide and sulfolane.

The reaction temperatures when carrying out process (J) according to the invention can be varied within a relatively large range. When working in the presence of a diluent and an acid-binding agent, the reaction temperatures are in general between −20° C. and +100° C., preferably between 0° C. and 50° C.

Process (J) according to the invention is generally carried out under atmospheric pressure.

When carrying out process (J) according to the invention, the starting materials of the formulae (I-1-a) to (I-8-a) and the corresponding chloroformic ester or chloroformic thioester of the formula (XIV) are generally used in approximately equivalent amounts. However, it is also possible to use one or other component in a relatively large excess (up to 2 mol). Working up is then by conventional methods. The general procedure is to remove precipitated salts and to concentrate the remaining reaction mixture by stripping off the diluent.

Process (K) according to the invention comprises reacting compounds of the formulae (I-1-a) to (I-8-a), with (Kα) compounds of the formula (XV) in the presence of a diluent and if desired in the presence of an acid-binding agent, or with (Kβ) carbon disulfide and then with alkyl halides of the formula (XVI).

In the preparation process (Kα), per mol of starting compound of the formulae (I-1-a) to (I-8-a), about 1 mol of chloromonothioformic ester or chlorodithioformic ester of the formula (XV) is reacted at from 0 to 120° C., preferably at from 20 to 60° C.

Suitable diluents which are added if desired are all inert polar organic solvents, such as ethers, amides, sulfones and sulfoxides, but also halogenoalkanes.

It is preferred to employ dimethyl sulfoxide, tetrahydrofuran, dimethylformamide or methylene chloride.

If, in a preferred embodiment, the enolate salt of the compounds (I-1-a) to (I-8-a) is prepared by addition of strong deprotonating agents such as, for example, sodium hydride or potassium tert-butylate, then the addition of acid-binding agents as well can be omitted.

If acid-binding agents are employed, then suitable such agents are customary inorganic or organic bases, for example sodium hydroxide, sodium carbonate, potassium carbonate, pyridine and triethylamine.

The reaction can be carried out at atmospheric pressure or under elevated pressure, preferably at atmospheric pressure. Working up is by conventional methods.

In preparation process (Kβ), per mol of starting compounds of the formulae (I-1-a) to (I-8-a), the equimolar amount or an excess of carbon disulfide is added. This process variant is preferably carried out at temperatures of from 0 to 50° C. and, in particular, at from 20 to 30° C.

It is often expedient first to prepare the corresponding salt from the compounds of the formulae (I-1-a) to (I-8-a) by addition of a base (for example potassium tert-butylate or sodium hydride). The compounds (I-1-a) to (I-8-a) are reacted with carbon disulfide until the formation of the intermediate compound is at an end, for example after stirring for a number of hours at room temperature.

As bases in process (Kβ) it is possible to employ all customary proton acceptors. Preferred possibilities for use are alkali metal hydrides, alkali metal alcoholates, alkali metal or akaline earth metal carbonates or hydrogen carbonates, or nitrogen bases. Examples which may be mentioned are sodium hydride, sodium methanolate, sodium hydroxide, calcium hydroxide, potassium carbonate, sodium hydrogen carbonate, triethylamine, dibenzylamine, diisopropylamine, pyridine, quinoline, diazabicyclooctane (DABCO), diazabicyclononene (DBN) and diazabicycloundecene (DBU).

As diluents in this process it is possible to use all conventional solvents.

Preferred possibilities for use are aromatic hydrocarbons such as benzene or toluene, alcohols such as methanol, ethanol, isopropanol or ethylene glycol, nitriles such as acetonitrile, ethers such as tetrahydrofuran or dioxane, amides such as dimethylformamide, or other polar solvents such as dimethyl sulfoxide or sulfolane.

The subsequent reaction with the alkyl halide of the formula (XVI) is carried out preferably at from 0 to 70° C. and, in particular, at from 20 to 50° C. In this reaction, at least the equimolar amount of alkyl halide is employed.

The reaction is carried out at atmospheric pressure or under elevated pressure, preferably at atmospheric pressure.

Working up is again by conventional methods.

Process (L) according to the invention comprises reacting compounds of the formulae (I-1-a) to (I-8-a) with sulfonyl chlorides of the formula (XVII), if desired in the presence of a diluent and if desired in the presence of an acid-binding agent.

In preparation process (L), per mol of starting compound of the formula (I-1-a) to (I-8-a), about 1 mol of sulfonyl chloride (XVII) is reacted at from −20 to 150° C., preferably at from 20 to 70° C.

Suitable diluents which may be added if desired are all inert polar organic solvents, such as ethers, amides, nitriles, sulfones, sulfoxides or halogenated hydrocarbons such as methylene chloride.

It is preferred to employ dimethyl sulfoxide, tetrahydrofuran, dimethylformamide or methylene chloride.

If, in a preferred embodiment, the enolate salt of the compounds (I-1-a) to (I-8-a) is prepared by addition of strong deprotonating agents (for example sodium hydride or potassium tert-butylate), then the addition of acid-binding agents as well can be omitted.

If acid-binding agents are employed, then suitable such agents are customary inorganic or organic bases, for example sodium hydroxide, sodium carbonate, potassium carbonate, pyridine or triethylamine.

The reaction can be carried out at atmospheric pressure or under elevated pressure, preferably at atmospheric pressure. Working up is by conventional methods.

Process (M) according to the invention comprises reacting compounds of the formulae (I-1-a) to (I-8-a) with phosphorus compounds of the formula (XVIII), if desired in the presence of a diluent and if desired in the presence of an acid-binding agent.

In preparation process (M) to obtain compounds of the structures (I-1-e) to (I-8-e), per mol of the compounds (I-1-a) to (I-8-a), from 1 to 2 mol, preferably from 1 to 1.3 mol, of the phosphorus compound of the formula (XVIII) are reacted at temperatures between −40° C. and 150° C., preferably between −10 and 110° C.

Suitable diluents which may be added if desired are all inert, polar, organic solvents, such as ethers, amides, nitrites, carboxylic esters, sulfides, sulfones, sulfoxides, etc.

It is preferred to employ acetonitrile, dimethyl sulfoxide, tetrahydrofuran, dimethylformamide or methylene chloride.

Suitable acid-binding agents which may be added if desired are customary inorganic or organic bases, such as hydroxides, carbonates or amines. Examples which may be given are sodium hydroxide, sodium carbonate, potassium carbonate, pyridine and triethylamine.

The reaction can be carried out at atmospheric pressure or under elevated pressure, preferably at atmospheric pressure. Working up is by conventional methods of organic chemistry. The purification of the end products obtained preferably takes place by crystallization, chromatographic purification or by so-called "incipient distillation", i.e. removal of the volatile constituents in vacuo.

Process (N) comprises reacting compounds of the formulae (I-1-a) to (I-8-a) with metal hydroxides or metal alkoxides of the formula (XIX) or amines of the formula (XX), if desired in the presence of a diluent.

As diluents it is possible preferably to employ ethers such as tetrahydrofuran, dioxane or diethyl ether or else alcohols such as methanol, ethanol or isopropanol, but also water. Process (N) according to the invention is generally carried out under atmospheric pressure. The reaction temperatures are in general between −20° C. and 100° C., preferably between 0° C. and 50° C.

Process (O) according to the invention comprises reacting compounds of the formulae (I-1-a) to (I-8-a) with (Oα) compounds of the formula (XXI), if desired in the presence of a diluent and if desired in the presence of a catalyst, or (Oβ) with compounds of the formula (XXII), if desired in the presence of a diluent and if desired in the presence of an acid-binding agent.

In preparation process (Oα), per mol of starting compound of the formulae (I-1-a) to (I-8-a), about 1 mol of isocyanate of the formula (XXI) is reacted at from 0 to 100° C., preferably at from 20 to 50° C.

Suitable diluents which may be added if desired are all inert organic solvents, such as ethers, amides, nitriles, sulfones or sulfoxides.

It is possible if desired to add catalysts in order to accelerate the reaction. As catalysts, it is possible with great advantage to employ organotin compounds such as, for example, dibutyltin dilaurate. The process is preferably carried out at atmospheric pressure.

In preparation process (Oβ), per mol of starting compound of the formulae (I-1-a) to (I-8-a), about 1 mol of carbamoyl chloride of the formula (XXII) is reacted at from 0 to 150° C., preferably at from 20 to 70° C.

Suitable diluents which may be added if desired are all inert, polar, organic solvents, such as ethers, amides, nitriles, carboxylic esters, sulfones, sulfoxides or halogenated hydrocarbons.

The active compounds according to the invention are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis, Schistocerca gregaria* and Supella spp.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., Phthirus spp., Pediculus spp., Haematopinus spp., Linognathus spp. and Solenopotes spp.

From the order of the Mallophaga, for example, Trichodectes spp., Damalinea spp., Trimenopon spp., Monopon spp., Trinoton spp., Bovicola spp., Werneckiella spp., Lepikentron spp. and Felicola spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus*, Triatoma spp. and Panstrongylus spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus,*

*Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., Calliphora spp., Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae, Tipula paludosa*, Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Hydrotaea spp., Stomoxys spp., Haematobia spp., Morellia spp., Fannia spp., Glossina spp., Calliphora spp., Wohlfahrtia spp., Sarcophaga spp., Oestrus spp., Hypoderma spp., Gasterophilus spp., Hippobosca spp., Lipoptena spp., Melophagus spp. and Muscina spp.

From the order of the Siphonapterida, for example, Xenopsylla spp., Ceratophyllus spp., Pulex spp. and Ctenocephalides spp.

From the order of the Arachnida, for example, *Scorpio maurus* and *Latrodectus mactans*.

From the order of the Acarina, for example, Myocoptes spp., Otodectes spp., *Acarus siro*, Argas spp., Ornithodoros spp., Ornithonyssus spp., Dermanyssus spp., *Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Dermacentor spp., Haemaphysalis spp., Raillietia spp., Pneumonyssus spp., Sternostorma spp. and Varroa spp.

From the order of the Actinedida (Prostigmata) and Acaridida (Astigmata), for example: Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds according to the invention are distinguished by a high insecticidal and acaricidal activity.

They can be used with particular success, for example, to control the red spider mite.

The active compounds according to the invention can be used as defoliants, desiccants, agents for destroying broad-leaved plants and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, ornamental plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds according to the invention are very highly suited to the selective control of monocotyledon weeds in dicotyledon cultures, both pre- and post-emergence. They can, for example, be employed in cotton or sugar beet with very great success for controlling grass weeds.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine encapsulations in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention may be present in its customary commercial formulations and in the use forms prepared from these formulations, as a mixture with other active compounds, such as insecticides, attractants, sterilants, bactericides, acaricides, nematicides, fungicides, growth-regulating substances or herbicides. The insecticides, for example, include phosphates, carbamates, carboxylic esters, chlorinated hydrocarbons, phenylureas, substances produced by microorganisms, etc.

Examples of Particularly Advantageous Co-Components are the Following Compounds

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxy-phenyl)-acetamide; 8-hydroxyquinoline sulfate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, biteranol, blasticidin-S, bromuconazole, bupirimate, buthiobate, calcium polysulfide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlofos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides for example anilides such as, for example, diflufenican and propanil; arylcarboxylic acids such as, for example, dichloropicolinic acid, dicamba and picloram; aryloxy-alkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlorotoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuronethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulfosate and tridiphane.

The active compound according to the invention may also be present in its customary commercial formulations and in the use forms, prepared from these formulations, as a mixture with synergistic agents. Synergistic agents are compounds which increase the activity of the active compounds without it being necessary for the synergistic agent added to be active itself.

The active compound content of the use forms prepared from the customary commercial formulations can vary within wide limits. The active compound concentration of the use forms can be from 0.0000001 to 95% by weight of active compound, preferably between 0.0001 and 1% by weight.

The compounds are applied in a customary manner which is appropriate for the use forms.

When used against hygiene pests and pests of stored products, the active compound is distinguished by an outstanding residual action on wood and clay as well as by good stability to alkali on limed substrates.

The active compounds according to the invention are active not only against plant, hygiene and stored-product pests but also, in the veterinary sector, against animal parasites (ectoparasites) such as scaley ticks, argasidae, scab mites, trombidae, flies (stinging and sucking), parasitic fly larvae, lice, hair lice, bird lice and fleas. For example, they exhibit an outstanding activity against ticks such as, for example, *Boophilus microplus*.

The active compounds according to the invention of the formula (I) are also suitable for controlling arthropods which infest useful animals in agriculture, such as, for example, cattle, sheep, goats, horses, pigs, donkeys, camels, buffalo, rabbits, chickens, turkeys, ducks, geese, bees, other pets, for example, dogs, cats, cage birds, aquarium fish, and so-called experimentation animals, such as hamsters, guinea pigs, rats and mice. By controlling these arthropods the intention is to reduce the occurrence of fatalities and of reductions in yield (of meat, milk, wool, skins, eggs, honey, etc.), so that the use of the active compounds according to the invention enables the keeping of animals to be more economic and more simple.

In the veterinary sector, the active compounds according to the invention are employed in a known manner by enteral administration in the form, for example, of tablets, capsules, drinks, drenches, granules, pastes, boli, by the feed-through method, as suppositories, or by parenteral administration, for example by injection (intramuscular, subcutaneous, intravenous, intraperitoneal, etc), implants, by nasal application, by dermal application in the form, for example, of dipping or bathing, spraying, pouring on and spotting on, washing, powdering and with the aid of shaped articles which contain active compound, such as collars, ear tags, tail tags, limb bands, halters, marking devices, etc.

When used for cattle, birds, pets, etc, the active compounds of the formula (I) can be employed as formulations (for example powders, emulsions, flowable compositions) comprising the active compounds in a quantity of from 1 to 80% by weight, directly or after dilution by a factor of from 100 to 10,000, or they can be used as a chemical bath.

The preparation and use of the substances according to the invention is illustrated by the examples which follow.

PREPARATION EXAMPLES

Examples I-1B-a-1

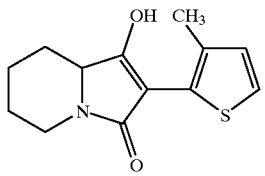

15.52 g (0.14 mol) of potassium tert-butylate (95% pure) are placed in 40 ml of anhydrous tetrahydrofuran. Under reflux, a solution of 18.6 g of ethyl N-[2-(3-methyl)-thienyl]-acetyl-piperidine-2-carboxylate according to Example (II-1) in 120 ml of anhydrous toluene is added dropwise, and stirring is continued under reflux for 1.5 h. The reaction mixture is cooled, 170 ml of water are added, the toluene phase is separated off, and extraction is carried out with 85 ml of water. The combined aqueous phases are acidified at from 0 to 10° C. with about 22 ml of concentrated hydrochloric acid, and the precipitate is filtered off with suction and dried. In this way, 14.3 g ($\approx$92% of theory) are obtained of the compound shown above, of melting point 159° C.

The substances of the formula I-1-a listed in the table are obtained similarly to Example I-1 A-a-1 or in accordance with the general preparation instructions:

Example I-1 B-b-1

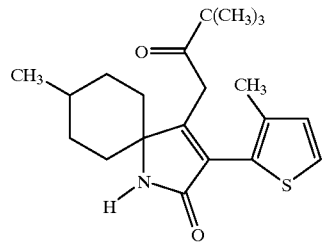

I-1 B-b-1

0.51 g (5 mmol) of triethylamine and a small spatula tip of diazabicyclooctane (DABCO) are added to a solution of 1.39 g (5 mmol) of the compound according to Example I-1 B-a-3 in 50 ml of dichloromethane. 0.6 g (5 mmol) of pivaloyl chloride is subsequently added dropwise at from 0 to 10° C. The mixture is stirred at room temperature for 15 minutes and hydrolysed with 5 ml of 10% NaOH, the phases are separated and the organic phase is washed with water. It is dried over magnesium sulfate, filtered and concentrated by evaporation.

Yield: 1.36 g (75% of theory) of a brown solid of melting point 184° C.

The compounds of the formula I-1-b listed in Table 2 are obtained analogously or in accordance with the general preparation instructions:

TABLE 1

I-1-a

| Ex. No. | B | A | D | $X_n$ | m.p. ° C. | Isomer |
|---|---|---|---|---|---|---|
| I-1 B-a-2 | H | —CH$_2$—CHCH$_3$—CHCH$_3$— | | 3-CH$_3$ | 140 | — |
| I-1 B-a-3 | | —(CH$_2$)$_2$—CHCH$_3$—(CH$_2$)— | H | 3-CH$_3$ | 235 | β |
| I-1 B-a-4 | | —(CH$_2$)$_3$—CHCH$_3$—CH$_2$— | H | 3-CH$_3$ | 118 | β |
| I-1 B-a-5 | | —(CH$_2$)$_5$— | H | 3-CH$_3$ | 202 | — |
| I-1 B-a-6 | | —(CH$_2$)$_2$—CHC$_3$H$_7$—(CH$_2$)$_2$— | H | 3-CH$_3$ | 216 | β |
| I-1 A-a-7 | | —(CH$_2$)$_5$— | H | 2,5-Di-CH$_3$ | 185–190 | — |
| I-1 A-a-8 | | —(CH$_2$)$_3$—CHCH$_3$—CH$_2$— | H | 2,5-Di-CH$_3$ | 237–240 | |
| I-1 A-a-9 | | —(CH$_2$)$_2$—CHCH$_3$—(CH$_2$)$_3$— | H | 2,5-Di-CH$_3$ | 257 | |

TABLE 2

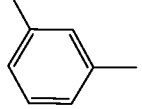

I-1-b

| Ex. No. | B | A | D | $X_n$ | $R^1$ | m.p. °C. |
|---|---|---|---|---|---|---|
| I-1 B-b-2 | —(CH$_2$)$_2$—CHCH$_3$—(CH$_2$)$_2$— | | H | 3-CH$_3$ | 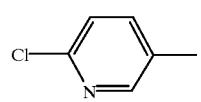 | 190 |
| I-1 B-b-3 | —(CH$_2$)$_2$—CHCH$_3$—(CH$_2$)$_2$— | | H | 3-CH$_3$ |  | 185 |
| I-1 B-b-4 | —(CH$_2$)$_2$—CHCH$_3$—(CH$_2$)$_2$— | | H | 3-CH$_3$ | 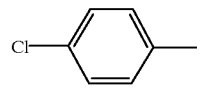 | 182 |
| I-1 B-b-5 | —(CH$_2$)$_2$—CHCH$_3$—(CH$_2$)$_2$— | | H | 3-CH$_3$ | 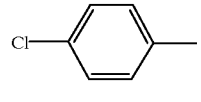 | 188 |
| I-1 B-b-6 | —(CH$_2$)$_2$—CHCH$_3$—(CH$_2$)$_2$— | | H | 3-CH$_3$ | CH$_3$ | 137 |
| I-1 B-b-7 | —(CH$_2$)$_2$—CHCH$_3$—(CH$_2$)$_2$— | | H | 3-CH$_3$ | Cl—CH$_2$—C(CH$_3$)$_2$— | 206 |
| I-1 B-b-8 | —(CH$_2$)$_3$—CHCH$_3$—CH$_2$— | | H | 3-CH$_3$ | (CH$_3$)$_3$C— | 139 |
| I-1 B-b-9 | —(CH$_2$)$_3$—CHCH$_3$—CH$_2$— | | H | 3-CH$_3$ | 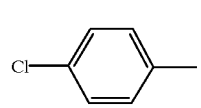 | 200 |
| I-1 B-b-10 | —(CH$_2$)$_3$—CHCH$_3$—CH$_2$— | | H | 3-CH$_3$ | 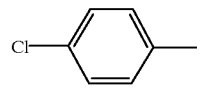 | 1) |
| I-1 B-b-11 | H | —(CH$_2$)$_4$— | | 3-CH$_3$ | C$_2$H$_5$—O—CH$_2$— | oil |
| I-1 B-b-12 | H | —(CH$_2$)$_4$— | | 3-CH$_3$ | t-C$_4$H$_9$— | oil |
| I-1 B-b-13 | H | —CH$_2$—CHCH$_3$—CHCH$_3$— | | 3-CH$_3$ | t-C$_4$H$_9$— | oil |
| I-1 B-b-14 | H | —CH$_2$—CHCH$_3$—CHCH$_3$— | | 3-CH$_3$ | 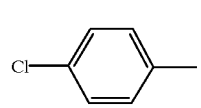 | oil |

1) $^1$H-NMR (CDCl$_3$, 300 MHz): δ = 2.18 ppm (s, 3H, thiophene-CH$_3$), 6.85 ppm (d, 1H, thiophene-4H), 7.27 ppm (d, 1H, thiophene-5H).

Example I-1 B-c-1

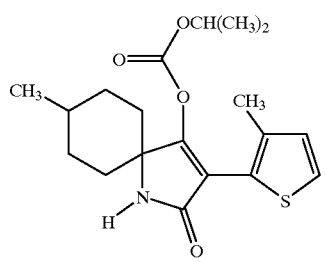

0.51 g (5 mmol) of triethylamine and a small spatula tip of DABCO are added to a solution of 1.39 g (5 mmol) of the compound according to Example I-1 B-a-3 in 50 ml of dichloromethane. 0.61 g (5 mmol) of isopropyl chloroformate in 5 ml of toluene is subsequently added dropwise at from 0 to 10° C. The mixture is stirred at room temperature for 15 minutes. A further 1.0 ml of 1.0 M isopropyl chloroformate in toluene (=0.12 g; 1.0 mmol) and 0.1 ml (0.1 g; 1.0 mmol) of triethylamine are added subsequently. The mixture is stirred at room temperature for a further 15 minutes and hydrolyzed with 5 ml of water, and the organic phase is separated off, dried over MgSO$_4$, filtered and concentrated.

Yield: 1.58 g of a reddish brown solid (87% of theory) of melting point 196° C.

The following compounds of the formula I-1-c are obtained analogously or according to the general preparation instructions:

TABLE 3

I-1-c

| Ex. No. | B | A | D | X$_n$ | R$^2$ | m.p. ° C. |
|---|---|---|---|---|---|---|
| I-1 B-c-2 | —(CH$_2$)$_2$—CHCH$_3$—(CH$_2$)$_2$— | | H | 3-CH$_3$ | benzyl (CH$_2$-C$_6$H$_5$) | 99 |
| I-1 B-c-3 | H | —(CH$_2$)$_4$— | | 3-CH$_3$ | C$_2$H$_5$— | oil |
| I-1 B-c-4 | —(CH$_2$)$_2$—CHCH$_3$—(CH$_2$)$_2$— | | H | 3-CH$_3$ | phenyl (C$_6$H$_5$) | 205 |

Example I-1 B-g-1

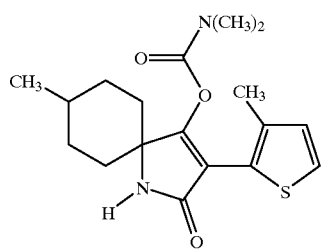

0.51 g (5 mmol) of triethylamine and a small spatula tip of DABCO are added to a solution of 1.39 g (5 mmol) of the compound according to Example I-1 B-a-3 in 50 ml of dichloromethane. 0.88 g (8.2 mmol) of N,N-dimethylcarbamoyl chloride is subsequently added dropwise at from 0 to 10° C. The mixture is stirred at room temperature for 15 minutes and hydrolyzed with 5 ml of 10% NaOH, the phases are separated and the organic phase is washed with water. It is dried over MgSO$_4$, filtered and concentrated. The crude product thus obtained is extracted by stirring with petroleum ether. The soluble portion is decanted off and concentrated by evaporation.

Yield: 1.70 g of a brown solid (98% of theory) of melting point 122° C. (decomposition).

Example (I-2 B-a-1)

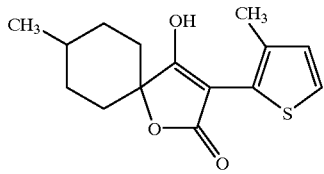

A solution of 3.0 g (9.68 mmol) of the compound according to Example (III-B-1) in 10 ml of dimethylformamide is added dropwise at from 0 to 10° C. to a solution of 1.68 g (15 mmol) of potassium tert-butylate in 10 ml of dimethylformamide. The mixture is stirred overnight, during which it is allowed to come to room temperature. 50 ml of 1N HCl are subsequently added dropwise with cooling. After 15 minutes the precipitate which has formed is filtered off with suction, washed well with water and dried.

Yield: 1.60 g (63% of theory) of pale yellow crystals of melting point 237° C.

| $^1$H-NMR (CDCl$_3$): | 2.30ppm(s, 3H, thienyl-C$\underline{H}_3$), 2.41ppm(s, 3H, thienyl-C$\underline{H}_3$), 6.59ppm(s, 1H, 4-thiophene-$\underline{H}$ |
|---|---|
| MS: | 278(M$^+$), 260, 178, 152, 109 |

The following compounds of the formula I-2-a are obtained analogously or according to the general preparation instructions:

TABLE 4

I-2-a

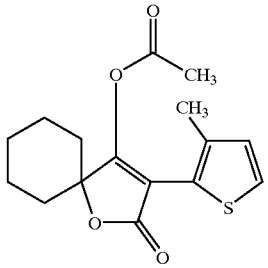

| Ex. No. | A | B | X$_n$ | m.p. ° C. |
|---|---|---|---|---|
| I-2 B-a-3 | | —(CH$_2$)$_2$—CHCH$_3$—(CH$_2$)$_2$— | 3-CH$_3$ | 210 |
| I-2 B-a-4 | | —(CH$_2$)$_2$—CHCH$_3$—CHCH$_3$—CH$_2$— | 3-CH$_3$ | 160 |
| I-2 B-a-5 | | —(CH$_2$)$_2$—CHOCH$_3$—(CH$_2$)$_2$— | 3-CH$_3$ | 158 |
| I-2 B-a-6 | | —(CH$_2$)$_5$— | 3-CH$_3$, 4.5-CH=CH—CH=CH— | 270 |
| I-2 A-a-7 | | —(CH$_2$)$_5$— | 4.5-CH=CCl—CH=CH— | 268 (decomp.) |
| I-2 B-a-8 | —CH$_3$ | —CH$_3$ | 3-CH$_3$ | 132–135 |
| I-2 B-a-9 | | —(CH$_2$)$_4$— | 3-CH$_3$ | 210 |
| I-2 A-a-10 | | —(CH$_2$)$_2$—CHOCH$_3$—(CH$_2$)$_2$— | 2.5-Di-CH$_3$ | 164 |
| I-2 A-a-11 | | —(CH$_2$)$_4$— | 2.5-Di-CH$_3$ | 204 |
| I-2 A-a-12 | | —(CH$_2$)$_2$—CHOCH$_3$—(CH$_2$)$_2$— | 2.5-Di-CH$_3$ | 187 |

| $^1$H-NMR (CDCl$_3$): | 2.15ppm(s, 3H, thienyl-C$\underline{H}_3$), 6.91ppm(d, 1H, 4-thiophene-$\underline{H}$, $^3$J=5.1Hz), 7.30ppm(d, 1H, 5-thiophene-$\underline{H}$, $^3$J=5.1Hz) |
|---|---|
| GC/MS (SIL): | 89.9%(index 2271; MS: 336(M$^+$), 246, 218, 203, 190, 109, 73, 45) |

Example (I-2 A-a-2)

(I-2 A-a-2)

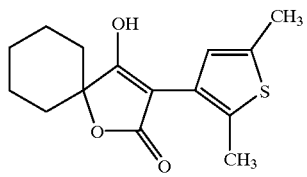

Working in accordance with Example (I-2 B-a-1) and starting from the compound according to Example (III-A-2), the compound shown above is obtained as pale yellow crystals of melting point 239° C. (decomposition).

Example (I-2 B-b-1)

(I-2 B-b-1)

A total of 0.48 g (4.8 mmol) of triethylamine, 0.40 g (5.1 mmol) of acetyl chloride and a small spatula tip of diazabicycloundecene (DABCO) are added to a solution of 1.0 g (3.79 mmol) of the compound according to the Example (I-2 B-a-1) in 10 ml of tetrahydrofuran, and the mixture is stirred at room temperature for about 2 days in all. It is then diluted with diethyl ether and washed free of salt with water. It is dried and concentrated in vacuo.

Yield: 1.0 g (86% of theory), melting point 203° C.

The following compounds of the formula I-b-2 are obtained analogously or in accordance with the general preparation instructions:

TABLE 5

I-2-b

| Ex. No. | A | B | $X_n$ | $R^1$ | m.p. °C. |
|---|---|---|---|---|---|
| I-2 B-b-2 | | —(CH$_2$)$_2$—CHCH$_3$—(CH$_2$)$_2$— | 3-CH$_3$ | (CH$_3$)$_3$C— | 83 |
| I-2 B-b-3 | | —(CH$_2$)$_2$—CHCH$_3$—(CH$_2$)$_2$— | 3-CH$_3$ |  | MS: M$^+$ 346, 137, 109, 69 |
| I-2 B-b-4 | | —(CH$_2$)$_2$—CHCH$_3$—(CH$_2$)$_2$— | 3-CH$_3$ |  | 115 |
| I-2 B-b-5 | | —(CH$_2$)$_2$—CHCH$_3$—CHCH$_3$—CH$_2$— | 3-CH$_3$ | (CH$_3$)$_3$C— | 103 |
| I-2 B-b-6 | | —(CH$_2$)$_2$—CHOCH$_3$—(CH$_2$)$_2$— | 3-CH$_3$ | (CH$_3$)$_3$C— | MS: M$^+$ 378, 294, 262, 57 |
| I-2 B-b-7 | | —(CH$_2$)$_5$— | 3-CH$_3$ | (CH$_3$)$_3$C— | 111 |
| I-2 B-b-8 | | —(CH$_2$)$_5$— | 3-CH$_3$ |  | 60 |
| I-2 B-b-9 | | —(CH$_2$)$_2$—CHOCH$_3$—(CH$_2$)$_2$— | 3-CH$_3$ |  | 119 |
| I-2 B-b-10 | | —(CH$_2$)$_5$— | 3-CH$_3$ | 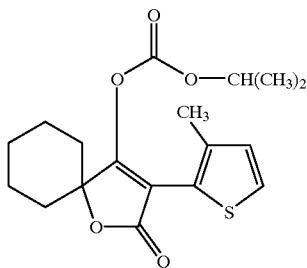 | 117 |
| I-2 B-b-11 | | —(CH$_2$)$_5$— | 3-CH$_3$ | Cl—CH$_2$—C(CH$_3$)$_2$— | 118 |
| I-2 B-b-12 | | —(CH$_2$)$_5$— | 4,5-CH=CCl—CH=CH— | (CH$_3$)$_3$C— | 139 |
| I-2 A-b-13 | | —(CH$_2$)$_5$— | 2,5-Di-CH$_3$ | (CH$_3$)$_3$C— | 88 |
| I-2 A-b-14 | | —(CH$_2$)$_2$—CHOCH$_3$—(CH$_2$)$_2$— | 2,5-Di-CH$_3$ | (CH$_3$)$_3$C— | oil |

Example (I-2 B-c-1)

(I-2 B-c-1)

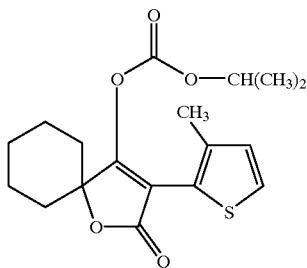

0.38 g (3.8 mmol) of triethylamine and a small spatula tip of DABCO are added to a solution of 1.0 g (3.79 mmol) of the compound according to Example (I-2 B-a-1) in 10 ml of tetrahydrofuran. 0.47 g (3.8 mmol) of isopropyl chloroformate is subsequently added dropwise at room temperature. The mixture is stirred at room temperature overnight, diluted with diethyl ether, washed free of salt with water, dried and concentrated.

Yield: 1.40 g (85% of theory) of an oil.

| $^1$H-NMR (CDCl$_3$): | 1.17ppm(d, 6H, —OCH(C$\underline{H}_3$)$_2$, $^3$J=6.3Hz), 2.18 ppm(s, 3H, thienyl-C$\underline{H}_3$), 4.76ppm(m, 1H, -OCH(C$\underline{H}_3$)$_2$), 6.87ppm(d, 1H, 4-thiophene-$\underline{H}$, $^3$J= 5.1Hz), 7.33ppm(d, 1H, 5-thiophene-$\underline{H}$, $^3$J= 5.1Hz) |
|---|---|
| GC/MS (SIL): | 81.4%(index 2343; MS: 350(M$^+$), 264, 241, 219, 164, 109, 43) |

The following compounds of the formula I-2-c are obtained analogously or in accordance with the general preparation instructions:

TABLE 6

I-2-c

[Structure diagram of I-2-c compound]

| Ex. No. | A | B | $X_n$ | M | $R^2$ | m.p. ° C. |
|---------|---|---|-------|---|-------|-----------|
| I-2 B-c-2 | —(CH$_2$)$_2$—CHCH$_3$—(CH$_3$)$_2$— | | 3-CH$_3$ | O | (CH$_3$)$_2$CH— | MS: M$^+$ 364, 278, 260, 123 |
| I-2 B-c-3 | —(CH$_2$)$_2$—CHCH$_3$—CHCH$_3$—CH$_2$— | | 3-CH$_3$ | O | (CH$_3$)$_2$CH— | MS: M$^+$ 378, 292, 274, 137 |
| I-2 B-c-4 | —(CH$_2$)$_3$—CHCH$_3$—CH$_2$— | | 3-CH$_3$ | O | (CH$_3$)$_2$CH— | 178 |
| I-2 A-c-5 | —(CH$_2$)$_5$— | | 4,5- [Cl-substituted diene group] | O | (CH$_3$)$_2$CH— | 135 (decomp.) |
| I-2 A-c-6 | —(CH$_2$)$_5$— | | 2,5-Di-CH$_3$ | O | (CH$_3$)$_2$CH— | MS: M$^+$ 346, 260, 178, 59 |
| I-2 A-c-7 | —(CH$_2$)$_2$—CHOCH$_3$—(CH$_2$)$_2$— | | 3-CH$_3$ | O | (CH$_3$)$_2$CH— | oil |
| I-2 A-c-8 | —(CH$_2$)$_2$—CHOCH$_3$—(CH$_2$)$_2$— | | 2,5-Di-CH$_3$ | O | (CH$_3$)$_2$CH— | oil |

Preparation of the Starting Materials

Example (II-B-1)

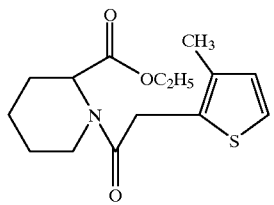

II-B-1

A solution of 11.1 g of the compound according to Example (XXIV-1) in 50 ml of tetrahydrofuran (THF) is added dropwise at from 0° C. to 10° C. to a mixture of 10.1 ml of ethyl piperidine-2-carboxylate and 9 ml (0.641 mol) of triethylamine in 100 ml of THF. The mixture is stirred at room temperature for 1 hour, filtered with suction, the solid washed with THF and the filtrate concentrated by evaporation. The residue is taken up in CH$_2$Cl$_2$, washed with 0.5N HCl, dried and concentrated by evaporation.

Yield: 18.6 g (95% of theory) of a brown oil.

The following compounds of the formula (II) were obtained analogously to Example (II-B-1):

(II)

[Structure of formula (II)]

| Ex. No. | B | A | D | $X_n$ | $R^8$ | m.p. ° C. |
|---------|---|---|---|-------|-------|-----------|
| II-B-2 | H | | —CH$_2$—CHCH$_3$—CHCH$_3$— | 3-CH$_3$ | C$_2$H$_5$ | oil |
| II-B-3 | H | | —CH$_2$—S—(CH$_2$)$_2$— | 3-CH$_3$ | C$_2$H$_5$ | oil |

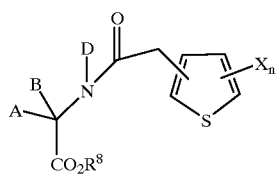

(II)

| Ex. No. | B | A | D | $X_n$ | $R^8$ | m.p. ° C. |
|---|---|---|---|---|---|---|
| II-B-4 | —(CH$_2$)$_2$—CHCH$_3$—(CH$_2$)$_2$— | | H | 3-CH$_3$ | CH$_3$ | 108 |
| II-B-5 | —(CH$_2$)$_3$—CHCH$_3$—CH$_2$— | | H | 3-CH$_3$ | CH$_3$ | 98 |
| II-B-6 | —(CH$_2$)$_5$— | | H | 3-CH$_3$ | CH$_3$ | 102 |
| II-B-7 | —(CH$_2$)$_2$—CHC$_3$H$_7$—(CH$_2$)$_2$— | | H | 3-CH$_3$ | CH$_3$ | 101 |
| II-A-8 | —(CH$_2$)$_5$— | | H | 2.5-Di-CH$_3$ | CH$_3$ | 85 |
| II-A-9 | —(CH$_2$)$_3$—CHCH$_3$—CH$_2$— | | H | 2.5-Di-CH$_3$ | CH$_3$ | 107 |
| II-A-10 | —(CH$_2$)$_2$—CHCH$_3$—(CH$_2$)$_2$— | | H | 2.5-Di-CH$_3$ | CH$_3$ | 111 |

Example (III-B-1)

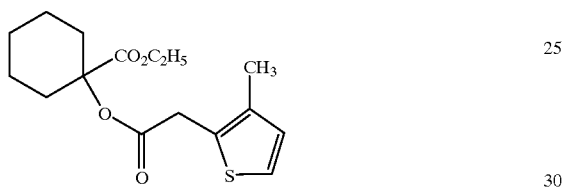

(III-B-1)

6.88 g (40 mmol) of ethyl 1-hydroxycyclohexanecarboxylate are added dropwise at room temperature to a solution of 6.90 g (39.5 mmol) of a compound according to Example (XXIV)-1 in 60 ml of dichloromethane and the mixture is stirred under reflux overnight. It is then concentrated and the residue is chromatographed through silica gel (with petroleum ether/acetone 9:1).

Yield: 7.80 g (63% of theory) of an oil.

| $^1$H-NMR (CDCl$_3$): | 2.21 ppm(s, 3H, thienyl-C$\underline{H}_3$), 3.77 ppm(s, 2H, thienyl-C$\underline{H}_2$-), 6.82 ppm(d, 1H, 4-thiophene-$\underline{H}$, $^3$J= 5.1 Hz), 7.10 ppm(d, 1H, 5-thiophene-$\underline{H}$, $^3$J= 5.1 Hz) |
|---|---|
| GC/MS (SIL): | 70.2% (index 2016; MS: 310 (M$^+$), 155, 138, 111, 81, 29) |

Example (III-A-2)

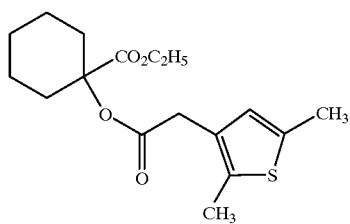

(III-A-2)

| $^1$H-NMR (CDCl$_3$): | 3.50ppm(s, 2H, thienyl-C$\underline{H}_2$—), 6.55ppm(d, 1H, 4-thiophene-$\underline{H}$) |
|---|---|
| GC/MS (SIL): | 38.0%(index 2074; MS: 324(M$^+$), 169, 152, 125, 81) |

The compound (III-A-2) shown above is obtained analogously.

The following compounds of the formula (III) were obtained analogously to Examples (III-B-1) and (III-A-2):

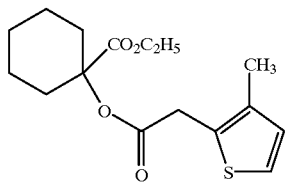

(III)

| Ex. No. | A | B | $X_n$ | $R^8$ | physical constant |
|---|---|---|---|---|---|
| III-B-3 | | —(CH$_2$)$_2$—CHCH$_3$—(CH$_2$)$_2$— | 3-CH$_3$ | C$_2$H$_5$ | |
| III-B-4 | | —(CH$_2$)$_2$—CHCH$_3$—CHCH$_3$—CH$_2$— | 3-CH$_3$ | C$_2$H$_5$ | |
| III-B-5 | | —(CH$_2$)$_2$—CHOCH$_3$—(CH$_2$)$_2$— | 3-CH$_3$ | C$_2$H$_5$ | |
| III-B-6 | | —(CH$_2$)$_5$— | 3-CH$_3$, 4.5-CH=CH—CH=CH— | C$_2$H$_5$ | |
| III-B-7 | | —(CH$_2$)$_5$— | 4.5-CH=CCl—CH=CH— | C$_2$H$_5$ | |
| III-B-8 | —CH$_3$ | —CH$_3$ | 3-CH$_3$ | C$_2$H$_5$ | GC/MS M$^+$ 270, 138, 111, 59 |
| III-B-9 | | —(CH$_2$)$_4$— | 3-CH$_3$ | C$_2$H$_5$ | GC/MS M$^+$ 296, 138, 111, 67 |
| III-A-10 | | —(CH$_2$)$_2$—CHOCH$_3$—(CH$_2$)$_2$— | 2.5-Di-CH$_3$ | C$_2$H$_5$ | GC/MS M$^+$ 354, 170, 169, 153, 152 |
| III-A-11 | | —(CH$_2$)$_4$— | 2.5-Di-CH$_3$ | C$_2$H$_5$ | |
| III-A-12 | | —(CH$_2$)$_2$—CHCH$_3$—(CH$_2$)$_2$— | 2.5-Di-CH$_3$ | C$_2$H$_5$ | |

The compounds in the table were obtained as brown oils.

Example (XXIV-1)

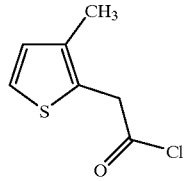

(XXIV-1)

6.1 g (48 mmol) of oxalyl chloride are added dropwise at room temperature to a solution of 6.30 g (40.4 mmol) of the compound of the formula

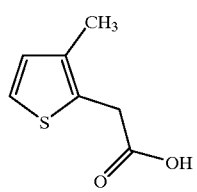

(XXX-1)

in 50 ml of dichloromethane. The mixture is stirred overnight and then concentrated in vacuo.

Yield: 6.90 g (99% of theory) of an oil.

The crude product obtained in this way was not purified further.

Example (XXX-1)

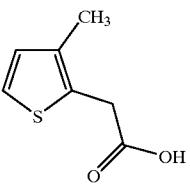

(XXX-1)

A solution of the compound according to Example (XXXII-1) in 500 ml of 10% strength aqueous KOH is heated at reflux for 3 hours. It is cooled, diluted with water and acidified with concentrated hydrochloric acid while cooling with ice. The aqueous solution is extracted several times with dichloromethane; the organic phase is dried over MgSO$_4$ and filtered. The solvent is then removed in vacuo.

Yield: 35.0 g of orange crystals (95% of theory).

$^1$H-NMR (CDCl$_3$): 2.81 ppm(s, 3H, thienyl-C$\underline{H}_3$), 3.77 ppm(s, 2H, thienyl-C$\underline{H}_2$-), 6.83 ppm(d, 1H, 4-thiophene-$\underline{H}$, $^3J=$ 5.1 Hz), 7.13 ppm(d, 1H, 5-thiophene-$\underline{H}$, $^3J=$ 5.1 Hz)

Example (XXXII-1)

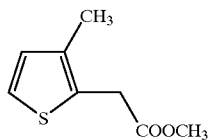

46.1 g (0.587 mol) of acetyl chloride are added dropwise to 500 ml of methanol while cooling with ice. To the resulting solution is added dropwise, at room temperature, a solution of 56.0 g (0.191 mol) of the compound of the formula

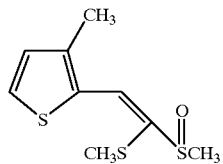

in 100 ml of methanol. The mixture is stirred at room temperature overnight and concentrated and the residue is taken up in ether and washed several time with aqueous sodium hydrogen carbonate solution. The organic phase is subsequently dried and concentrated.

Yield: 35.0 g of an orange oil (100% of theory, based on 3-methyl-2-thiophenecarbaldehyde).

| $^1$H-NMR (CDCl$_3$): | 2.18ppm(s, 3H, thienyl-C$\underline{H}_3$), 3.71ppm(s, 3H, -COOC$\underline{H}_3$), 3.74ppm(s, 2H, thienyl-C$\underline{H}_2$—), 6.82 ppm(d, 1H, 4-thiophene-$\underline{H}$, $^3$J=5.1Hz), 7.11ppm (d, 1H, 5-thiophene-$\underline{H}$, $^3$J=5.1Hz) |
|---|---|

Preparation of the Precursor Required for Example (XXXII-1)

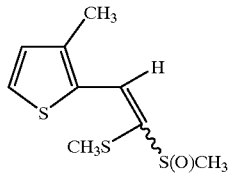

37.5 g (0.300 mol) of methyl methylmercaptomethyl sulfoxide and 134 g (0.320 mol) of benzyltrimethylammonium hydroxide, 40% in MeOH (=Triton B), are added to a solution of 27.9 g (0.200 mol) of 3-methyl-2-thiophenecarbaldehyde in 80 ml of dry tetrahydrofuran. The mixture is heated under reflux for 14 hours and then concentrated. The residue which remains is taken up in dichloromethane and washed twice with 100 ml of 1N sulfuric acid each time. The organic phase is dried, filtered and concentrated by evaporation in vacuo.

Yield: 56.0 g of a dark brown liquid (crude product).

| GC/MS: | 71.5% isomer A (index 1964); MS: 232 (M$^+$), 169, 153, 121 |
|---|---|
| | 7.6% isomer B (index 1991); MS: 232 (M$^+$), 169, 154, 141 |

Example (XXX-2)

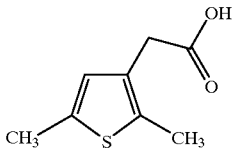

69.0 g (270 mmol) of 2,5-dimethyl-3-thienylacetic acid thiomorpholinide in 147 ml of 50% aqueous NaOH and 500 ml of analytical-grade methanol are heated under reflux for 5 hours. The methanol is removed by distillation, and the mixture is diluted with water and acidified with dilute hydrochloric acid. The oily solid obtained in this way is filtered off with suction, taken up in dichloromethane and dried over magnesium sulfate. The aqueous phase is extracted several times with dichloromethane and the combined organic phases are dried over magnesium sulfate and then concentrated. In order to purify the residue further it is dissolved in 10% strength of NaOH and extracted with ether, the extracts are acidified with dilute hydrochloric acid and subjected to extraction with dichloromethane, and these extracts are dried, filtered and concentrated.

Yield: 36.0 g of a brown solid (78% of theory).

| $^1$H-NMR (CDCl$_3$): | 2.32 ppm(s, 3H, thienyl-C$\underline{H}_3$), 2.39 ppm(s, 3H, thienyl-C$\underline{H}_3$), 3.50 ppm(s, 2H, thienyl-C$\underline{H}_2$-), 6.55 ppm(s, 1H, 4-thiophene-$\underline{H}$). |
|---|---|
| GC/MS (SIL): | 93% (index 1434; MS: 242 (M$^+$; SIL), 227, 198, 125, 125, 73, 45 |

2,5-Dimethyl-3-thienylacetic acid thiomorpholinide

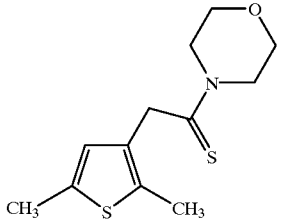

10.0 g (64.8 mmol) of 3-acetyl-2,5-dimethylthiophene, 13.0 ml (13.0 g; 149 mmol) of morpholine and 3.49 g (109 mmol) of sulfur are heated under reflux for 16 hours. The mixture is cooled, poured into 20 ml of ethanol and concentrated, water is added, and the mixture is extracted with dichloromethane. Drying over magnesium sulfate, filtration and concentration gives 16.6 g of an oil which is purified by column chromatography on silica gel with dichloromethane/ethyl acetate 1:1.

Yield: 12.5 g of a reddish brown solid (75% of theory).

| | |
|---|---|
| $^1$H-NMR (CDCl$_3$): | 2.30ppm(s, 3H, thienyl-C$\underline{H}_3$), 2.37ppm(s, 3H, thienyl-C$\underline{H}_3$), 3.46ppm(m, 2H, morpholine-C$\underline{H}_2$), 3.59ppm(m, 2H, morpholine-C$\underline{H}_2$), 3.76ppm(m, 2H, morpholine-C$\underline{H}_2$), 4.09ppm(s, 2H, thienyl-C$\underline{H}_2$—), 4.37ppm(m, 2H, morpholine-C$\underline{H}_2$), 6.60ppm(s, 1H, 4-thiophene-$\underline{H}$). |
| GC/MS: | 85%(index 2113); MS: 255(M$^+$), 222, 168, 125, 86, 59, 28. |

Use Examples

Example A

Tetranychus test (OP-resistant/spray treatment)

Solvent: 3 parts by weight of dimethylformamide

Emulsifier: 1 part by weight of alkylaryl polyglycol ether

To prepare a suitable preparation of active compound, 1 part by weight of active compound is mixed with the stated amount of solvent and with the stated amount of emulsifier, and the concentrate is diluted with water to the desired concentration.

Bean plants (*Phaseolus vulgaris*) which are heavily infested by all development stages of the common spider mite or red spider mite (*Tetranychus urticae*) are treated by being dipped into the active compound preparation at the desired concentration.

After the desired time, the destruction is determined in %. In this context, 100% means that all of the mites have been killed; 0% means that none of the mites have been killed.

In this test, for example, the compounds according to Preparation Examples I-2 Ba-1 and I-2 Bc-1, at an active compound concentration of 0.1%, which was chosen by way of example, brought about a destruction of at least 98% after 7 days.

Example B

Test with Boophilus microplus resistant/SP resistant Parkhurst strain

Test organisms: adult sucked-up females

Solvent: dimethyl sulfoxide 20 mg of active compound are dissolved in 1 ml of dimethyl sulfoxide; lower concentrations are prepared by dilution with the same solvent.

The test is carried out in 5-fold determinations. 1 μl of the solutions is injected into the abdomen, and the organisms are transferred to dishes and kept in a climate-controlled area. The activity is monitored, after 7 days, by inhibition of ovipoisition. An activity of 100% indicates that none of the ticks laid eggs.

In this test, for example, the compounds according to Preparation Examples I-2 B-a-1, I-2 B-b-1 and I-2 B-c-1 showed an activity of 100% at an active compound concentration, chosen by way of example, of 20 μg/organism.

We claim:

1. A compound of the formula (I)

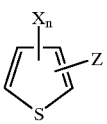

(I)

in which

X represents halogen, alkyl, alkoxy, alkylthio, halogenoalkyl, halogenoalkoxy, nitro or cyano, or two substituents X together with the carbon atoms to which they are attached, form a saturated or unsaturated, optionally substituted ring, n represents 1, 2 or 3, and Z represents

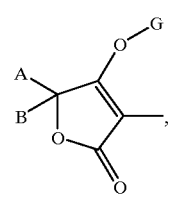

(2)

in which

A represents hydrogen, optionally halogen-substituted alkyl, alkenyl, alkoxyalkyl, alkylthioalkyl, saturated or unsaturated, optionally substituted cycloalkyl which is optionally interrupted by at least one heteroatom, or represents aryl, arylalkyl, or hetaryl each of which is optionally substituted by halogen, alkyl, halogenoalkyl, alkoxy or nitro, B represents hydrogen, alkyl or alkoxyalkyl, or A and B, together with the carbon atom to which they are attached, represent a saturated or unsaturated, unsubstituted or substituted ring which is optionally interrupted by at least one heteroatom, G represents hydrogen (a) or one of the groups

(b)

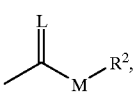

(c)

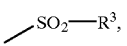

(d)

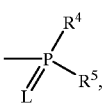

(e)

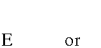

(f)

E or

-continued

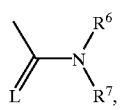
(g)

in which
E represents a metal ion equivalent or an ammonium ion,
L represents oxygen or sulfur,
M represents oxygen or sulfur,
R¹ represents in each case optionally halogen-substituted alkyl, alkenyl, alkoxyalkyl, alkylthioalkyl, polyalkoxyalkyl or cycloalkyl which is optionally substituted by halogen, alkyl or alkoxy and may be interrupted by at least one heteroatom, or represents in each case optionally substituted phenyl, phenylalkyl, hetaryl, phenoxyalkyl or hetaryloxyalkyl,
R² represents in each case optionally halogen-substituted alkyl, alkenyl, alkoxyalkyl, polyalkoxyalkyl or in each case optionally substituted cycloalkyl, phenyl or benzyl,
R³, R⁴ and R⁵, independently of one another, represent in each case optionally halogen-substituted alkyl, alkoxy, alkylamino, dialkylamino, alkylthio, alkenylthio, cycloalkylthio and in each case optionally substituted phenyl, phenylalkyl, phenoxy or phenylthio,
R⁶ and R⁷, independently of one another, represent hydrogen, in each case optionally halogen-substituted alkyl, cycloalkyl, alkenyl, alkoxy, alkoxyalkyl, optionally substituted phenyl, optionally substituted benzyl, or represent, together with the nitrogen atom to which they are attached, a ring which is optionally-interrupted by oxygen or sulfur.

2. A compound of the formula (I) as claimed in claim 1, in which
X represents halogen, C₁–C₆-alkyl, C₁–C₆-alkoxy, C₁–C₆-alkylthio, C₁–C₆-halogenoalkyl, C₁–C₆-halogenoalkoxy, nitro or cyano
or two substituents X, together with the carbon atoms to which they are attached, form a saturated-or unsaturated 5- to 8-membered carbocyclic ring which is optionally substituted by halogen, C₁–C₆-alkyl, C₁–C₆-alkoxy, C₁–C₆-halogenoalkyl, C₁–C₆-halogenoalkoxy, nitro or cyano,
n represents 1, 2 or 3,
Z represents

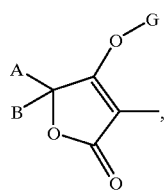
(2)

A represents hydrogen or in each case optionally halogen-substituted C₁–C₁₂-alkyl, C₂–C₈-alkenyl, C₁–C₁₀-alkoxy-C₁–C₈-alkyl, poly-C₁–C₈-alkoxy-C₁–C₈-alkyl, C₁–C₁₀-alkylthio-C₁–C₆-alkyl, cycloalkyl having 3 to 8 ring atoms which is optionally substituted by C₁–C₆-alkyl, halogen or C₁–C₆-alkoxy and in which, optionally, one or two methylene groups which are not directly adjacent are replaced by oxygen and/or sulfur, or represents C₆- or C₁₀-aryl, hetaryl having 5 to 6 ring atoms and one to three heteroatoms from the series consisting of nitrogen, oxygen and sulfur, or C₆-or C₁₀-aryl-C₁–C₆-alkyl, each of which is optionally substituted by halogen, C₁–C₆-alkyl, C₁–C₆-halogenoalkyl, C₁–C₆-alkoxy or nitro,
B represents hydrogen, C₁–C₁₂-alkyl or C₁–C₈-alkoxy-C₁–C₆-alkyl, or
A, B and the carbon atom to which they are attached represent a saturated or unsaturated C₃–C₁₀ spirocyclic system in which, optionally, one or two methylene groups which are not directly adjacent are replaced by oxygen and/or sulfur and which is optionally substituted by C₁–C₈-alkyl; C₃–C₁₀-cycloalkyl, C₁–C₈-halogenoalkyl, C₁–C₈-alkoxy, C₁–C₈-alkylthio, halogen or phenyl, or
A, B and the carbon atom to which they are attached represent a C₃–C₆ spirocyclic ring system which is substituted by an alkylenediyl group, optionally interrupted by one or two oxygen and/or sulfur atoms, or is substituted by an alkylenedioxy or by an alkylenedithio group, which, with the carbon atom to which it is attached, forms a further five- to eight-membered spirocyclic ring system, or
A, B and the carbon atom to which they are attached represent a C₃–C₈ spirocyclic ring system in which two substituents together represent a saturated or mono- or polyunsaturated 5- to 8-membered ring which is optionally substituted by C₁–C₆-alkyl, C₁–C₆-alkoxy or halogen and which optionally contains an oxygen or sulfur atom,
G represents hydrogen (a) or represents one of the groups (b)

(c)
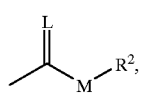

(d)
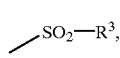

(e)
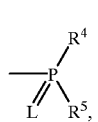

(f)
E or (g)
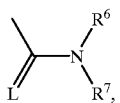

in which
E represents a metal ion equivalent or an ammonium ion,
L represents oxygen or sulfur, and
M represents oxygen or sulfur,
R¹ represents in each case optionally halogen-substituted C₁–C₂₀-alkyl, C₂–C₂₀-alkenyl, C₁–C₈-alkoxy-C₁–C₈- alkyl, $C_1–C_8$-alkylthio-$C_1–C_8$-alkyl, poly-$C_1–C_8$-alkoxy-$C_1–C_8$-alkyl, or represents cycloalkyl having 3 to 8 ring atoms which is optionally substituted by halogen or $C_1–C_6$-alkyl and in which, optionally, one or two methylene groups which are not directly adjacent are replaced by oxygen and/or sulfur, or represents phenyl which is optionally substituted by halogen, nitro, $C_1–C_6$-alkyl, $C_1–C_6$-alkoxy, $C_1–C_6$-halogenoalkyl, $C_1–C_6$-halogenoalkoxy, $C_1–C_6$-alkylthio or $C_1–C_6$-alkylsulfonyl, or represents phenyl-$C_1–C_6$-alkyl which is optionally substituted by halogen, $C_1–C_6$-alkyl, $C_1–C_6$-alkoxy, $C_1–C_6$-halogenoalkyl or $C_1–C_6$-halogenoalkoxy, or represents 5- or 6-membered hetaryl having one to three heteroatoms from the series consisting of nitrogen, oxygen and sulfur, which is optionally substituted by halogen or $C_1–C_6$-alkyl, or represents phenoxy-$C_1–C_6$-alkyl which is optionally substituted by halogen or $C_1–C_6$-alkyl, or represents 5- or 6-membered hetaryloxy-$C_1–C_6$-alkyl having one to three heteroatoms from the series consisting of nitrogen, oxygen and sulfur, which is optionally substituted by halogen, amino or $C_1–C_6$-alkyl, $R^2$ represents in each case optionally halogen-substituted $C_1–C_{20}$-alkyl, $C_3–C_{20}$alkenyl, $C_1–C_8$-alkoxy-$C_1–C_8$-alkyl or poly- $C_1–C_8$-alkoxy-$C_1–C_8$-alkyl, or represents $C_3–C_8$-cycloalkyl which is optionally substituted by halogen, $C_1–C_4$-alkyl or $C_1–C_4$-alkoxy, or represents phenyl or benzyl each of which is optionally substituted by halogen, nitro, $C_1–C_6$-alkyl, $C_1–C_6$-alkoxy or $C_1–C_6$-halogenoalkyl, $R^3$ represents optionally halogen-substituted $C_1–C_8$-alkyl or represents benzyl or phenyl each of which is optionally substituted by halogen, $C_1–C_6$-alkyl, $C_1–C_6$-alkoxy, $C_1–C_3$- halogenoalkyl, $C_1–C_3$-halogenoalkoxy, nitro or cyano, $R^4$ and $R^5$ represent, independently of one another, optionally halogen- substituted $C_1–C_8$-alkyl, $C_1–C_8$-alkoxy, $C_1–C_8$-alkylamino, di- ($C_1–C_8$-alkyl)-amino, $C_1–C_8$-alkylthio, $C_2–C_8$-alkenylthio, $C_3–C_7$-cycloalkylthio, or represent phenyl, phenoxy or phenylthio each of which is optionally substituted by halogen, nitro, cyano, $C_1–C_4$-alkoxy, $C_1–C_4$-halogenoalkoxy, $C_1–C_4$-alkylthio, $C_1–C_4$-halogenoalkylthio, $C_1–C_4$-alkyl or $C_1–C_4$-halogenoalkyl, $R^6$ and $R^7$, independently of one another, represent hydrogen, in each case optionally halogen-substituted $C_1–C_8$-alkyl, $C_3–C_8$-cycloalkyl, $C_1–C_8$-alkoxy, $C_3–C_8$-alkenyl, $C_1–C_8$-alkoxy-$C_1–C_8$-alkyl, phenyl which is optionally substituted by halogen, $C_1–C_8$-halogenoalkyl, $C_1–C_8$-alkyl or $C_1–C_8$-alkoxy, benzyl which is optionally substituted by halogen, $C_1–C_8$-alkyl, $C_1–C_8$- halogenoalkyl or $C_1–C_8$-alkoxy, or together represent $C_3–C_6$- alkanediyl in which, optionally, one methylene group is replaced by oxygen or sulfur, $R^{13}$ represents hydrogen, in each case optionally halogen-substituted $C_1–C_8$-alkyl, $C_1–C_8$-alkoxy or $C_3–C_8$-cycloalkyl, or represents phenyl or benzyl each of which is optionally substituted by halogen, $C_1–C_6$-alkyl, $C_1–C_6$-alkoxy, $C_1–C_3$- halogenoalkyl, $C_1–C_3$-halogenoalkoxy, nitro or cyano, $R^{14}$ and $R^{15}$ represent, independently of one another, hydrogen, $C_1–C_8$- alkyl, $C_1–C_8$-halogenoalkyl, $C_3–C_6$-cycloalkyl, or represents phenyl or benzyl each of which is optionally substituted by halogen, $C_1–C_6$-alkyl, $C_1–C_6$-alkoxy, $C_1–C_3$-halogenoalky, $C_1–C_3$-halogenoalkoxy, cyano or nitro, or together represent an optionally $C_1–C_4$-alkyl-substituted $C_4–C_6$-alkanediyl group, $R^{16}$ and $R^{17}$ are identical or different and represents $C_1–C_6$-alkyl, or $R^{16}$ and $R^{17}$ together represent a $C_2–C_4$-alkanediyl radical which is optionally substituted by $C_1–C_6$-alkyl or by phenyl which is optionally substituted by halogen, $C_1–C_4$-alkyl, $C_1–C_4$- halogenoalkyl, $C_1–C_4$-alkoxy, $C_1–C_4$-halogenoalkoxy, nitro or cyano, $R^{18}$ and $R^{19}$, independently of one another, represent hydrogen, optionally halogen-substituted $C_1–C_8$-alkyl, or phenyl which is optionally substituted by halogen, $C_1–C_6$-alkyl, $C_1–C_6$-alkoxy, $C_1–C_4$-halogenoalkyl, $C_1–C_4$-halogenoalkoxy, nitro or cyano, $R^{20}$ and $R^{21}$, independently of one another, represent $C_1–C_{10}$-alkyl, $C_3–C_{10}$- alkenyl, $C_1–C_{10}$-alkoxy, $C_1–C_{10}$-alkylamino, $C_3–C_{10}$-alkenyl- amino, di-($C_1–C_{10}$-alkyl)-amino or di-($C_3–C_{10}$-alkenyl)-amino.

3. A compound of the formula (I) as claimed in claim 1, in which

X represents fluorine, chlorine, bromine, $C_1–C_4$-alkyl, $C_1–C_4$-alkoxy, $C_1–C_4$-alkylthio, $C_1–C_4$-halogenoalkyl, $C_1–C_4$-halogenoalkoxy, nitro or cyano or two substituents X, form, together with the carbon atoms to which they are attached, an unsaturated 5- to 7-membered carbocyclic ring which is optionally substituted by fluorine, chlorine, bromine, $C_1–C_4$-alkyl, $C_1–C_4$-alkoxy, $C_1–C_4$-halogenoalkyl, $C_1–C_4$-halogenoalkoxy, nitro or cyano, n represents 1, 2 or 3, Z represents

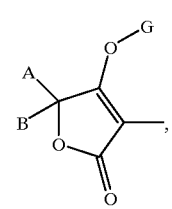

(2)

A represents hydrogen, in each case optionally fluorine- or chlorine-substituted $C_1–C_{10}$-alkyl, $C_2–C_6$-alkenyl, $C_1–C_8$-alk- oxy-$C_1–C_6$-alkyl, poly-$C_1–C_6$-alkoxy-$C_1–C_6$-alkyl, $C_1–C_8$- alkylthio-$C_1–C_6$-alkyl, cycloalkyl having 3 to 7 ring atoms which is optionally substituted by $C_1–C_4$-alkyl, $C_1–C_4$- alkoxy, fluorine or chlorine and in which, optionally, one or two methylene groups which are not directly adjacent are replaced by oxygen and/or sulfur, or represents phenyl, furanyl, pyridyl, imidazolyl, triazolyl, pyrazolyl, indolyl, thiazolyl, thienyl or phenyl-$C_1–C_4$-alkyl each of which is optionally substituted by fluorine, chlorine, bromine, $C_1–C_4$-alkyl, $C_1–C_4$-halogenoalkyl, $C_1–C_4$-alkoxy or nitro, B represents hydrogen, $C_1–C_{10}$-alkyl or $C_1–C_6$-alkoxy-$C_1–C_4$- alkyl, or A, B and the carbon atom to which they are attached represent a saturated or unsaturated $C_3–C_9$ spirocyclic ring system in which, optionally, one or two methylene groups which are not directly adjacent are replaced by oxygen and/or sulfur and which is optionally substituted by $C_1–C_6$-alkyl, $C_3–C_8$-cycloalkyl, $C_1–C_3$- halogenoalkyl, $C_1$–$C_6$-alkoxy, $C_1$–$C_6$-alkylthio, fluorine, chlorine or phenyl, or A, B and the carbon atom to which they are attached represent a $C_3$–$C_6$ spirocyclic ring system which is substituted by an alkyldendiyl group, which is optionally interrupted by one or two oxygen or sulfur atoms or by an alkylenedioxy group or by an alkylenedithio group, which, with the carbon atom to which it is attached, forms a further five- to seven-membered spirocyclic ring system, or A, B and the carbon atom to which they are attached represent a $C_3$–$C_6$ spirocyclic ring system in which two substituents together represent a saturated or mono- or polyunsaturated 5- or 6-membered ring which is optionally substituted by $C_1$–$C_5$-alkyl, $C_1$–$C_5$-alkoxy, fluorine, chlorine or bromine and which optionally contains an oxygen or sulfur atom, G represents hydrogen (a) or represents one of the groups

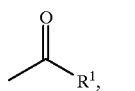  (b)

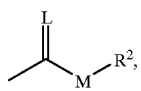  (c)

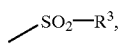  (d)

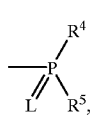  (e)

E or  (f)

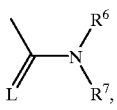  (g)

in which

E represents a metal ion equivalent or an ammonium ion,

L represents oxygen or sulfur, and

M represents oxygen or sulfur, $R^1$ represents in each case optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, poly-$C_1$–$C_6$-alkoxy-$C_1$–

$C_6$-alkyl, or cycloalkyl having 3 to 7 ring atoms which is optionally substituted by fluorine, chlorine or $C_1$–$C_5$-alkyl and in which, optionally, one or two methylene groups which are not directly adjacent are replaced by oxygen and/or sulfur, or represents phenyl which is optionally substituted by fluorine, chlorine, bromine, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulfonyl, or represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents pyrazolyl, thiazolyl, pyridyl, pyrimidyl, furanyl or thienyl, each of which is optionally substituted by fluorine, chlorine, bromine or $C_1$–$C_4$-alkyl, or represents phenoxy-$C_1$–$C_5$-alkyl which is optionally substituted by fluorine, chlorine, bromine or $C_1$–$C_4$-alkyl, or represents pyridyloxy-$C_1$–$C_5$-alkyl, pyrimidyloxy-$C_1$–$C_5$-alkyl or thiazolyloxy-$C_1$–$C_5$alkyl, each of which is optionally substituted by fluorine, chlorine, bromine, amino or $C_1$–$C_4$- alkyl, $R^2$ represents in each case optionally fluorine- or chlorine-substituted $C_1$–$C_{16}$-alkyl, $C_3$–$C_{16}$-alkenyl, $C_1$–$C_6$-alkoxy-$C_1$–$C_6$-alkyl or poly-$C_1$–$C_6$-alkoxy-$C_1$–$C_6$-alkyl, or represents $C_3$–$C_7$-cycloalkyl which is optionally substituted by fluorine, chlorine, $C_1$–$C_3$-alkyl or $C_1$–$C_3$- alkoxy, or represents phenyl or benzyl, each of which is optionally substituted by fluorine, chlorine, bromine, nitro, $C_1$–$C_4$-alkyl, $C_1$–$C_3$-alkoxy or $C_1$–$C_3$-halogenoalkyl, $R^3$ represents optionally fluorine- or chlorine-substituted $C_1$–$C_6$- alkyl or represents benzyl or phenyl each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, $R^4$ and $R^5$ represent, independently of one another, in each case optionally halogen-substituted $C_1$–$C_6$-alkyl, $C_1$–$C_6$-alkoxy, $C_1$–$C_6$-alkyl- amino, di-($C_1$–$C_6$-alkyl)-amino, $C_1$–$C_6$-alkylthio, $C_3$–$C_4$- alkenylthio, $C_3$–$C_6$-cycloalkylthio, or represent phenyl, phenoxy or phenylthio each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$- halogenoalkylthio, $C_1$–$C_3$-alkyl or $C_1$–$C_3$-halogenoalkyl, $R^6$ and $R^7$, independently of one another, represent hydrogen, in each case optionally fluorine-, chlorine- or bromine-substituted $C_1$–$C_6$- alkyl, $C_3$–$C_6$-cycloalkyl, $C_1$–$C_6$-alkoxy, $C_3C_6$-alkenyl, $C_1$–$C_6$- alkoxy-$C_1$–$C_6$-alkyl, phenyl which is optionally substituted by fluorine, chlorine, bromine, $C_1$–$C_5$-halogenoalkyl, $C_1$–$C_5$- alkyl or $C_1$–$C_5$-alkoxy, benzyl which is optionally substituted by fluorine, chlorine, bromine, $C_1$–$C_5$-alkyl, $C_1$–$C_5$- halogenoalkyl or $C_1$–$C_5$-alkoxy, or together represent $C_3$–$C_6$- alkanediyl in which, optionally, one methylene group is replaced by oxygen or sulfur, $R^{13}$ represents hydrogen, in each case optionally fluorine- or chlorine-substituted $C_1$–$C_6$-alkyl, $C_1$–$C_6$-alkoxy or $C_3$–$C_7$- cycloalkyl, or represents phenyl or benzyl each of which is optionally substituted by fluorine, chlorine, bromine, $C_1$–$C_4$- alkyl, $C_1$–$C_4$-alkoxy, $C_1$–$C_2$-halogenoalkyl, $C_1$–$C_2$-halogeno- alkoxy, nitro or cyano, $R^{14}$ and $R^{15}$ represent, independently of one another, hydrogen, $C_1$–$C_6$- alkyl, $C_1$–$C_6$-halogenoalkyl, $C_3$–$C_6$-cycloalkyl, or represent phenyl or benzyl each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, or together represent an optionally $C_1$–$C_3$-alkyl-substituted $C_4$–$C_5$-alkanediyl group, $R^{16}$ and $R^{17}$ are identical or different and represent $C_1$–$C_4$-alkyl, or $R^{16}$ and $R^{17}$ together represent a $C_2$–$C_3$-alkanediyl radical which is optionally substituted by $C_1$–$C_4$-alkyl or by phenyl which is optionally substituted by $C_1$–$c_2$-alkyl, $C_1$–$C_2$-halogenoalkyl, $C_1$–$C_2$-alkoxy, $C_1$–$C_2$-halogenoalkoxy, nitro or cyano.

4. A compound of the formula (I) as claimed in claim 1, in which

X represents fluorine, chlorine, bromine, methyl, ethyl, propyl, isopropyl, butyl, isobutyl, tert-butyl, trifluoromethyl, tri- fluoromethoxy, nitro or cyano or two substituents X form, together with the carbon atoms to which they are attached, an unsaturated 6-membered carbocyclic ring which is optionally substituted by fluorine, chlorine, bromine, methyl, methoxy, trifluoromethyl, trifluoromethoxy, nitro or cyano, n represents 1, 2 or 3, Z represents

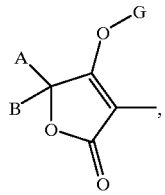 (2)

A represents hydrogen, in each case optionally fluorine- or chlorine-substituted $C_1$–$C_8$-alkyl, $C_2$–$C_4$-alkenyl, $C_1$–$C_6$-alk- oxy-$C_1$–$C_4$-alkyl, poly-$C_1$–$C_4$-alkoxy-$C_1$–$C_4$-alkyl, $C_1$–$C_6$- alkylthio-$C_1$–$C_4$-alkyl, cycloalkyl having 3 to 6 ring atoms in which, optionally, one methylene group is replaced by oxygen or sulfur, or represents phenyl, furanyl, pyridyl, imidazolyl, pyrazolyl, triazolyl, indolyl, thiazolyl, thienyl or benzyl each of which is optionally substituted by fluorine, chlorine, bromine, methyl, ethyl, propyl, isopropyl, methoxy, ethoxy, trifluoromethyl or nitro, B represents hydrogen, $C_1$–$C_8$-alkyl or $C_1$–$C_4$-alkoxy-$C_1$–$C_2$- alkyl, or A, B and the carbon atom to which they are attached represent a saturated or unsaturated $C_3$–$C_8$ spirocyclic ring system in which, optionally, one methylene group is replaced by oxygen or sulfur, and which is optionally mono-or poly-substituted by methyl, ethyl, propyl, isopropyl, butyl, isobutyl, sec-butyl, tert-butyl, cyclohexyl, trifluoromethyl, methoxy, ethoxy, propoxy, isopropoxy, butoxy, isobutoxy, sec-butoxy, tert-butoxy, methylthio, ethylthio, fluorine, chlorine or phenyl, or A, B and the carbon atom to which they are attached represent a $C_3$–$C_6$ spirocyclic ring system which is substituted by an alkyldendiyl group, which is optionally interrupted an oxygen or sulfur atom or by an alkylenedioxy group which, with the carbon atom to which it is attached, forms a further five- to seven membered spirocyclic ring system, or A, B and the carbon atom to which they are attached represent a $C_3$–$C_6$ spirocyclic ring system in which two substituents together represent a saturated or mono- or triunsaturated five- or six-membered ring which optionally contains an oxygen or sulfur atom, G represents hydrogen (a) or represents one of the groups

 (b)

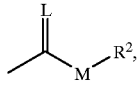 (c)

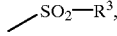 (d)

 (e)

E or (f)

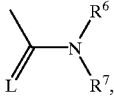 (g)

in which

E represents a metal ion equivalent or an ammoniumion,

L represents oxygen or sulfur, and

M represents oxygen or sulfur, $R^1$ represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl, or $C_3$–$C_6$-cycloalkyl which is optionally substituted by fluorine, chlorine, methyl, ethyl, propyl, isopropyl, butyl, isobutyl or tert-butyl and in which, optionally, one or two methylene groups which are not directly adjacent are replaced by oxygen and/or sulfur, or represents phenyl which is optionally substituted by fluorine, chlorine, bromine, methyl, ethyl, propyl, isopropyl, methoxy, ethoxy, trifluoromethyl, trifluoromethoxy, methylthio, ethylthio, methylsulfonyl, ethylsulfonyl or nitro, or represents benzyl which is optionally substituted by fluorine, chlorine, bromine, methyl, ethyl, propyl, isopropyl, methoxy, ethoxy, trifluoroethyl or trifluoromethoxy, or represents furanyl, thienyl, pyridyl, pyrimidyl, thiazolyl or pyrazolyl each of which is optionally substituted by fluorine, chlorine, bromine, methyl or ethyl, or represents phenoxy-$C_1$–$C_4$-alkyl which is optionally substituted by fluorine, chlorine, methyl or ethyl or represents pyridyloxy-$C_1$–$C_4$-alkyl, pyrimidyloxy-$C_1$–$C_4$-alkyl or thiazolyloxy-$C_1$–$C_4$alkyl, each of which is optionally substituted by fluorine, chlorine, amino, methyl or ethyl, $R^2$ represents in each case optionally fluorine- or chlorine-substituted $C_1$–$C_{14}$-alkyl, $C_3$–$C_{14}$-alkenyl, $C_1$–$C_4$-alkoxy-$C_1$–$C_6$-alkyl or poly-$C_1$–$C_4$-alkoxy-$C_1$–$C_6$-alkyl, or represents $C_3$–$C_6$-cycloalkyl which is optionally substituted by fluorine, chlorine, methyl, ethyl, propyl, isopropyl or methoxy, represents phenyl or benzyl, each of which is optionally substituted by fluorine, chlorine, nitro, methyl, ethyl, propyl, isopropyl, methoxy, ethoxy or trifluoromethyl, $R^3$ represents optionally fluorine- or chlorine-substituted $C_1$–$C_4$- alkyl or represents phenyl or benzyl each of which is optionally substituted by fluorine, chlorine, bromine, methyl, methoxy, trifluoromethyl, trifluoromethoxy, nitro or cyano, $R^4$ and $R^5$ represent, independently of one another, in each case optionally fluorine- or chlorine-substituted $C_1$–$C_4$-alkyl, $C_1$–$C_4$-alkoxy, $C_1$–$C_6$-alkoxy, $C_1$–$C_4$-alkylamino, di-($C_1$–$C_4$-alkyl)-amino, $C_1$–$C_4$-alkylthio, or represent phenyl, phenoxy or phenylthio each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl, $R^6$ and $R^7$, independently of one another, represent hydrogen, in each case optionally fluorine-, chlorine- or bromine-substituted $C_1$–$C_4$- alkyl, $C_3$–$C_6$-cycloalkyl, $C_1$–$C_4$-alkoxy, $C_3C_4$-alkenyl, $C_1$–$C_4$- alkoxy-$C_1$–$C_4$-alkyl, phenyl which is optionally substituted by fluorine, chlorine, bromine, $C_1$–$C_4$-halogenoalkyl, $C_1$–$C_4$- alkyl or $C_1$–$C_4$-alkoxy, or represents benzyl which is optionally substituted by fluorine, chlorine, bromine, $C_1$–$C_4$- alkyl, $C_1$–$C_4$-halogenoalkyl or $C_1$–$C_4$-alkoxy, or together represent $C_4$–$C_6$-alkanediyl in which, optionally, one methylene group is replaced by oxygen or sulfur.

5. A process for the preparation of a compound of the formula (I) as claimed in claim 1, which comprises (B) in order to obtain 3-thienyl-4-hydroxy-$\Delta^3$-dihydrofuranone derivatives of the formula (I-2-a)

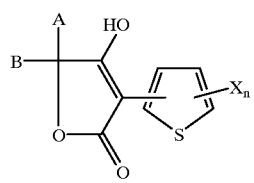

(I-2-a)

in which subjecting carboxylic esters of the formula (III)

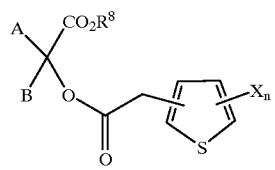

(III)

in which

A, B, X, and n have the meanings given in claim 1 and in which $R^8$ represents alkyl to intramolecular condensation in the presence of a diluent and in the presence of a base.

6. A compound of the formula (II)

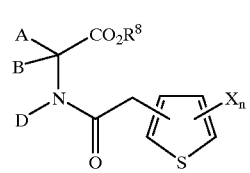

(II)

in which

A, B, X and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by a least heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom, and $R^8$ represents alkyl.

7. A compound of the formula (XXV)

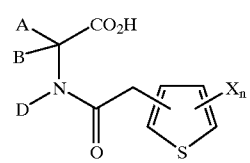

(XXV)

in which

A, B, X and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom.

8. A compound of the formula (XXVIII)

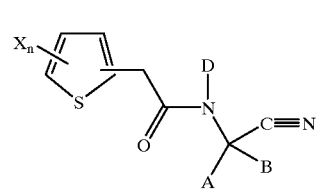

(XXVIII)

in which

A, B, X and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom.

9. A compound of the formula (III)

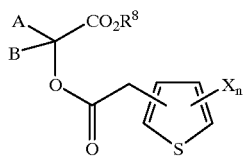

(III)

in which

A, B, X and n have the meanings given in claim 1 and $R^8$ represents alkyl.

10. A compound of the formula (IV)

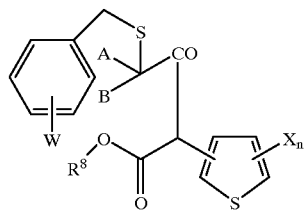

(IV)

in which

A, B, W, X and n have the meanings given in claim 1 and $R^8$ represents alkyl.

11. A compound of the formula (V)

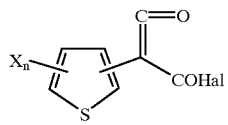

(V)

in which

X and n have the meanings given in claim 1 and

Hal represents chlorine or bromine.

12. A compound of the formula (X)

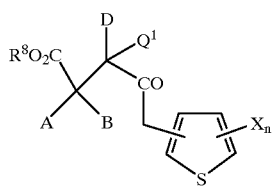

(X)

in which

A, B, X and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom and $Q^1$ represents hydrogen or optionally substituted alkyl and $R^8$ represents alkyl.

13. A compound of the formula (XXXV)

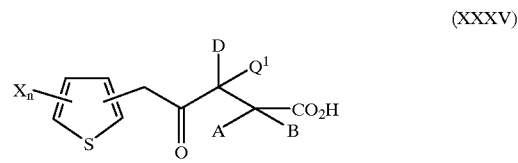

(XXXV)

in which

A, B, X and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom, and $Q^1$ represents hydrogen or optionally substituted alkyl.

14. A compound of the formula (XXXVIII)

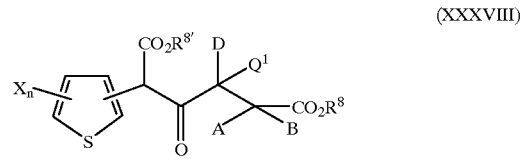

(XXXVIII)

in which

A, B, X and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom, and $Q^1$ represents hydrogen or optionally substituted alkyl and $R^8$ and $R^{8'}$ represents alkyl.

15. A compound of the formula (X)

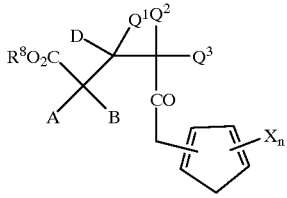
(XI)

in which

A, B, X and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom, and in which $Q^1$, $Q^2$ and $Q^3$, independently of one another, represent hydrogen or optionally substituted alkyl, or B and $Q^1$ together represent an optionally substituted alkanediyl group, $R^8$ represents alkyl.

16. A compound of the formula (XL)

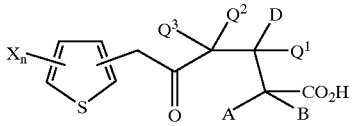
(XL)

in which

A, B, X and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom, and in which $Q^1$, $Q^2$ and $Q^3$, independently of one another, represent hydrogen or optionally substituted alkyl, or B and $Q^1$ together represent an optionally substituted alkanediyl group.

17. A compound of the formula (XLII)

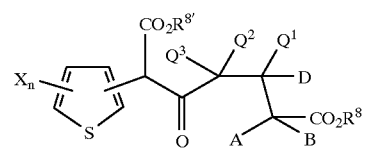
(XLII)

in which

A, B, Z and n have the meanings given in claim 1 and in which

D represents hydrogen or optionally substituted radicals from the series consisting of alkyl, alkenyl, alkinyl, alkoxyalkyl, alkylthioalkyl, saturated or unsaturated cycloalkyl which is optionally interrupted by at least one heteroatom, arylalkyl, aryl, hetarylalkyl or hetaryl, or A and D, together with the atoms to which they are attached, represent a saturated or unsaturated, unsubstituted or substituted ring which is optionally interrupted by at least one heteroatom, and in which $Q^1$, $Q^2$ and $Q^3$, independently of one another, represent hydrogen or optionally substituted alkyl, or B and $Q^1$ together represent an optionally substituted alkanediyl group, $R^8$ and $R^{8'}$ represents alkyl.

18. A pest-control composition or weed-control composition, which comprises at least one compound of the formula (I) as claimed in claim 1.

19. A method of controlling pests and weeds, which comprises causing a compound of the formula (I) as claimed in claim 1 to act on pests and/or their habitat or on weeds and/or their habitat.

20. A process for the production of pest-control compositions and weed-control compositions, which comprises mixing compounds of the formula (I) as claimed in claim 1 with extenders and/or surface-active agents.

* * * * *